United States Patent
Huang et al.

(10) Patent No.: US 8,680,089 B2
(45) Date of Patent: Mar. 25, 2014

(54) FUSED PYRIDINE DERIVATIVES

(75) Inventors: Zhenhua Huang, Jinan (CN); Yan Zhang, Jinan (CN); Yuntao Song, Jinan (CN)

(73) Assignee: Xuanzhu Pharma Co., Ltd., Jinan, Shandong (CN)

( * ) Notice: Subject to any disclaimer, the term of this patent is extended or adjusted under 35 U.S.C. 154(b) by 0 days.

(21) Appl. No.: 13/522,304

(22) PCT Filed: Jan. 17, 2011

(86) PCT No.: PCT/CN2011/000068
§ 371 (c)(1),
(2), (4) Date: Jul. 13, 2012

(87) PCT Pub. No.: WO2011/085643
PCT Pub. Date: Jul. 21, 2011

(65) Prior Publication Data
US 2012/0289497 A1    Nov. 15, 2012

(30) Foreign Application Priority Data

Jan. 15, 2010 (CN) .......................... 2010 1 0011869
Apr. 29, 2010 (CN) .......................... 2010 1 0175404
Jul. 10, 2010 (CN) .......................... 2010 1 0230754
Sep. 17, 2010 (CN) .......................... 2010 1 0291056

(51) Int. Cl.
| | |
|---|---|
| *C07D 471/04* | (2006.01) |
| *A61K 31/437* | (2006.01) |
| *A61K 31/4545* | (2006.01) |
| *A61K 31/4745* | (2006.01) |
| *A61K 31/496* | (2006.01) |
| *A61K 31/5377* | (2006.01) |
| *A61K 31/55* | (2006.01) |
| *A61K 31/551* | (2006.01) |
| *A61P 3/06* | (2006.01) |
| *A61P 3/08* | (2006.01) |
| *A61P 3/10* | (2006.01) |
| *C07D 498/04* | (2006.01) |
| *C07D 513/04* | (2006.01) |

(52) U.S. Cl.
USPC ............... 514/210.21; 514/217.07; 514/218; 514/234; 514/253.04; 514/278; 514/293; 514/300; 514/301; 514/302; 514/303; 540/575; 540/597; 544/127; 544/362; 546/15; 546/82; 546/113; 546/114; 546/116; 546/118

(58) Field of Classification Search
None
See application file for complete search history.

(56) References Cited

U.S. PATENT DOCUMENTS 7,524,847 B2    4/2009   Kira et al.

FOREIGN PATENT DOCUMENTS

| CN | 1745080 A | 3/2006 |
|---|---|---|
| CN | 101379065 A | 3/2009 |
| CN | 101397300 A | 4/2009 |
| WO | WO 2004/050656 A1 | 6/2004 |
| WO | WO 2009/099594 A1 | 8/2009 |

OTHER PUBLICATIONS

First Office Action issued by the SIPO of China for Chinese Application No. 201010230754.8, with English translation [date untranslated], 7 pages.

*Primary Examiner* — Janet L Andres
*Assistant Examiner* — Timothy R Rozof
(74) *Attorney, Agent, or Firm* — Seed IP Law Group PLLC

(57) ABSTRACT

Fused pyridine derivatives shown as the general formula (I), and their pharmaceutically acceptable salts, stereoisomers or solvates thereof are disclosed, which belong to the technical field of medicines. The $R^1$, $R^2$, $R^3$, Q, X and Y substituents in formula (I) are defined as in the description. Also disclosed are the preparation methods, pharmaceutical compositions comprising the compounds and uses of the compounds in the manufacture of the medicine for the treatment and/or prevention of noninsulin-dependent diabetes, hyperglycemia, hyperlipidemia and insulin resistance.

(I)

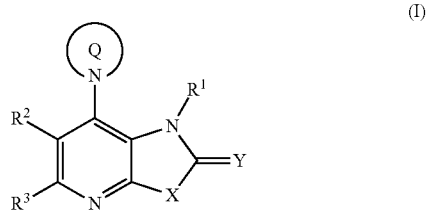

18 Claims, No Drawings

FUSED PYRIDINE DERIVATIVES

FIELD OF THE INVENTION

The present invention belongs to the technical field of medicines, and specifically relates to fused pyridine derivatives, their pharmaceutically acceptable salts, stereoisomers or solvates thereof, the preparation methods of these compounds, pharmaceutical compositions comprising the compounds and uses of the compounds in the manufacture of the medicine for the treatment and/or prevention of noninsulin-dependent diabetes, hyperglycemia, hyperlipidemia and insulin resistance.

BACKGROUND OF THE INVENTION

Diabetes mellitus is a systemic chronic metabolic disease caused by a blood glucose level higher than normal level due to loss of blood glucose control. It is basically classified into four categories, including: type I (insulin-dependent) and type II (non-insulin-dependent), the other type and gestational diabetes. Type I and type II diabetes are primary diabetes, which are the two most common forms caused by the interaction of genetic and environmental factors. The cause of diabetes is very complicated, but in the final analysis, is due to absolute or relative insulin deficiency, or insulin resistance. It is characterized by the metabolic disorder of carbohydrate, protein, fat, electrolytes and water caused by absolute or relative insulin deficiency and the reduced sensitivity of target cells to insulin.

In recent years, because of the improvement of living level, changes in the diet structure, the increasingly intense pace of life and lifestyle of less exercise and many other factors, the global incidence of diabetes is rapidly increasing, so that diabetes has become the third chronic disease which has a serious threat to human health next to tumor and cardiovascular diseases. Presently, the number of the patients suffering from diabetes has exceeded 120 million in the world, and the number in our country is the second largest in the world. According to statistics, up to 40 million people have been diagnosed as diabetes in China, and the number of the patients is increasing at a rate of 1 million per year. Among them, patients having type I and type II diabetes accounted for 10% and 90% respectively. Diabetes has become the increasingly concerned public health issue.

The main drugs currently used for the treatment of type I diabetes are insulin preparations and their substitutes; for the treatment of type II diabetes, the main drugs are oral hypoglycemic agents, generally divided into sulfonylureas, biguanides, traditional Chinese medicine preparations, other hypoglycemic agents, and auxiliary medication. Although these drugs have good effects, they can not maintain long-term efficacy in reducing the high blood glucose, and can not effectively alleviate the condition against the cause of diabetes. Many of the anti-diabetic drugs can well control the blood glucose at the beginning, but their efficacy can not be maintained when the treatment using such drugs are continuously used. It is one of the main reasons why combination therapies or drugs in different classes are used. However, the existing anti-diabetic drugs is lack of long-term efficacy mainly because their mechanism of action is to increase the sensitivity of target tissues to insulin action or improve insulin-producing activity of pancreas, but these drugs have no targeted effect to the reduced function of the pancreatic β cell, which is the fundamental cause of diabetes.

Dipeptidyl peptidase-IV (DPP-IV) is widely present in the body, and is a cell surface protein involved in a variety of biological functions. It can degrade many active enzymes in vivo, such as glucagon like peptide-1 (GLP-1), glucose-dependent insulinotropic polypeptide (GIP), neuropeptide, substance P, and chemokines and the like. The deficiency of GLP-1 and GIP is the main cause resulting in type II diabetes (i.e., non-insulin-dependent diabetes). DPP-IV inhibitor is a new generation of anti-diabetic drug. It protects the activity of GLP-1, GIP and the like, stimulates the secretion of insulin, lowers blood glucose level by inhibiting the activity of DPP-IV, and does not cause hypoglycemia, weight gain, edema and other side effects. Its effect for lowering blood glucose level stops when a normal blood glucose level has been reached, and hypoglycemia will not occur. It can be used for a long term, and can repair the function of β-cells.

Sitagliptin is the first marketed DPP-IV inhibitor. It rapidly became a "blockbuster" drug after marketed in 2006 by Merck. The FDA approved the saxagliptin developed by AstraZeneca and Bristol-Myers Squibb on Jul. 31, 2009. SYR-322 developed by Takeda has an activity and selectivity better than that of sitagliptin and saxagliptin, and is currently in the phase of pre-registration. In addition, there are three drugs in clinical phase III: BI-1356 (linagliptin) developed by Boehringer Ingelheim, PF-734200 (gosogliptin) developed by Pfizer Inc, and PHX1149 (dutogliptin) developed by Phenomix Inc. Nine drugs are in the clinical phase II, and seven drugs are in clinical phase I.

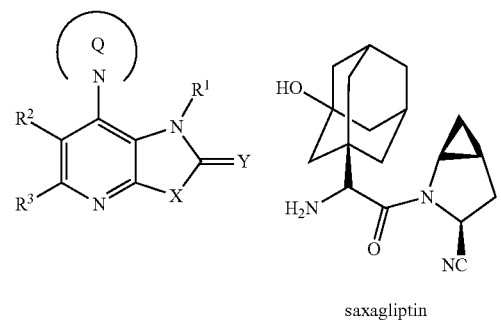

saxagliptin

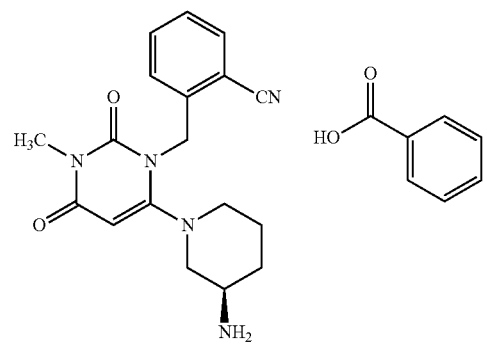

SYR-322

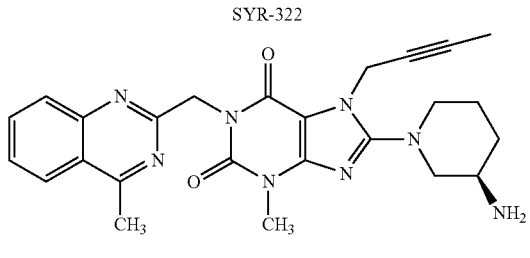

BI-1356

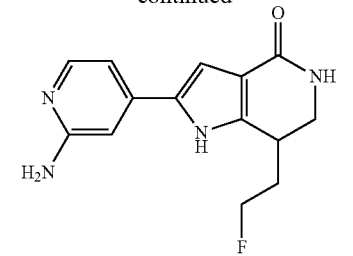

PF-734200

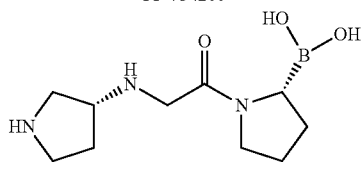

PHR1149

However, the limited varieties of drugs can not satisfy the clinical requirements. Accordingly, there is an urgent need for development of novel DPP-IV inhibitors with potency and safety profile to satisfy the clinical use.

SUMMARY OF THE INVENTION

In order to solve the above technical problem, further improve and optimize DPP-IV inhibitors, the inventor provides novel DPP-IV inhibitors after extensive investigation.

The technical solutions of the present invention are shown as follows.

The present invention provides compounds represented by general formula (I), their pharmaceutically acceptable salts, stereoisomers or solvates thereof:

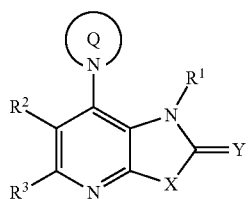

(I)

wherein: $R^1$ is $C_{1-6}$ alkyl, $C_{3-6}$ alkenyl or $C_{2-6}$ alkynyl, which are unsubstituted or substituted by halogen atom, hydroxy, amino, carboxyl, carbamoyl or aminosulfonyl, or aryl $C_{1-6}$ alkyl unsubstituted or substituted by 1 to 5 substituents V, wherein the substituent V is independently selected from cyano, $C_{2-6}$ alkynyl, halogen atom, hydroxy, amino, carboxyl, $C_{1-6}$ alkyl, $C_{1-6}$ alkoxy, carbamoyl, cyano $C_{1-6}$ alkyl, halogen $C_{1-6}$ alkyl, hydroxy $C_{1-6}$ alkyl, amino $C_{1-6}$ alkyl, carboxyl $C_{1-6}$ alkyl, halogen $C_{1-6}$ alkoxy, hydroxy $C_{1-6}$ alkoxy, amino $C_{1-6}$ alkoxy, carboxyl $C_{1-6}$ alkoxy, $C_{1-6}$ alkylamino, $C_{1-6}$ alkoxyamino or di-($C_{1-6}$ alkyl)amino;

$R^2$ and $R^3$ are independently from each other hydrogen atom, halogen atom, cyano, amino, hydroxy, carboxyl, $C_{1-6}$ alkylamino, di-($C_{1-6}$ alkyl)amino, $C_{3-6}$ cycloalkyl, $C_{1-6}$ alkyl or $C_{1-6}$ alkoxy which are unsubstituted or substituted by halogen atom, hydroxy, amino, carboxyl, cyano, carbamoyl, aminosulfonyl, or $R^2$ and $R^3$ together with the C atoms they are attached to form a phenyl, 5- to 6-membered saturated or unsaturated heterocyclyl group containing at least one nitrogen atom or $C_{3-6}$ cycloalkyl;

X is O, S, $NR^4$ or $CR^5R^6$, $R^4$ is selected from hydrogen atom, $C_{1-6}$ alkyl, halogen $C_{1-6}$ alkyl, $C_{2-6}$ alkenyl or $C_{3-6}$ cycloalkyl, $R^5$ and $R^6$ are independently selected from hydrogen atom, halogen atom, $C_{1-6}$ alkyl, halogen $C_{1-6}$ alkyl, $C_{1-6}$ alkoxy, halogen $C_{1-6}$ alkoxy, hydroxy $C_{1-6}$ alkyl, amino $C_{1-6}$ alkyl or $C_{3-6}$ cycloalkyl, or $R^5$ and $R^6$ together with the C atoms they are attached to form $C_{3-6}$ cycloalkyl;

Y is O, S or $NR^7$, $R^7$ is hydrogen atom, carbamoyl, $C_{1-6}$ alkylcarbonyl, $C_{3-6}$ cycloalkyl, or $C_{1-6}$ alkyl, $C_{1-6}$ alkoxy, aryl $C_{0-6}$ alkyl or aryl $C_{0-6}$ alkoxy, which are unsubstituted or substituted by halogen atom, hydroxy, amino, carboxyl or carbamoyl;

Q is 3- to 8-membered saturated or unsaturated heterocyclyl group containing at least one nitrogen atom, unsubstituted or substituted by 1 to 5 substituents W, the said substituent W is independently selected from amino, $C_{1-6}$ alkylamino, di-($C_{1-6}$ alkyl)amino, amino $C_{1-6}$ alkyl, hydroxy $C_{1-6}$ alkyl, carboxyl $C_{1-6}$ alkyl, carbamoyl, $C_{1-6}$ alkyl, halogen $C_{1-6}$ alkyl, $C_{1-6}$ alkoxy, halogen $C_{1-6}$ alkoxy, halogen atom, formimino, $C_{1-6}$ alkylcarbonylaminomethyl, $C_{1-6}$ alkylcarbonyloxyl, $C_{1-6}$ alkylcarbamoyl or $C_{1-6}$ alkoxyformyl.

In an embodiment of the present invention, the following compounds are preferred:

wherein: $R^1$ is $C_{3-6}$ alkenyl, $C_{3-6}$ alkynyl, or aryl $C_{1-6}$ alkyl unsubstituted or substituted by 1 to 3 substituents V, wherein the substituent V is independently selected from cyano, $C_{2-6}$ alkynyl, halogen atom, hydroxy, amino, carboxyl, $C_{1-6}$ alkyl, $C_{1-6}$ alkoxy, carbamoyl, cyano $C_{1-6}$ alkyl, halogen $C_{1-6}$ alkyl, hydroxy $C_{1-6}$ alkyl, amino $C_{1-6}$ alkyl, carboxyl $C_{1-6}$ alkyl, halogen $C_{1-6}$ alkoxy, $C_{1-6}$ alkylamino, $C_{1-6}$ alkoxyamino or di-($C_{1-6}$ alkyl)amino;

$R^2$ and $R^3$ are independently from each other hydrogen atom, halogen atom, cyano, amino, hydroxy, carboxyl, $C_{1-6}$ alkylamino, di-($C_{1-6}$ alkyl)amino, $C_{1-6}$ alkyl or $C_{1-6}$ alkoxy unsubstituted or substituted by halogen atom, hydroxy, amino, or $R^2$ and $R^3$ together with the C atoms they are attached to form a phenyl, 5- to 6-membered saturated or unsaturated heterocyclyl group containing at least one nitrogen atom or $C_{5-6}$ cycloalkyl;

X is O, S, $NR^4$ or $CR^5R^6$, $R^4$ is selected from hydrogen atom, $C_{1-6}$ alkyl, halogen $C_{1-6}$ alkyl, $C_{2-6}$ alkenyl or $C_{3-6}$ cycloalkyl, $R^5$ and $R^6$ are independently selected from hydrogen atom, halogen atom, $C_{1-6}$ alkyl, halogen $C_{1-6}$ alkyl, $C_{1-6}$ alkoxy, halogen $C_{1-6}$ alkoxy or $C_{3-6}$ cycloalkyl, or $R^5$ and $R^6$ together with the C atoms they are attached to form $C_{3-6}$ cycloalkyl;

Y is O, S or $NR^7$, $R^7$ is hydrogen atom, $C_{3-6}$ cycloalkyl, or $C_{1-6}$ alkyl $C_{1-6}$ alkoxy, phenyl $C_{0-6}$ alkyl or phenyl $C_{0-6}$ alkoxy, which are unsubstituted or substituted by halogen atom, hydroxy, amino, carboxyl or carbamoyl;

Q is 4- to 7-membered saturated or unsaturated heterocyclyl group containing at least one nitrogen atom, unsubstituted or substituted by 1 to 3 substituents W, the said substituent W is independently selected from halogen atom, amino, $C_{1-6}$ alkylamino, di-($C_{1-6}$ alkyl)amino, amino $C_{1-6}$ alkyl, hydroxy $C_{1-6}$ alkyl, carboxyl $C_{1-6}$ alkyl, carbamoyl, $C_{1-6}$ alkyl, halogen $C_{1-6}$ alkyl, $C_{1-6}$ alkoxy, halogen $C_{1-6}$ alkoxy, formimino, $C_{1-6}$ alkylcarbonylaminomethyl, $C_{1-6}$ alkylcarbonyloxyl, $C_{1-6}$ alkylcarbamoyl or $C_{1-6}$ alkoxyformyl.

In an embodiment of the present invention, the following compounds are preferred:

wherein: $R^1$ is aryl $C_{1-4}$ alkyl unsubstituted or substituted by 1 to 3 substituents V, wherein the substituent V is independently selected from cyano, cyano $C_{1-4}$ alkyl, $C_{2-4}$ alkynyl, halogen atom, $C_{1-4}$ alkyl, halogen $C_{1-4}$ alkyl, $C_{1-4}$ alkoxy, halogen $C_{1-4}$ alkoxy, amino, $C_{1-4}$ alkylamino, hydroxy, hydroxy$C_{1-4}$ alkyl or carbamoyl;

$R^2$ and $R^3$ are independently from each other hydrogen atom, halogen atom, cyano, carboxyl, $C_{1-4}$ alkylamino, di-($C_{1-4}$ alkyl)amino,
$C_{1-4}$ alkyl or $C_{1-4}$ alkoxy unsubstituted or substituted by halogen atom, hydroxy, amino, or $R^2$ and $R^3$ together with the C atoms they are attached to form a phenyl, pyridyl, pyrrolidinyl, imidazolidinyl, oxazolidinyl, thiazolidinyl, cyclopentyl or cyclohexyl;

X is O, S, $NR^4$ or $CR^5R^6$,
$R^4$ is selected from hydrogen atom, $C_{1-4}$ alkyl, halogen $C_{1-4}$ alkyl, $C_{2-4}$ alkenyl or $C_{3-6}$ cycloalkyl,
$R^5$ and $R^6$ are independently selected from hydrogen atom, halogen atom, $C_{1-4}$ alkyl, halogen $C_{1-4}$ alkyl, $C_{1-4}$ alkoxy, halogen $C_{1-4}$ alkoxy or $C_{3-5}$ cycloalkyl, or
$R^5$ and $R^6$ together with the C atoms they are attached to form $C_{3-6}$ cycloalkyl;
Y is O, S or $NR^7$, $R^7$ is hydrogen atom or $C_{1-4}$ alkyl;

Q is azetidinyl, pyrrolidinyl, pyrrolyl, 4,5-dihydroimidazolyl, imidazolyl, pyrazolidinyl, pyrazolyl, 4,5-dihydropyrazolyl, pyrazolidinyl, piperidyl, homopiperazinyl, homopiperidyl, piperazinyl or morpholinyl, which are unsubstituted or substituted by 1 to 3 substituents W, the said substituent W is independently selected from halogen atom, amino, $C_{1-4}$ alkylamino, di-($C_{1-4}$ alkyl)amino, amino $C_{1-4}$ alkyl, hydroxy $C_{1-4}$ alkyl, carboxyl $C_{1-4}$ alkyl, carbamoyl, $C_{1-4}$ alkyl, halogen $C_{1-4}$ alkyl, $C_{1-4}$ alkoxy, formimino, $C_{1-4}$ alkylcarbonylaminomethyl, $C_{1-4}$ alkylcarbonyloxyl, $C_{1-4}$ alkylcarbamoyl, $C_{1-4}$ alkoxyformyl, acetamido or 2-cyano-phenylmethylamino In an embodiment of the present invention, the following compounds are preferred:

wherein: $R^1$ is aryl $C_{1-4}$ alkyl unsubstituted or substituted by 1 to 3 substituents V, wherein the substituent V is independently selected from cyano, cyanomethyl, acetenyl, fluorine atom, chlorine atom, methyl, trifluoromethyl, methoxy, trifluoromethoxy, amino, methylamino, hydroxymethyl or carbamoyl;

$R^2$ and $R^3$ are independently from each other hydrogen atom, fluorine atom, chlorine atom, cyano, methyl, ethyl, fluoromethyl, difluoromethyl, trifluoromethyl, hydroxymethyl, carboxyl, aminomethyl, methylamino, di-(methyl)amino, methoxy, trifluoromethoxy, or $R^2$ and $R^3$ together with the C atoms they are attached to form a phenyl or pyridyl;

X is O, S, $NR^4$ or $CR^5R^6$,
$R^4$ is selected from hydrogen atom, methyl, ethyl, isopropyl, trifluoromethyl, ethenyl or cyclopropyl,
$R^5$ and $R^6$ are independently selected from hydrogen atom, fluorine atom, methyl, ethyl, trifluoromethyl or methoxy, or
$R^5$ and $R^6$ are linked together and together with the C atoms they are attached to form cyclopropyl, cyclobutyl, cyclopentyl or cyclohexyl;
Y is O, S or $NR^7$, $R^7$ is hydrogen atom or methyl;

Q is pyrrolidinyl, piperazinyl, piperidyl, homopiperazinyl, homopiperidyl or azetidinyl, which are unsubstituted or substituted by 1 to 2 substituents W, the said substituent W is independently selected from fluorine atom, chlorine atom, amino, methylamino, di-(methyl)amino, aminomethyl, methyl, ethyl, methoxy, methoxy formyl, hydroxymethyl, acetamido or 2-cyano-phenylmethylamino In an embodiment of the present invention, the following compounds are further preferred:

wherein: $R^1$ is arylmethyl unsubstituted or substituted by 1 to 3 substituents V, wherein the substituent V is independently selected from cyano, acetenyl, fluorine atom, chlorine atom, methyl, trifluoromethyl, methoxy or trifluoromethoxy;

$R^2$ and $R^3$ are independently from each other hydrogen atom, fluorine atom, chlorine atom, methyl, ethyl, fluoromethyl, difluoromethyl, trifluoromethyl, hydroxymethyl, carboxyl, aminomethyl, methylamino, di-(methyl)amino, methoxy, or $R^2$ and $R^3$ together with the C atoms they are attached to form a phenyl or pyridyl;

X is O, $NR^4$ or $CR^5R^6$,
$R^4$ is selected from hydrogen atom, methyl, ethyl, isopropyl or trifluoromethyl,
$R^5$ and $R^6$ are independently selected from hydrogen atom, fluorine atom, methyl, ethyl or trifluoromethyl;
Y is O or S;

Q is pyrrolidinyl, piperazinyl, piperidyl, homopiperazinyl, homopiperidyl or azetidinyl, which are unsubstituted or substituted by 1 to 2 substituents W, the said substituent W is independently selected from fluorine atom, chlorine atom, amino, methylamino, aminomethyl, methyl, di-(methyl)amino, acetamido or 2-cyano-phenylmethylamino In an embodiment of the present invention, the following compounds are even further preferred:

wherein: $R^1$ is phenylmethyl or naphthylmethyl, which are unsubstituted or substituted by 1 to 3 substituents V, wherein the substituent V is independently selected from cyano, acetenyl, fluorine atom, chlorine atom or methyl;

$R^2$ and $R^3$ are independently from each other hydrogen atom, fluorine atom, chlorine atom, methyl, ethyl, fluoromethyl, difluoromethyl, trifluoromethyl, hydroxymethyl, carboxyl, aminomethyl, methylamino, di-(methyl)amino, or $R^2$ and $R^3$ together with the C atoms they are attached to form a phenyl;

X is O, $NR^4$ or $CR^5R^6$,
$R^4$ is selected from hydrogen atom, methyl, ethyl or isopropyl,
$R^5$ and $R^6$ are independently selected from hydrogen atom, methyl or ethyl;
Y is O or S;

Q is pyrrolidinyl, piperazinyl, piperidyl, homopiperazinyl, homopiperidyl or azetidinyl, which are unsubstituted or substituted by 1 to 2 substituents W, the said substituent W is independently selected from fluorine atom, amino, methylamino, methyl, di-(methyl)amino, acetamido or 2-cyano-phenylmethylamino In an embodiment of the present invention, the following compounds are even further preferred:

wherein: $R^1$ is phenylmethyl or naphthylmethyl, which are unsubstituted or substituted by 1 to 2 substituents V, wherein the substituent V is independently selected from cyano, acetenyl, fluorine atom or chlorine atom;

$R^2$ and $R^3$ are independently from each other hydrogen atom, chlorine atom, methyl, ethyl, hydroxymethyl, carboxyl, aminomethyl, methylamino, di-(methyl)amino, or $R^2$ and
$R^3$ together with the C atoms they are attached to form a phenyl;
X is O, $NR^4$ or $CR^5R^6$,
$R^4$ is selected from hydrogen atom, methyl, ethyl or isopropyl, $R^5$ and $R^6$ are independently selected from hydrogen atom or methyl;

Y is O or S;

Q is pyrrolidinyl, piperazinyl, piperidyl, homopiperazinyl, homopiperidyl or azetidinyl, which are unsubstituted or substituted by one substituent W, the said substituent W is selected from amino, methylamino, di-(methyl)amino, acetamido or 2-cyano-phenylmethylamino.

The "halogen atom" as described in the present invention includes fluorine atom, chlorine atom, bromine atom, iodine atom.

The term "$C_{1-6}$ alkyl" included in "$C_{1-6}$ alkyl, cyano-$C_{1-6}$ alkyl, hydroxy $C_{1-6}$ alkyl, amino $C_{1-6}$ alkyl, carboxyl$_{1-6}$ alkyl, $C_{1-6}$ alkylamino, di-($C_{1-6}$ alkyl)amino, $C_{1-6}$ alkylcarbamoyl, di-($C_{1-6}$ alkyl)carbamoyl, $C_{1-6}$ alkylcarbonyl, $C_{1-6}$ alkylcarbonyloxyl, $C_{1-6}$ alkylcarbonylaminomethyl, aryl $C_{1-6}$ alkyl" as described in the present invention denotes a straight chain or branched chain alkyl having 1 to 6 carbon atoms derivated from a hydrocarbon moiety by removing a hydrogen atom, for example, methyl, ethyl, n-propyl, isopropyl, n-butyl, isobutyl, sec.-butyl, tert-butyl, n-pentyl, isopentyl, 2-methylbutyl, neopentyl, 1-ethyl propyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl, and the like. The term "$C_{1-4}$ alkyl" denotes specific examples having 1 to 4 carbon atoms included in the above examples.

The "halogen" included in "halogen $C_{1-6}$ alkyl, halogen $C_{1-4}$ alkyl, halogen $C_{1-6}$ alkoxy, halogen $C_{1-4}$ alkoxy" as described in the present invention denotes that one or more hydrogen atoms on the carbon atom in $C_{1-6}$ alkyl, $C_{1-4}$ alkyl, $C_{1-6}$ alkoxy, $C_{1-4}$ alkoxy are substituted by halogen atom(s).

The term "$C_{3-6}$ cycloalkyl" as described in the present invention denotes cyclopropyl, cyclobutyl, 1-methylcyclobutyl, cyclopentyl, cyclohexyl and the like.

The term "$C_{1-6}$ alkoxy" included in "$C_{1-6}$ alkoxy, hydroxy $C_{1-6}$ alkoxy, amino $C_{1-6}$ alkoxy, carboxyl $C_{1-6}$ alkoxy, $C_{1-6}$ alkoxyamino, $C_{1-6}$ alkoxyformyl" as described in the present invention denotes a group formed by the term "$C_{1-6}$ alkyl" attached to other moieties through an oxygen atom, for example, methoxy, ethoxyl, propoxy, isopropoxy, butoxy, isobutoxy, tert-butoxy, sec.-butoxy, pentyloxy, neopentyloxy, hexyloxy and the like. The term "$C_{1-4}$ alkoxy" denotes a group formed by the term "$C_{1-4}$ alkyl" attached to other moieties through an oxygen atom.

The term "$C_{2-6}$ alkenyl" as described in the present invention denotes a straight chain, branched chain or cyclic alkenyl containing double bonds having 2 to 6 carbon atoms, for example, 1-propenyl, 2-propenyl, 1-butenyl, 2-butenyl, 1-pentenyl, 2-pentenyl, 3-pentenyl, 1-hexenyl, 2-hexenyl, 3-hexenyl, cyclopropeny, cyclopentenyl, cyclohexenyl and the like. The "$C_{3-4}$ alkenyl" as described in the present invention denotes the specific example of straight chain, branched chain or cyclic alkenyl containing double bonds having 3 to 4 carbon atoms.

The term "$C_{2-6}$ alkynyl" as described in the present invention denotes a straight chain, branched chain or cyclic alkynyl containing triple bonds having 2 to 6 carbon atoms, for example, acetenyl, propinyl, 2-butynl, 2-pentynyl, 3-pentynyl, 2-hexynyl, 3-hexynyl, cyclopropinyl, cyclobutynl, cyclopentynyl, cyclohexynyl and the like. The "$C_{3-4}$ alkynyl" as described in the present invention denotes the specific example of straight chain, branched chain or cyclic alkynyl containing triple bonds having 3 to 4 carbon atoms.

The "aryl" as described in the present invention denotes an aromatic ring, for example, phenyl, naphthyl, anthryl and the like.

The "3- to 8-membered saturated or unsaturated heterocyclyl group containing at least one nitrogen atom" as described in the present invention includes "3- to 8-membered saturated heterocyclyl group containing at least one nitrogen atom" and "3- to 8-membered unsaturated heterocyclyl group containing at least one nitrogen atom".

The specific examples of "3- to 8-membered saturated heterocyclyl group containing at least one nitrogen atom" includes, for example, aziridinyl (azacyclopropyl), diaziridinyl (diazacyclopropyl), azacyclobutyl (i.e., azetidinyl), 1,2-diazetidine, pyrrolidine, imidazolidine, pyrazolidine, piperidine, piperazine, morpholine, azepine, 1,4-diazacycloheptane and the like. The "4- to 7-membered saturated heterocyclyl group containing at least one nitrogen atom" is preferred, for example, azacyclobutyl (i.e., azetidinyl), 1,2-diazetidine, pyrrolidine, imidazolidine, pyrazolidine, piperidine, piperazine, morpholine, azepine, 1,4-diazacycloheptane and the like. The "5- to 6-membered saturated heterocyclyl group containing at least one nitrogen atom" is further preferred, for example, pyrrolidine, imidazolidine, pyrazolidine, piperidine, piperazine, morpholine and the like.

The specific examples of "3- to 8-membered unsaturated heterocyclyl group containing at least one nitrogen atom" includes, for example, 2H-aziridinyl (2H-azacyclopropenyl), 3H-diaziridinyl (3H-azacyclopropenyl), azete, 1,2-diazetine, pyrrole, dihydropyrrole, imidazole, 4,5-dihydroimidazole, pyrazole, 4,5-dihydropyrazole, 1,2,3-triazole, 1,2,4-triazole, tetrazole, oxazole, 4,5-dihydrooxazole, isoxazole, 4,5-dihydroisoxazole, 2,3-dihydroisoxazole, 1,2,3-oxdiazole, 1,2,5-oxdiazole, thiazole, 4,5-dihydrothiazole, isothiazole, 1,2,3-thiadiazole, 1,2,4-thiadiazole, 1,3,4-thiadiazole, pyridine, pyridazine, pyrimidine, pyrazine, 1,2,3-triazine, 1,2,4-triazine, 1,3,5-triazine, 1,2,4,5-tetrazine, 2H-1,2-oxazine, 4H-1,2-oxazine, 6H-1,2-oxazine, 2H-1,3-oxazine, 4H-1,3-oxazine, 5,6-dihydro-4H-1,3-oxazine, 6H-1,3-oxazine, 2H-1,4-oxazine, 4H-1,4-oxazine, 2H-1,3-thiazine, 4H-1,3-thiazine, 5,6-dihydro-4H-1,3-thiazine, 6H-1,3-thiazine, 2H-1,4-thiazine, 4H-1,4-thiazine and the like. The "4- to 7-membered unsaturated heterocyclyl group containing at least one nitrogen atom" is preferred, for example, azete, 1,2-diazetine, pyrrole, dihydropyrrole, imidazole, 4,5-dihydroimidazole, pyrazole, 4,5-dihydropyrazole, 1,2,3-triazole, 1,2,4-triazole, tetrazole, oxazole, 4,5-dihydrooxazole, isoxazole, 4,5-dihydroisoxazole, 2,3-dihydroisoxazole, 1,2,3-oxdiazole, 1,2,5-oxdiazole, thiazole, 4,5-dihydrothiazole, isothiazole, 1,2,3-thiadiazole, 1,2,4-thiadiazole, 1,3,4-thiadiazole, pyridine, pyridazine, pyrimidine, pyrazine, 1,2,3-triazine, 1,2,4-triazine, 1,3,5-triazine, 1,2,4,5-tetrazine, 2H-1,2-oxazine, 4H-1,2-oxazine, 6H-1,2-oxazine, 2H-1,3-oxazine, 4H-1,3-oxazine, 5,6-dihydro-4H-1,3-oxazine, 6H-1,3-oxazine, 2H-1,4-oxazine, 4H-1,4-oxazine, 2H-1,3-thiazine, 4H-1,3-thiazine, 5,6-dihydro-4H-1,3-thiazine, 6H-1,3-thiazine, 2H-1,4-thiazine, 4H-1,4-thiazine and the like. The "5- to 6-membered unsaturated heterocyclyl group containing at least one nitrogen atom" is further preferred, for example, pyrrole, dihydropyrrole, imidazole, 4,5-dihydroimidazole, pyrazole, 4,5-dihydropyrazole, 1,2,3-triazole, 1,2,4-triazole, tetrazole, oxazole, 4,5-dihydrooxazole, isoxazole, 4,5-dihydroisoxazole, 2,3-dihydroisoxazole, 1,2,3-oxdiazole, 1,2,5-oxdiazole, thiazole, 4,5-dihydrothiazole, isothiazole, 1,2,3-thiadiazole, 1,2,4-thiadiazole, 1,3,4-thiadiazole, pyridine, pyridazine, pyrimidine, pyrazine and the like.

In an embodiment of the present invention, the following compounds are even further preferred:

| Compound | Structural formula | Chemical name |
|---|---|---|
| 1 | | (R)-2-[[7-(3-aminopiperidin-1-yl)-3-methyl-2-oxo-2,3-dihydro-1H-imidazo[4,5-b]pyridin-1-yl]methyl]benzonitrile |
| 2 | | (R)-2-[[7-(3-aminopiperidin-1-yl)-3-isopropyl-2-oxo-2,3-dihydro-1H-imidazo[4,5-b]pyridin-1-yl]methyl]benzonitrile |
| 3 | | (R)-1-(2-fluorobenzyl)-7-(3-aminopiperidin-1-yl)-3-methyl-1H-imidazo[4,5-b]pyridine-2(3H)-one |
| 4 | | (R)-1-(2,5-difluorobenzyl)-7-(3-aminopiperidin-1-yl)-3-methyl-1H-imidazo[4,5-b]pyridine-2(3H)-one |
| 5 | | (R)-1-(2-chlorobenzyl)-7-(3-aminopiperidin-1-yl)-3-methyl-1H-imidazo[4,5-b]pyridine-2(3H)-one |

| Compound | Structural formula | Chemical name |
|---|---|---|
| 6 | | (R)-2-[[3-methyl-7-[3-(methylamino)piperidin-1-yl]-2-oxo-2,3-dihydro-1H-imidazo[4,5-b]pyridin-1-yl]methyl]benzonitrile |
| 7 | | (R)-2-[[7-(3-aminopiperidin-1-yl)-3,3-dimethyl-2-oxo-2,3-dihydro-1H-pyrrolo[3,2-b]pyridin-1-yl]methyl]benzonitrile |
| 8 | | (R)-4-[[7-(3-aminopiperidin-1-yl)-3-methyl-2-oxo-2,3-dihydro-1H-pyrrolo[4,5-b]pyridin-1-yl]methyl]benzonitrile |
| 9 | | (R)-3-[[7-(3-aminopiperidin-1-yl)-3-methyl-2-oxo-2,3-dihydro-1H-pyrrolo[4,5-b]pyridin-1-yl]methyl]benzonitrile |
| 10 | | (R)-2-[[7-(3-aminopiperidin-1-yl)-3-methyl-2-oxo-2,3-dihydro-1H-imidazo[4,5-b]pyridin-1-yl]methyl]-5-chlorobenzonitrile |

-continued

| Compound | Structural formula | Chemical name |
|---|---|---|
| 11 | | (R)-2-[[7-(3-aminopiperidin-1-yl)-2-oxo-oxazolo[5,4-b]pyridine-1(2H)-yl]methyl]benzonitrile |
| 12 | | (R)-2-[[7-(3-aminopyrrolidin-1-yl)-3-methyl-2-oxo-2,3-dihydro-1H-imidazo[4,5-b]pyridin-1-yl]methyl]benzonitrile |
| 13 | | (R)-2-[[7-(3-aminopiperidin-1-yl)-3-methyl-2-thio-2,3-dihydro-1H-imidazo[4,5-b]pyridin-1-yl]methyl]benzonitrile |
| 14 | | 2-[[7-(1,4-homopiperazin-1-yl)-3-methyl-2-oxo-2,3-dihydro-1H-imidazo[4,5-b]pyridin-1-yl]methyl]benzonitrile |
| 15 | | 2-[[7-(3-aminohomopiperidin-1-yl)-3-methyl-2-oxo-2,3-dihydro-1H-imidazo[4,5-b]pyridin-1-yl]methyl]benzonitrile |

-continued

| Compound | Structural formula | Chemical name |
|---|---|---|
| 16 | | (R)-2-[[7-(3-aminopiperidin-1-yl)-3-methyl-2-oxo-2,3-dihydro-1H-imidazo[4,5-b]pyridin-1-yl]methyl]naphthonitrile |
| 17 | | (R)-2-[[7-(3-aminopiperidin-1-yl)-3,5-dimethyl-2-oxo-2,3-dihydro-1H-imidazo[4,5-b]pyridin-1-yl]methyl]benzonitrile |
| 18 | | (R)-2-[[9-(3-aminopiperidin-1-yl)-3-methyl-2-oxo-2,3-dihydro-1H-imidazo[4,5-b]quinolin-1-yl]methyl]benzonitrile |
| 19 | | (R)-2-[[7-(3-aminopiperidin-1-yl)-2-oxo-2,3-dihydro-1H-imidazo[4,5-b]pyridin-1-yl]methyl]benzonitrile |
| 20 | | 2-[[7-(3-aminoazetidin-1-yl)-3-methyl-2-oxo-2,3-dihydro-1H-imidazo[4,5-b]pyridin-1-yl]methyl]benzonitrile |

-continued

| Compound | Structural formula | Chemical name |
| --- | --- | --- |
| 21 | | (R)-2-[[7-(3-aminopyrrolidin-1-yl)-3,5-dimethyl-2-oxo-2,3-dihydro-1H-imidazo[4,5-b]pyridin-1-yl]methyl]benzonitrile |
| 22 | | (R)-2-[[(7-(3-aminopiperidin-1-yl)-5-chloro-3-methyl-2-oxo-2,3-dihydro-1H-imidazo[4,5-b]pyridin-1-yl]methyl]benzonitrile |
| 23 | | (R)-2-[[7-(3-aminopiperidin-1-yl)-5-(dimethylamino)-3-methyl-2-oxo-2,3-dihydro-1H-imidazo[4,5-b]pyridin-1-yl]methyl]benzonitrile |
| 24 | | 2-[[3-methyl-2-oxo-7-(piperazin-1-yl)-2,3-dihydro-1H-imidazo[4,5-b]pyridin-1-yl]methyl]benzonitrile |
| 25 | | (R)-2-[[7-(3-aminopiperidin-1-yl)-5-ethyl-3-methyl-2-oxo-2,3-dihydro-1H-imidazo[4,5-b]pyridin-1-yl]methyl]benzonitrile |

-continued

| Compound | Structural formula | Chemical name |
|---|---|---|
| 26 | | (R)-2-[[7-(3-aminopiperidin-1-yl)-3-ethyl-5-methyl-2-oxo-2,3-dihydro-1H-imidazo[4,5-b]pyridin-1-yl]methyl]benzonitrile |
| 27 | | (R)-N-(1-(1-(2-cyano-benzyl)-3,5-dimethyl-2-oxo-2,3-dihydro-1H-imidazo[4,5-b]pyridin-7-yl)piperidin-3-yl)acetamide |
| 28 | | (R)-2-[[7-(3-aminopiperidin-1-yl)-5-methyl-2-oxo-2,3-dihydro-1H-imidazo[4,5-b]pyridin-1-yl]methyl]benzonitrile |
| 29 | | (R)-2-((7-(3-aminopiperidin-1-yl)-5-(hydroxymethyl)-3-methyl-2-oxo-2,3-dihydro-1H-imidazo[4,5-b]pyridin-1-yl)methyl)benzonitrile |
| 30 | | (R)-7-(3-aminopiperidin-1-yl)-1-(2-cyanobenzyl)-3-methyl-2-oxo-2,3-dihydro-1H-imidazo[4,5-b]pyridin-5-carboxylic acid |

| Compound | Structural formula | Chemical name |
|---|---|---|
| 31 | | (R)-7-[3-(2-cyano-benzyl)aminopiperidin-1-yl]-1-(2-cyano-benzyl)-3,5-dimethyl-2-oxo-2,3-dihydro-1H-imidazo[4,5-b]pyridine |

Also provided is a process for preparation of the above compounds, which involves the following chemical reactions, but not limited to the following process:

When Y is O:

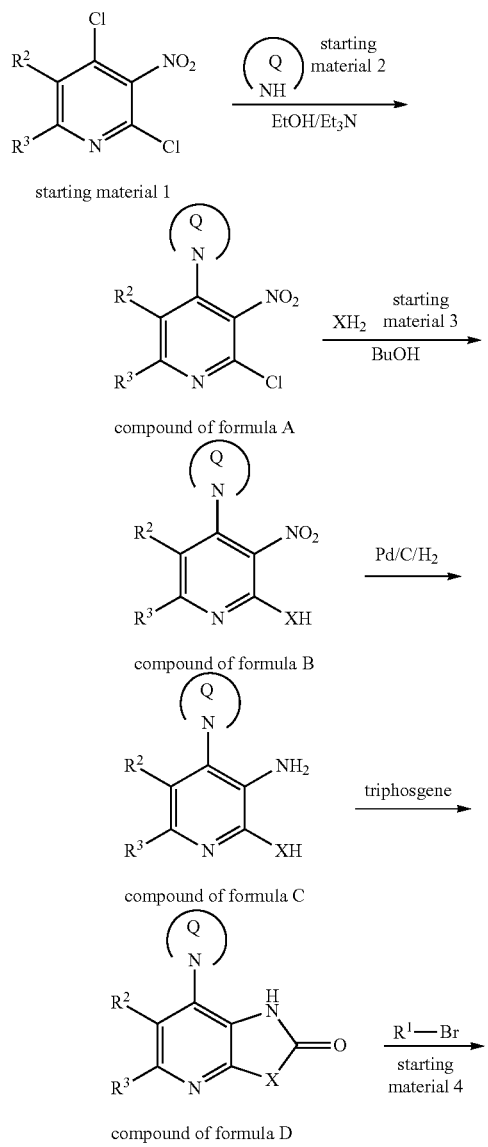

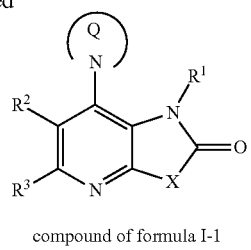

compound of formula I-1

Step 1 the Preparation of a Compound of Formula A

Ethanol, starting material 1, starting material 2 and triethylamine are added in a dry reaction bottle, stirred at room temperature, and dried under a reduced pressure to yield the compound of formula A as yellow solid.

Step 2 the Preparation of a Compound of Formula B

The compound of formula A is added in a dry reaction bottle, and dissolved in butanol. A solution of methylamine in ethanol is added, and stirred at a high temperature. The reaction solution is dried under a reduced pressure to yield the compound of formula B as yellow solid.

Step 3 the Preparation of a Compound of Formula C

The compound of formula B is added in a dry reaction bottle, and dissolved in methanol. Pd—C is added at room temperature, into which hydrogen gas is introduced, and stirred. The reaction solution is filtered off, dried under vacuum, and purified through a column chromatography to yield the compound of formula C.

Step 4 the Preparation of a Compound of Formula D

Triphosgene and triethylamine are added in a dry reaction bottle, dissolved in tetrahydrofuran. The compound of formula C is added at a low temperature, dissolved in tetrahydrofuran, and stirred. The reaction solution is exacted by ethyl acetate, and washed by saturated solution of sodium carbonate and saturated saline solution. The organic layer is dried over anhydrous sodium sulfate, and purified through a column chromatography to yield the compound of formula D.

Step 5 the Preparation of a Compound of Formula I-1

The compound of formula D is added in a dry reaction bottle, dissolved in DMF (N,N-dimethyl formamide), into which starting material 4 and potassium carbonate are dropped at a low temperature, and stirred at room temperature for reaction. The reaction solution is exacted by ethyl acetate, and washed by a saturated solution of sodium chloride. The organic layer is dried over anhydrous sodium sulfate, and purified through a column chromatography to yield the compound of formula I-1.

$R^1$, $R^2$, $R^3$, Q and X in the above chemical reactions are as defined above.

When Y is S:

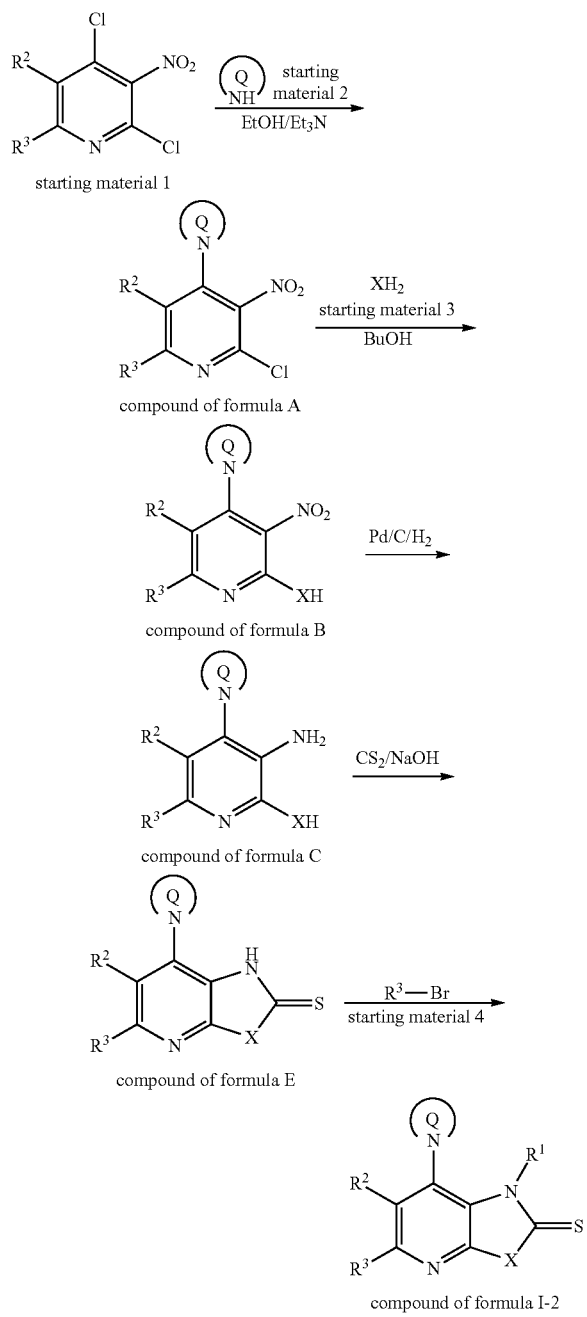

Steps 1-3 are same as the reaction Steps 1-3 when Y is O,

Step 4 the Preparation of a Compound of Formula E $CS_2$ and NaOH are dissolved in ethanol, into which the compound of formula C is added, stirred for 1 to 3 days at a high temperature, diluted by adding ethyl acetate, and washed sequentially by using $NH_4Cl$, $H_2O$, and saline solution. The organic layer is dried over $Na_2SO_4$, and spinned to dryness to yield the compound of formula E.

Step 5 is same as reaction Step 5 when Y is O.

When Y is $NR^7$, the preparation process is performed in accordance with the preparation process when Y is O or Y is S.

The pharmaceutically acceptable salts of any of the above compounds of the present invention refer to the salts prepared by pharmaceutically acceptable, non-toxic bases or acids, including salts of organic acids, inorganic acids, organic bases, and inorganic bases. The organic acids include formic acid, acetic acid, benzenesulfonic acid, benzoic acid, p-toluene sulfonic acid, (2R,3R)-2,3-dihydroxysuccinic acid, camphor sulfonic acid, citric acid, methanesulfonic acid, ethanesulfonic acid, propanesulfonic acid, fumaric acid, gluconic acid, glutamic acid, isethionic acid, lactic acid, maleic acid, malic acid, mandelic acid, mucic acid, pamoic acid, pantothenic acid, succinic acid, tartaric acid and the like, with benzoic acid, benzenesulfonic acid, p-toluene sulfonic acid, citric acid, maleic acid, fumaric acid, and tartaric acid are particularly preferred. The inorganic acids include hydrobromic acid, hydrochloric acid, nitric acid, sulphuric acid, phosphoric acid and the like, with hydrobromic acid, hydrochloric acid, sulphuric acid, and phosphoric acid are particularly preferred. The organic bases include primary, secondary and tertiary amine, substituted amine including naturally occurring substituted amine, cyclic amine and basic ion exchange resins, selected from arginine, betaine, caffeine, choline, N,N'-dibenzylethylenediamine, diethylamine, 2-diethylamino ethanol, 2-dimethylamino ethanol, ethanolamine, ethylenediamine, N-ethyl-morpholine, N-ethylpiperidine, meglumine, glucosamine, histidine, hydrabamine, isopropylamine, lysine, methylglucamine, morpholine, piperazine, piperidine, polyacyl resin, procaine, purine, theobromine, triethylamine, trimethylamine, tripropylamine, trometamol and the like. The inorganic bases include the basic compounds of ammonium, lithium, sodium, potassium, calcium, magnesium, zinc, barium, aluminum, ferric, copper, ferrous, manganese, manganous (bivalent) and the like, with the basic compounds of ammonium, lithium, sodium, potassium, calcium, magnesium, zinc, and barium are particularly preferred. The salts in a form of solid can be present in one or more crystalline structures, and also can be present in a form of solvated compound, for example, a hydrate.

The products obtained in the examples are mostly in the form of pharmaceutically acceptable salts. Those skilled in the art can convert them into free bases or further convert into other pharmaceutically acceptable salts through conventional means in the art.

The compound of the present invention contains one or more asymmetric centers, and thus can exist in the form of racemates and mixtures of racemates, a single enantiomer, mixtures of diastereomers, and a single diastereomer. The compound of the present invention has asymmetric center(s), each of which can independently afford two optical isomers. All possible optical isomers and mixtures of diastereomers, and pure or partly pure compounds fall within the scope of the present invention. The present invention includes all stereoisomers of these compounds.

If the compound described herein contains alkenyl double bond(s), the present invention includes the cis isomers and trans isomers, unless otherwise specified.

The compound of the present invention can exist in the form of a tautomer, which has different connection sites for hydrogen via one or more double-bond shifts. For example, the ketone and its enol form are ketone-enol tautomer. The tautomers and mixtures thereof are included in the compounds of the invention.

The compounds represented by general formula (I), their pharmaceutically acceptable salts, and stereoisomers thereof can be forms of solvates. In the event that the solvate is a hydrate, the hydration can be accomplished during the preparation procedures or can be gradually accomplished by virtue of the moisture absorption of the initial compounds.

The compounds of the present invention may be used in combination with one or more other drugs. The combination would be safer or more effective than a single drug. Such other drugs may be administered, by a route and in an amount commonly used, contemporaneously or sequentially with a compound of Formula (I). When administrated contemporaneously, a pharmaceutical composition in unit dosage form containing such other drugs and a compound of Formula (I) is preferred. Examples of other active ingredients that may be administered in combination with a compound of Formula (I), and either administered separately or in the same pharmaceutical composition, include, but are not limited to:

(a) other dipeptidyl peptidase-IV inhibitors;

(b) insulin sensitizers, including: (i) PPARγ agonists such as the glitazones (e.g. troglitazone, pioglitazone, englitazone, MCC-555, rosiglitazone, and the like), and other PPAR ligands, including PPARα/γ dual agonists, such as KRP-297, and PPARα agonists such as fenofibric acid derivatives (gemfibrozil, clofibrate, fenofibrate and benzafibrate); (ii) biguanides such as metformin and phenformin; (iii) protein tyrosine phosphatase-1B (PTP-1B) inhibitors;

(c) insulin or insulin mimetics;

(d) sulfonylureas and other insulin secretagogues such as tolbutamide and glipizide, meglitinide or related drugs;

(e) α-glucosidase inhibitors (such as acarbose);

(f) glucagon receptors antagonists;

(g) GLP-1, GLP-1 mimetics and GLP-1 receptor agonists;

(h) GLP, GLP mimetics and GLP receptor agonists;

(i) PACAP, PACAP mimetics and PACAP receptor δ agonists;

(j) cholesterol lowering agents such as (i) HMG-CoA reductase inhibitors (lovastatin, simvastatin, pravastatin, fluvastatin, atorvastatin, rivastatin, itavastatin, rosuvastatin and other statins), (ii) sequestrants (cholestyramine, colestipol, and dialkylaminoalkyl derivatives of a cross-linked dextran), (iii) nicotinyl alcohol, nicotinic acid or salts thereof, (iv) PPARα agonists such as fenofibric acid derivatives (gemfibrozil, clofibrate, fenofibrate and benzafibrate), (v) PPARα/γ dual agonists, such as KRP-297, (vi) inhibitors of cholesterol absorption, such as beta-sitosterol and ezetimibe, (vii) acetyl CoA, cholesterol acyltransferase inhibitors, such as avasimibe, and (viii) anti-oxidants, such as probucol;

(k) PPARδ agonists;

(l) antiobesity compounds such as fenfluramine, dexfenfluramine, phentiramine, sibutramine, orlistat, neuropeptide Y5 inhibitors, and β3 adrenergic receptor agonists;

(m) an ileal bile acid transporter inhibitor; and (n) agents intended for use in inflammatory conditions such as aspirin, non-steroidal anti-inflammatory drugs, glucocorticoids, azulfidine, and cyclo-oxygenase II selective inhibitors.

The combinations as described above involve combinations of a compound of the present invention not only with one other active compound but also with two or more other active compounds. Non-limited examples include combinations of compounds having formula (I) with two or more active compounds selected from biguanides, sulfonylureas, HMG-CoA reductase inhibitors, PPAR agonists, PTP-1B inhibitors, other DPP-IV inhibitors and antiobesity compounds.

The weight ratio of the compounds of the invention to a second active ingredient can vary, depending on the effective doses of each component. In general, the respective effective dose would be used. Therefore, for example, when the compounds of the invention are combined with other drugs, the weight ratio of the present compounds to other drugs usually is about 1000:1 to about 1:1000, preferably about 200:1 to about 1:200. The combination of the compounds of the present invention and other active ingredients generally has the weight ratio within the above range, but in each case, the effective dose of each active ingredient should be used.

The present invention further seeks to protect a pharmaceutical composition comprising any compound as described above, its pharmaceutically acceptable salts, stereoisomers or solvates thereof and one or more pharmaceutically acceptable carriers and/or diluents, which may be any clinically or pharmaceutically acceptable dosage form, preferably oral formulation or injection formulation. 1 mg-100 mg, a physiologically effective amount of compounds represented by general formula (I) is comprised therein. For example, the amount of the active ingredient may be 1 mg, 5 mg, 10 mg, 15 mg, 20 mg, 25 mg, 50 mg, 75 mg, 100 mg and the like. The said compounds can be administered 1 to 4 times every day, preferably once or twice every day.

Any compound of the present invention, its pharmaceutically acceptable salts, and stereoisomers or solvates thereof can be orally administrated to patients in need of such a therapy.

Any compound of the present invention, its pharmaceutically acceptable salts, and stereoisomers or solvates thereof can be formulated into a conventional solid formulation, such as a tablet, capsule, pill, granule, etc.; also can be formulated into an oral liquid formulation, such as an oral solution, oral suspension, syrup, etc. The tablets refer to a solid dosage form including round sheet or abnormally shaped sheet prepared by pressing the homogeneous mixture of the drugs and suitable adjuvants, mainly are ordinary oral tablets, otherwise include buccal tablets, sublingual tablets, oral patch, chewable tablets, dispersible tablets, soluble tablets, effervescent tablets, sustained-release tablets, controlled-release tablets and enteric-coated tablets and the like. The capsules refer to a solid dosage form prepared as follows: drugs or together with added adjuvants are filled into hollow capsules or sealed in a soft capsule materials; according to the dissolution and release characteristics, the capsules can be classified into hard gelatin capsules (generally known as the capsules), soft capsules (soft gelatin capsules), sustained-release capsules, controlled-release capsules and enteric-coated capsules etc. The pills refer to a sphere or sphere-like solid dosage form which is prepared in a proper manner by drugs uniformly mixed with the appropriate adjuvants, including drop pills, sugar coated pills, pellets, etc. The granules refer to a dry granular formulation having a certain particle size prepared by drugs together with the appropriate adjuvants, and can be classified into soluble granules (commonly known as granules), suspended granules, effervescent granules, enteric-coated granules, sustained-release granules and controlled-release particles, etc. The oral solution refers to a clear solution formulation for oral administration prepared by dissolving the drug in a suitable solvent. The oral suspension refers to the suspension formulation for oral administration prepared by dispersing the insoluble solid drug in a liquid medium, including dry suspension or concentrated suspension. The syrup refers to a concentrated sucrose solution containing drugs.

When an oral formulation is prepared, suitable fillers, binders, disintegrating agents, lubricants, and the like can be added. The commonly used fillers include starch, powdered sugar, calcium phosphate, calcium sulfate dihydrate, dextrin, microcrystalline cellulose, lactose, pregelatinized starch, mannitol, etc.; the commonly used binders include sodium carboxymethyl cellulose, PVP-K30, hydroxypropyl cellulose, starch slurry, methyl cellulose, ethyl cellulose, hydroxypropylmethyl cellulose, gelling starch, etc.; the commonly used disintegrating agents include dry starch, cross-linked povidone, cross-linked sodium carboxymethyl cellulose, sodium carboxymethyl starch, lower substituted hydroxypropyl cellulose, etc.; and the commonly used lubricants include magnesium stearate, talc, dodecyl sodium sulfate, silica powder, etc.

Dipeptidyl peptidase-IV (DPP-IV) is a cell surface protein involved in a variety of biological functions. It has a broad tissue distribution (intestine, kidney, liver, pancreas, placenta, thymus gland, spleen, epithelial cells, vascular endothelium, lymph and myelocyte, serum) and a clear tissue- or cell-type expression level. DPP-IV is identified as T type cell activation marker, CD26, and it can cleave a great number of immune-regulated, endocrinic and neurological peptides in vitro, indicating that this peptidase has a potential function in a variety of disease courses in the human or other animals.

Pharmacological experiments show that the DPP-IV inhibitors can significantly inhibit the activity of DPP-IV, protect the activity of GLP-1, stimulate the secretion of insulin, reduce postprandial glucagon level, lower blood glucose, and improve glucose tolerance; and they have the function for protecting GIP activity, can increase the concentration of GIP and enhance the effect of stimulating the secretion of insulin; and DPP-IV inhibitors can also improve metabolism of glucose and lipid and prevent weight gain.

The present invention also provides the use of the new DPP-IV inhibitors in the manufacture of the medicine for the treatment and/or prevention of the following diseases:

Type II diabetes and related diseases, since it has been sufficiently determined that GLP-1 and GIP can be rapidly inactivated by DPP-IV in vivo, the DPP-IV inhibitors of the present invention can be used to treat type II diabetes and treat and/or prevent a number of conditions complicated with type II diabetes, including metabolic syndrome X, reactive hypoglycemia and diabetic dyslipidemia. The following diseases, conditions and symptoms are relevant with type II diabetes, and thus, they can be treated, controlled or prevented in some conditions by the therapy involving the compounds of the present invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high HDL levels, (12) atherosclerosis and its sequelaes, (13) vascular restenosis, (14) irritable bowel syndrome (15) colitis, including crohn's disease and ulcerative colitis, (16) retinopathy, (21) nephropathy, (22) neuropathy, (23) X syndrome, (24) ovarian hyperandrogenism (polycystic ovarian syndrome) and other diseases having insulin resistance; as well as growth hormone deficiency, intestinal damage, immunosuppression, HIV infection, the generation of blood cells, neuron disease, invasion and metastasis of a brain tumor, benign prostatic hyperplasia, semen mobility, gingivitis, osteoporosis and the like.

Hereafter, the beneficial effect of the compounds of the present invention is further described through pharmacological experiments in vitro. However, it should not be understood that the compounds of the present invention only have the following beneficial effect.

EXPERIMENTAL EXAMPLE

The pharmacological activity in vitro of the compounds of the present invention

Testing Compounds:

A part of the compounds of the present invention, prepared by the applicant, their chemical names and structural formulas are as described above.

Experimental Methods:

The preparation of the reaction solution DPPIV-Glo® buffer should be thawed in advance. The freeze-dried fluorescein should be taken out of the refrigerator in advance and left to room temperature. The DPPIV-Glo® substrate was dissolved in 110 µl water, and mixed thoroughly by votex as a stock solution (the concentration is 10 mmol). The fluorescein was added into an ampoule containing 50 mL DPPIV-Glo™ buffer. Then, 100 µl solution containing DPPIV-Glo™ substrate was mixed with 50 mL DPPIV-Glo™ buffer containing a fluorescein to afford the reaction solution, which needs to be stored in a refrigerator at −20° C.

1. The inhibition to DPP-IV was measured by a fluorescence assay:

In the assay of DPP-IV enzyme, the total volume of each well was 25 µl, including 12 µl solution (66 pM DPP-4 dissolved in 10 mmol trihydroxymethylaminomethane buffer, pH=7.5), 0.5 µl compound (dissolved in DMSO), and 12.5 µl reaction solution. All of the compounds were 10-fold diluted by DMSO before the experiment, and each compound needs to be diluted to 8 concentrations. Before the experiment, the solution containing DPP-IV enzyme was incubated with the mixture of compounds for 10 min at RT. And then, the reaction solution was added and incubated for 30 min. The enzyme was not added to the negative control group. The fluorescence signal was assayed after 30 min. All of the compounds were assayed twice.

2. The inhibition to DPP-8 was measured by a fluorescence assay:

In the assay of DPP-8 enzyme, the total volume of each well was 25 µl, including 12 µl solution (111.9 pM DPP-8 dissolved in 10 mmol trihydroxymethylaminomethane buffer, pH=7.5), 0.5 µl compound (dissolved in DMSO), and 12.5 µl reaction solution. All of the compounds were 10-fold diluted by DMSO before the experiment, and each compound needs to be diluted to 8 concentrations. Before the experiment, the solution containing DPP-8 enzyme was incubated with the mixture of compounds for 10 min at RT. And then, the reaction solution was added and incubated for 30 min. The enzyme was not added to the negative control group. The fluorescence signal was assayed after 30 min. All of the compounds were assayed twice.

3. The inhibition to DPP-9 was measured by a fluorescence assay:

In the assay of DPP-9 enzyme, the total volume of each well was 25 µl, including 12 µl solution (26 pM DPP-9 dissolved in 10 mmol trihydroxymethylaminomethane buffer, pH=7.5), 0.5 µl compound (dissolved in DMSO), and 12.5 µl reaction solution. All of the compounds were 10-fold diluted by DMSO before the experiment, and each compound needs to be diluted to 8 concentrations. Before the experiment, the solution containing DPP-9 enzyme was incubated with the mixture of compounds for 10 min at RT. And then, the reaction solution was added and incubated for 30 min. The enzyme was not added to the negative control group. The fluorescence signal was assayed after 30 min. All of the compounds were assayed twice.

Experiment Results and Discussion:

TABLE 1 the activity of the compounds of the present invention

| Compounds | IC$_{50}$(nM) | | |
|---|---|---|---|
| | DPP-IV | DPP-8 | DPP-9 |
| 1 | 15.6 | >100000 | >100000 |
| 2 | 479 | >100000 | >100000 |
| 3 | 2477 | >100000 | >100000 |
| 4 | 545 | >100000 | >100000 |
| 5 | 134 | >100000 | >100000 |
| 6 | 429 | >100000 | >100000 |
| 11 | 76 | >100000 | >100000 |
| 12 | 22 | >100000 | >100000 |
| 15 | 524.8 | >100000 | >100000 |
| 17 | 8.9 | >100000 | >100000 |
| 18 | 1140 | >100000 | >100000 |
| 19 | 44.5 | >100000 | >100000 |
| 21 | 11.2 | >100000 | >100000 |
| 22 | 10 | >100000 | >100000 |
| 23 | 22.9 | >100000 | >100000 |
| 25 | 19.3 | >100000 | >100000 |
| 26 | 56.9 | >100000 | >100000 |
| 29 | 13.5 | >100000 | >100000 |
| 30 | 7.9 | >100000 | >100000 |
| 31 | 421.7 | >100000 | >100000 |

As it is seen from Table 1, all of the compounds of the present invention have an excellent inhibition activity to DPP-IV, but have no inhibition to DPP-8 and DPP-9 even at 100000 nM, and have a high selectivity for DPP-IV. The compounds of the present invention are safe and efficacious.

Specific Embodiments

The following specific embodiments in the form of examples are provided to further illustrate the invention in detail, and are not to be construed as limiting the scope of the invention as described above to the following examples. All of the technical solutions achieved according to the above disclosure of the invention are within the scope of the invention.

Example 1

The preparation of (R)-2-[[7-(3-aminopiperidin-1-yl)-3-methyl-2-oxo-2,3-dihydro-1H-imidazo[4,5-b]pyridin-1-yl]methyl]benzonitrile (Compound 1) trifluoroacetate

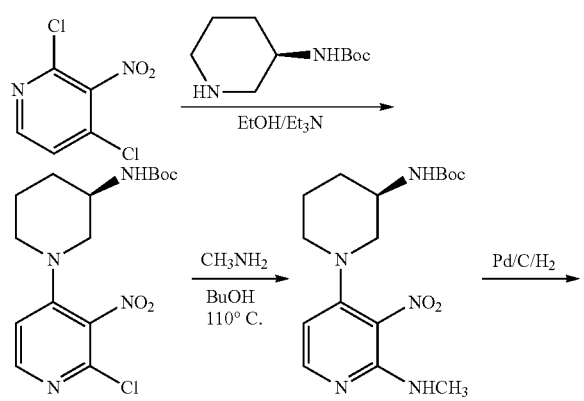

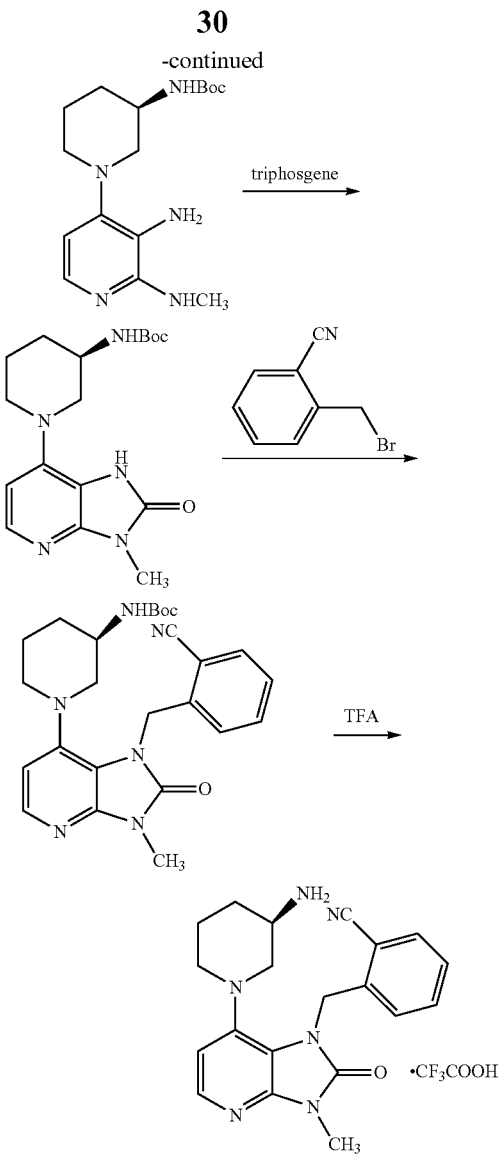

(1) (R)-1-(2-chloro-3-nitropyridin-4-yl)piperidin-3-yl tert-butyl carbamate

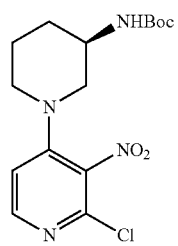 [SMILES: CC(C)(C)OC(=O)N[C@@H]1CCCN(c2ccnc(Cl)c2[N+](=O)[O-])C1]

In a dry reaction bottle, 8 mL ethanol, 579 mg 2,4-dichloro-3-nitropyridine (3.0 mmol), 600 mg R-tert-butylpiperidin-3-yl-carbamate (3.0 mmol), and 0.63 mL triethylamine were added, and stirred for 2 h at room temperature. The reaction solution was dried under a reduced pressure to afford 1.1 g titled product as yellow solid.

(2) (R)-1-[2-(methylamino)-3-nitropyridin-4-yl]piperidin-3-yl tert-butyl carbamate

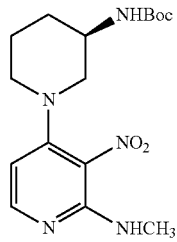 [SMILES: CNc1nccc(N2CCC[C@@H](NC(=O)OC(C)(C)C)C2)c1[N+](=O)[O-]]

In a dry reaction bottle, 1.1 g (R)-1-(2-chloro-3-nitropyridin-4-yl)piperidin-3-yl tert-butyl carbamate (3.0 mmol) was added, dissolved in 10 mL butanol, to which 10 mL 27% solution of methylamine in ethanol was added, and stirred for 24 h at 110° C. The reaction solution was dried under a reduced pressure to afford 1.0 g titled product as yellow solid.

(3) (R)-1-[3-amino-2-(methylamino)pyridin-4-yl]piperidin-3-yl tert-butyl carbamate

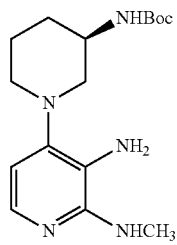 [SMILES: CNc1nccc(N2CCC[C@@H](NC(=O)OC(C)(C)C)C2)c1N]

In a dry reaction bottle, 1.0 g (R)-1-[2-(methylamino)-3-nitropyridin-4-yl]piperidin-3-yl tert-butyl carbamate (3.0 mmol) was added, dissolved in 15 mL methanol, to which 0.09 g 10% Pd—C was added at room temperature and hydrogen gas was introduced, and stirred for 3 h. The reaction solution was filtrated, dried under vacuum, and purified through a column chromatography ($CH_2Cl_2$: MeOH=25:1) to afford 600 mg red solid with a yield of 65.5%.

(4) (R)-1-(3-methyl-2-oxo-2,3-dihydro-1H-imidazo[4,5-b]pyridin-7-yl)piperidin-3-yl tert-butyl carbamate

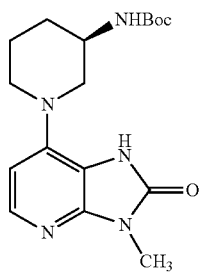 [SMILES: Cn1c(=O)[nH]c2c(N3CCC[C@@H](NC(=O)OC(C)(C)C)C3)ccnc21]

In a dry reaction bottle, 489 mg triphosgene (1.65 mmol) and 0.83 mL triethylamine (6.0 mmol) were added, and dissolved in 50 mL tetrahydrofuran, to which 0.5 g (R)-1-[3-amino-2-(methylamino)pyridin-4-yl]piperidin-3-yl tert-butyl carbamate (1-5 mmol) dissolved in 10 mL tetrahydrofuran was added at −10° C., and stirred for 0.5 h. The reaction solution was extracted with ethyl acetate, and washed with saturated sodium carbonate solution and strong brine. The organic layer was dried with anhydrous sodium sulfate, and purified through a column chromatography to afford 500 mg white powder with a yield of 92.3%.

(5) (R)-1-[1-(2-cyano-benzyl)-3-methyl-2-oxo-2,3-dihydro-1H-imidazo[4,5-b]pyridin-7-yl]piperidin-3-yl tert-butyl carbamate

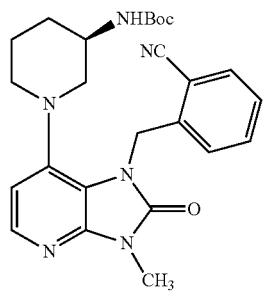 [SMILES: Cn1c(=O)n(Cc2ccccc2C#N)c2c(N3CCC[C@@H](NC(=O)OC(C)(C)C)C3)ccnc21]

In a dry reaction bottle, (R)-1-(3-methyl-2-oxo-2,3-dihydro-1H-imidazo[4,5-b]pyridin-7-yl)piperidin-3-yl tert-butyl carbamate (500 mg, 1.44 mmol) was added, and dissolved in 2 mL DMF, to which 282 mg 2-(bromomethyl)benzonitrile (1.44 mmol) and 397 mg potassium carbonate (2.88 mmol) were added dropwise at −10° C., and reacted for 1 h by stirring at room temperature. The reaction solution was extracted with ethyl acetate, and washed with saturated sodium chloride solution. The organic layer was dried with anhydrous sodium sulfate, and purified through a column chromatography (petroleum ether:ethyl acetate=1:1) to afford 200 mg white powder with a yield of 30.0%.

(6) (R)-2-[[7-(3-aminopiperidin-1-yl)-3-methyl-2-oxo-2,3-dihydro-1H-imidazo[4,5-b]pyridin-1-yl]methyl]benzonitrile trifluoroacetate

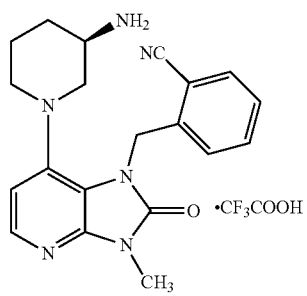 [SMILES: Cn1c(=O)n(Cc2ccccc2C#N)c2c(N3CCC[C@@H](N)C3)ccnc21 ; "·CF3COOH"]

In a dry reaction bottle, 160 mg (R)-1-[1-(2-cyanobenzyl)-3-methyl-2-oxo-2,3-dihydro-1H-imidazo[4,5-b]pyridin-7-yl]piperidin-3-yl tert-butyl carbamate (0.35 mmol) was added and dissolved in 12 mL $CH_2Cl_2$, to which 2.4 mL trifluoroacetic acid was added dropwise at 0° C., and stirred for 1 h at room temperature. The reaction solution was evaporated to dryness. The residue was dissolved in a small amount of methanol and ethyl ether to afford 110.0 mg the titled product as white solid with a yield of 87.8%.

Molecular formula: $C_{20}H_{22}N_6O$ Molecular weight: 362.43
Mass spectrum (M+H): m/z: 363.2

¹H-NMR (CDCl₃-D₂O, 600 MHz): δ 8.01 (d, 1H), 7.67 (d, 1H), 7.47 (dd, 1H), 7.34 (dd, 1H), 6.88 (d, 1H), 6.79 (d, 1H), 5.49 (s, 2H), 3.53 (s, 3H), 3.25 (m, 2H), 2.70 (m, 2H), 2.59 (m, 1H), 2.05 (m, 1H), 1.61 (m, 1H), 1.43 (m, 1H), 1.28 (m, 1H).

Example 2

The preparation of (R)-2-[[7-(3-aminopiperidin-1-yl)-3-isopropyl-2-oxo-2,3-dihydro-1H-imidazo[4,5-b]pyridin-1-yl]methyl]benzonitrile (Compound 2) trifluoroacetate

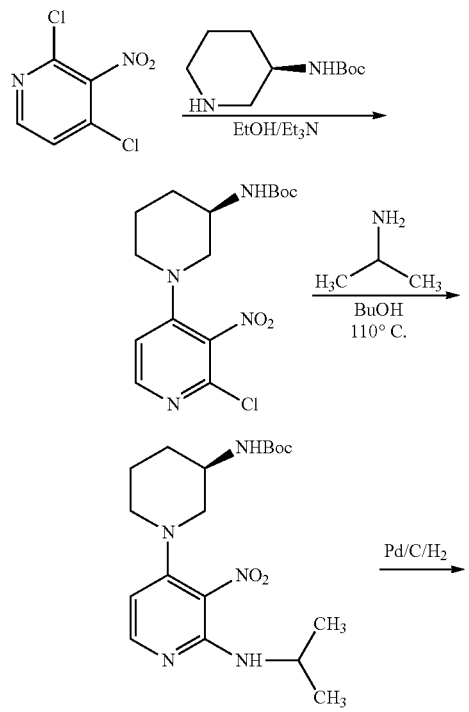

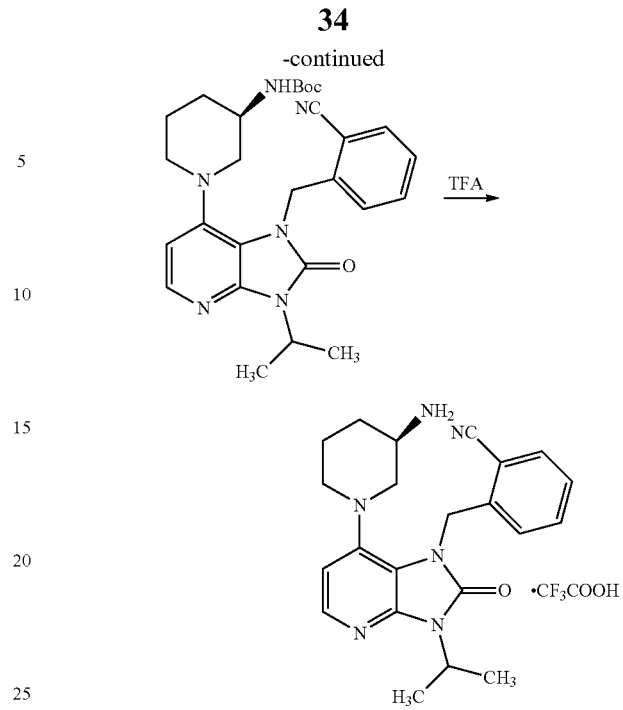

According to the above reaction scheme, the titled compound was prepared. The detailed experimental procedures and conditions could be found in Example 1. 130 mg product was obtained with a yield of 51.4%.

Molecular formula: $C_{22}H_{26}N_6O$ Molecular weight: 390.48
Mass spectrum (M+H): m/z: 391.2

¹H-NMR (d₆-DMSO-D₂O, 600 MHz): δ8.03 (d, 1H), 7.88 (d, 1H), 7.62 (t, 1H), 7.48 (t, 1H), 6.95 (d, 1H), 6.92 (d, 1H), 5.44 (d, 1H), 5.35 (d, 1H), 4.74 (m, 1H), 3.15 (d, 1H), 2.93 (s, 1H), 2.82 (d, 1H), 2.65 (d, 1H), 2.53 (m, 1H), 1.95 (d, 1H), 1.65 (d, 1H), 1.51 (d, 6H), 1.30 (m, 2H).

Example 3

The preparation of (R)-1-(2-fluorobenzyl)-7-(3-aminopiperidin-1-yl)-3-methyl-1H-imidazo[4,5-b]pyridin-2(3H)-one (Compound 3) trifluoroacetate

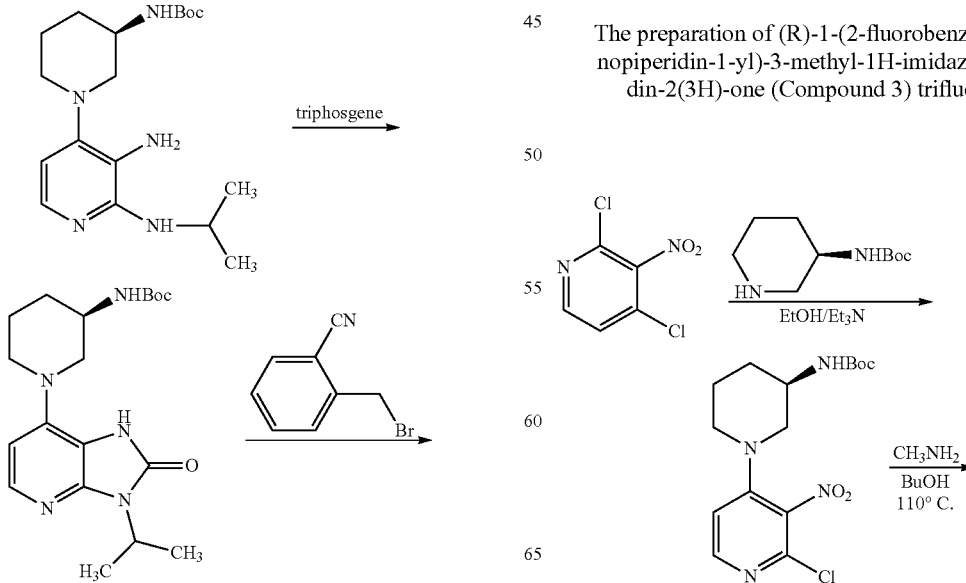

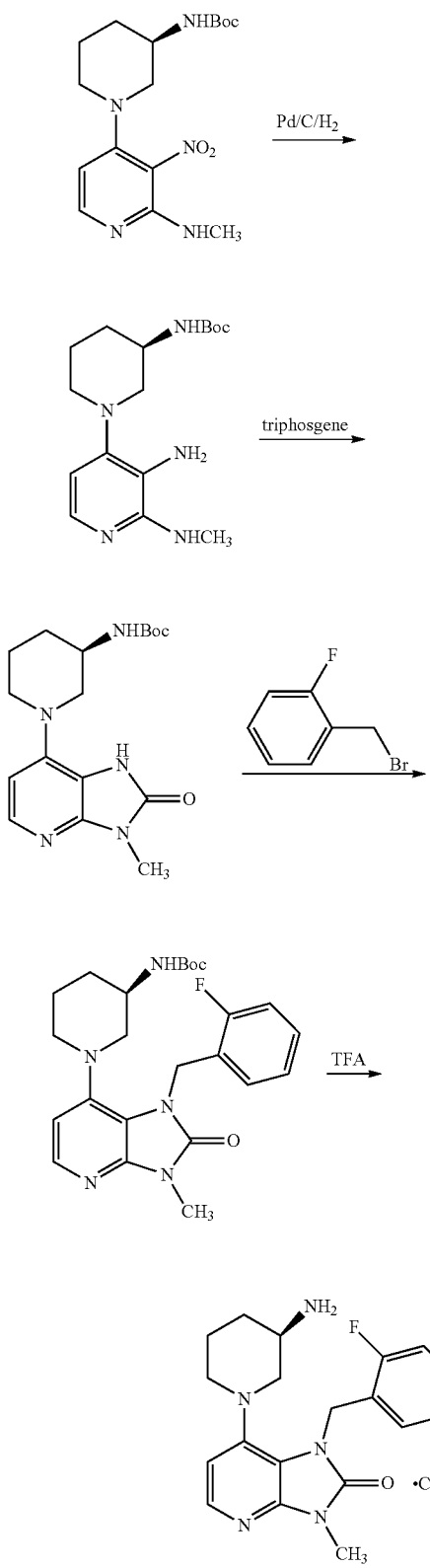

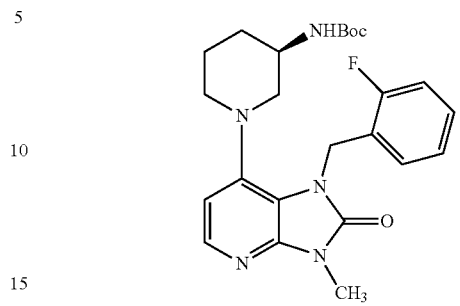

(5) (R)-1-[1-(2-fluorobenzyl)-3-methyl-2-oxo-2,3-dihydro-1H-imidazo[4,5-b]pyridin-7-yl]piperidin-3-yl tert-butyl carbamate The specific operation referred to the Step (5) described in Example 1. 347 mg (R)-1-(3-methyl-2-oxo-2,3-dihydro-1H-imidazo[4,5-b]pyridin-7-yl)piperidin-3-yl tert-butyl carbamate (1 mmol), 189 mg 1-(bromomethyl)-2-fluorobenzene (1 mmol), and 276 mg potassium carbonate (2 mmol) were charged to afford 230 mg titled product with a yield of 50.5%.

(6) (R)-1-(2-fluorobenzyl)-7-(3-aminopiperidin-1-yl)-3-methyl-1H-imidazo[4,5-b]pyridine-2(3H)-one trifluoroacetate

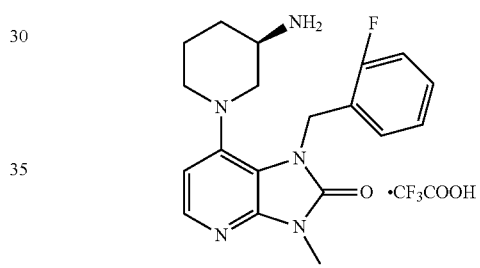

The specific operation referred to the step (6) in Example 1. 200 mg (R)-1-[1-(2-fluorobenzyl)-3-methyl-2-oxo-2,3-dihydro-1H-imidazo[4,5-b]pyridin-7-yl]piperidin-3-yl tert-butyl carbamate (0.44 mmol) and 2.4 mL trifluoroacetic acid were charged to afford 100 mg titled product with a yield of 64.10%.

Molecular formula: $C_{19}H_{22}FN_5O$ Molecular weight: 355.41 Mass spectrum (M+H): m/z: 356.2

$^1$H-NMR ($d_6$-DMSO-$D_2O$, 600 MHz): δ 7.99 (d, 1H), 7.31 (d, 1H), 7.21 (t, 1H), 7.08 (t, 1H), 6.91 (d, 1H), 6.87 (s, 1H), 5.29 (d, 1H), 5.22 (d, 1H), 3.40 (s, 3H), 3.20 (d, 1H), 3.02 (s, 1H), 2.84 (d, 1H), 2.67 (s, 1H), 2.53 (s, 1H), 1.98 (s, 1H), 1.67 (s, 1H), 1.34 (s, 2H).

Example 4

The preparation of (R)-1-(2,5-difluorobenzyl)-7-(3-aminopiperidin-1-yl)-3-methyl-1H-imidazo[4,5-b]pyridine-2(3H)-one (Compound 4) trifluoroacetate

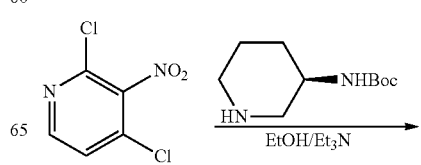

The Steps (1)-(4) were same as the Steps (1)-(4) described in the preparation example of Compound 1.

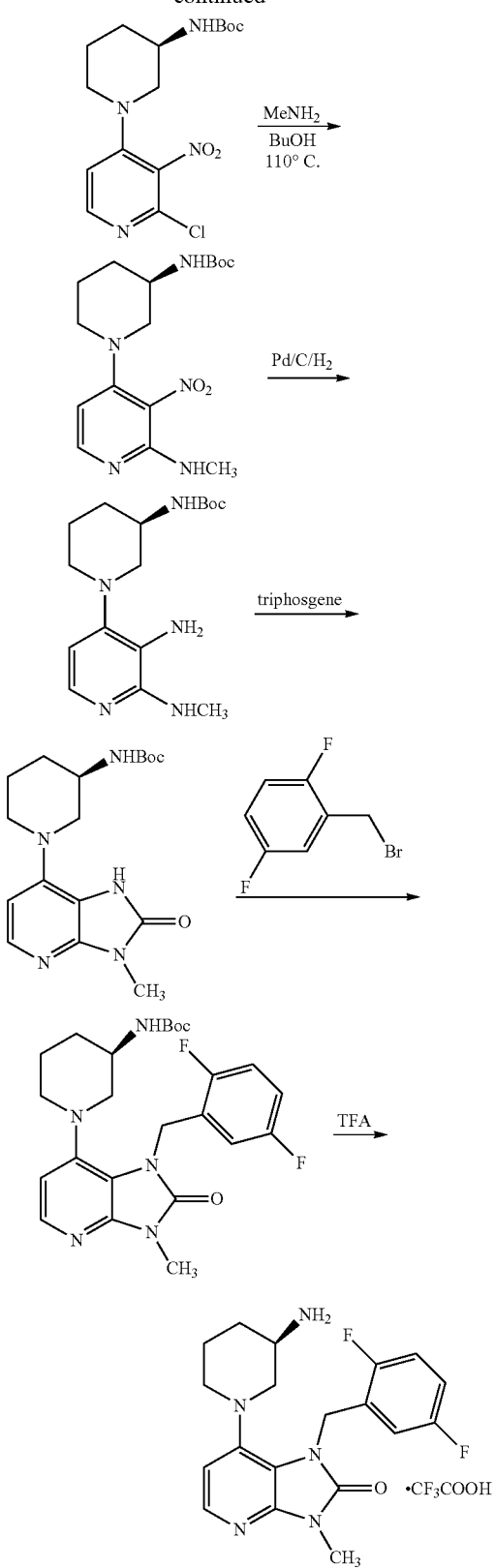

The steps (1)-(4) were same as the steps (1)-(4) described in the preparation example of Compound 1.

(5) (R)-1-[1-(2,5-difluorobenzyl)-3-methyl-2-oxo-2,3-dihydro-1H-imidazo[4,5-b]pyridin-7-yl]piperidin-3-yl carbamic acid ter.-butyl ester

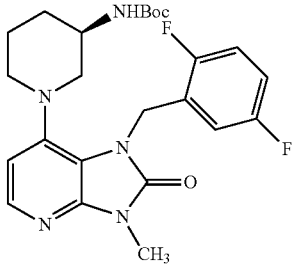 [SMILES: Cn1c(=O)n(Cc2cc(F)ccc2F)c2c(N3CCC[C@@H](NC(=O)OC(C)(C)C)C3)ccnc21]

The specific operation referred to the step (5) described in Example 1. 347 mg (R)-1-(3-methyl-2-oxo-2,3-dihydro-1H-imidazo[4,5-b]pyridin-7-yl)piperidin-3-yl carbamic acid ter.-butyl ester (1.0 mmol), 0.14 mL 2,5-difluorobenzyl bromide (1.1 mmol), and 276 mg potassium carbonate (2.0 mmol) were charged to afford 273 mg titled product with a yield of 57.7%.

(6) (R)-1-(2,5-difluorobenzyl)-7-(3-aminopiperidin-1-yl)-3-methyl-1H-imidazo[4,5-b]pyridine-2(3H)-one trifluoroacetate

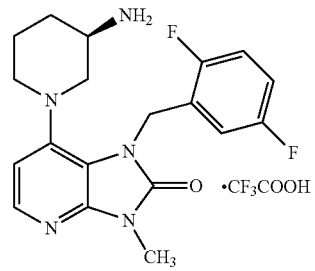 [SMILES: Cn1c(=O)n(Cc2cc(F)ccc2F)c2c(N3CCC[C@@H](N)C3)ccnc21 ; "·CF3COOH"]

The specific operation referred to the step (6) described in Example 1. 264 mg (R)-1-[1-(2,5-difluorobenzyl)-3-methyl-2-oxo-2,3-dihydro-1H-imidazo[4,5-b]pyridin-7-yl]piperidin-3-yl carbamic acid ter.-butyl ester (0.558 mmol) and 3.83 mL trifluoroacetic acid were charged to afford 161 mg titled product with a yield of 77.4%.

Molecular formula: $C_{19}H_{21}F_2N_5O$ Molecular weight: 373.4 Mass spectrum (M+H): m/z: 374.2

$^1$H-NMR ($d_6$-DMSO-$D_2$O, 600 MHz): δ 8.00 (s, 1H), 7.28 (m, 1H), 7.16 (m, 1H), 6.92 (d, 1H), 6.79 (s, 1H), 5.28 (d, 1H), 5.20 (d, 1H), 3.38 (s, 3H), 3.20 (d, 1H), 3.04 (s, 1H), 2.84 (d, 1H), 2.68 (s, 1H), 2.58 (s, 1H), 1.33 (m, 2H), 1.67 (d, 1H), 1.98 (d, 1H).

Example 5

The preparation of (R)-1-(2-chlorobenzyl)-7-(3-aminopiperidin-1-yl)-3-methyl-1H-imidazo[4,5-b]pyridine-2(3H)-one (Compound 5) trifluoroacetate

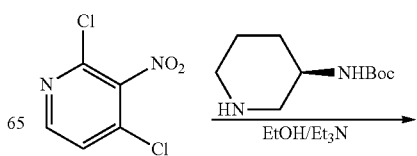

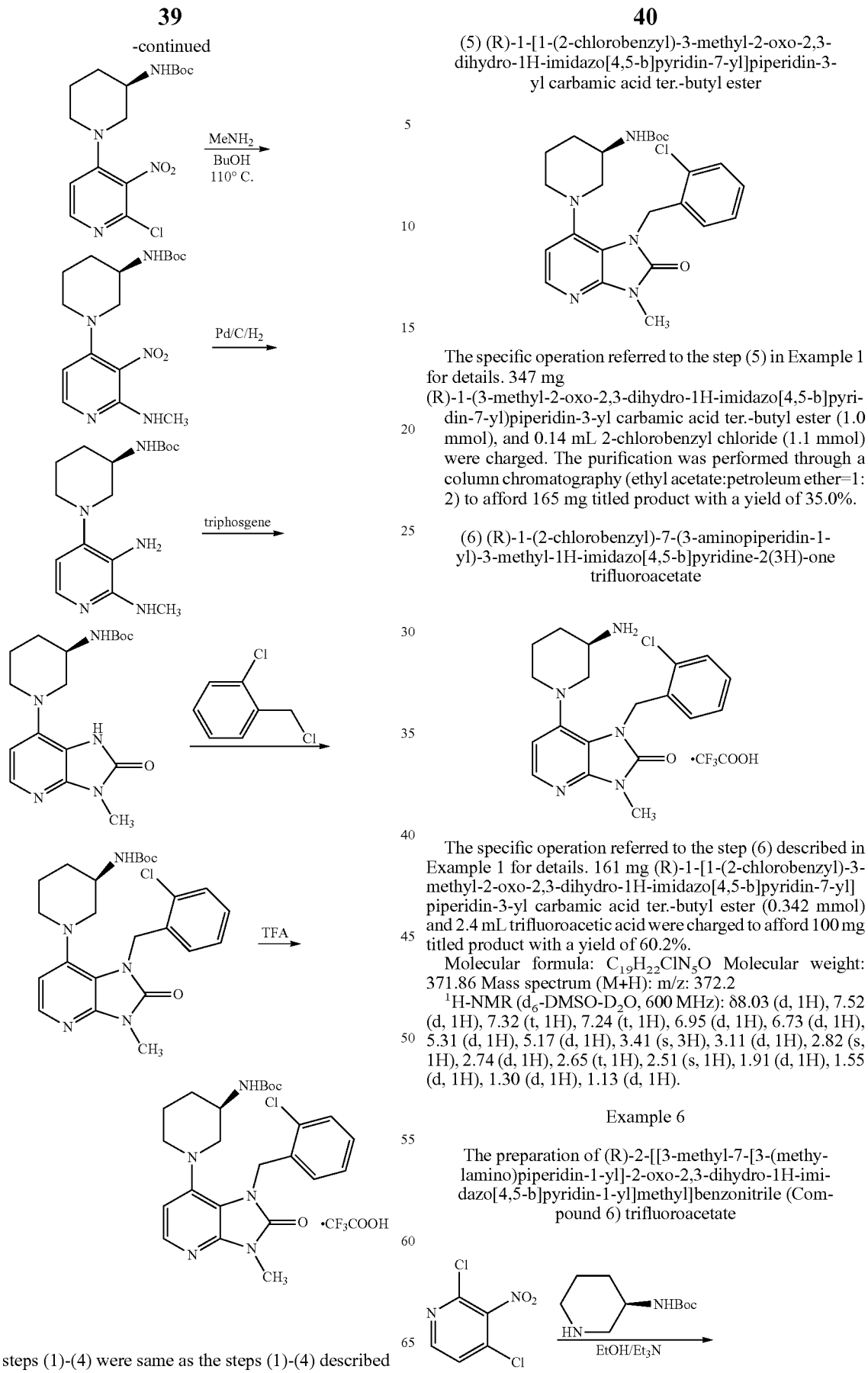

(5) (R)-1-[1-(2-chlorobenzyl)-3-methyl-2-oxo-2,3-dihydro-1H-imidazo[4,5-b]pyridin-7-yl]piperidin-3-yl carbamic acid ter.-butyl ester The specific operation referred to the step (5) in Example 1 for details. 347 mg (R)-1-(3-methyl-2-oxo-2,3-dihydro-1H-imidazo[4,5-b]pyridin-7-yl)piperidin-3-yl carbamic acid ter.-butyl ester (1.0 mmol), and 0.14 mL 2-chlorobenzyl chloride (1.1 mmol) were charged. The purification was performed through a column chromatography (ethyl acetate:petroleum ether=1:2) to afford 165 mg titled product with a yield of 35.0%.

(6) (R)-1-(2-chlorobenzyl)-7-(3-aminopiperidin-1-yl)-3-methyl-1H-imidazo[4,5-b]pyridine-2(3H)-one trifluoroacetate The specific operation referred to the step (6) described in Example 1 for details. 161 mg (R)-1-[1-(2-chlorobenzyl)-3-methyl-2-oxo-2,3-dihydro-1H-imidazo[4,5-b]pyridin-7-yl]piperidin-3-yl carbamic acid ter.-butyl ester (0.342 mmol) and 2.4 mL trifluoroacetic acid were charged to afford 100 mg titled product with a yield of 60.2%.

Molecular formula: $C_{19}H_{22}ClN_5O$ Molecular weight: 371.86 Mass spectrum (M+H): m/z: 372.2

$^1$H-NMR ($d_6$-DMSO-$D_2$O, 600 MHz): δ8.03 (d, 1H), 7.52 (d, 1H), 7.32 (t, 1H), 7.24 (t, 1H), 6.95 (d, 1H), 6.73 (d, 1H), 5.31 (d, 1H), 5.17 (d, 1H), 3.41 (s, 3H), 3.11 (d, 1H), 2.82 (s, 1H), 2.74 (d, 1H), 2.65 (t, 1H), 2.51 (s, 1H), 1.91 (d, 1H), 1.55 (d, 1H), 1.30 (d, 1H), 1.13 (d, 1H).

Example 6

The preparation of (R)-2-[[3-methyl-7-[3-(methylamino)piperidin-1-yl]-2-oxo-2,3-dihydro-1H-imidazo[4,5-b]pyridin-1-yl]methyl]benzonitrile (Compound 6) trifluoroacetate The steps (1)-(4) were same as the steps (1)-(4) described in the preparation example of Compound 1.

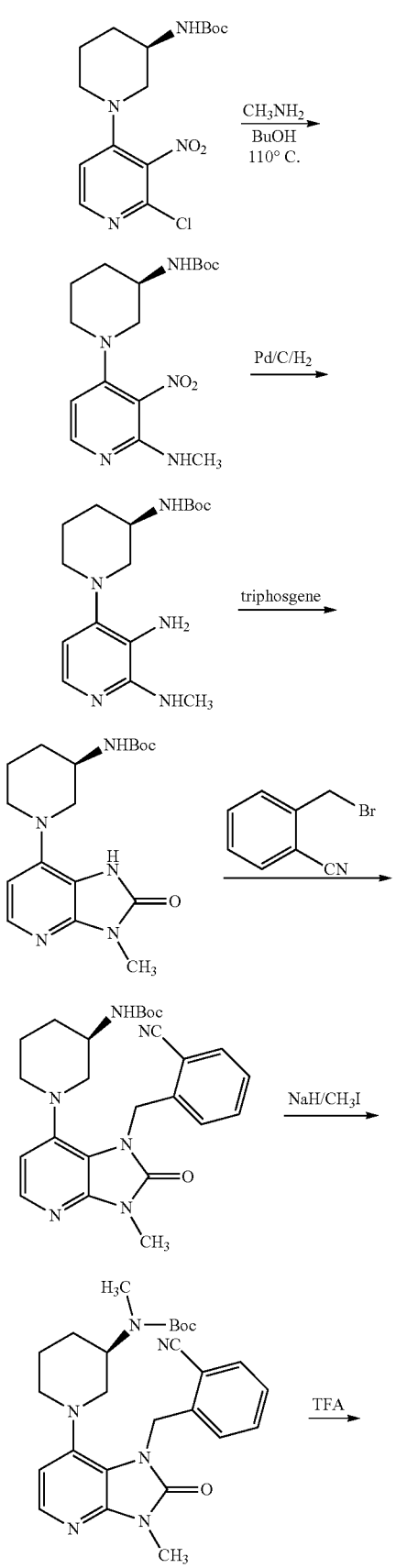

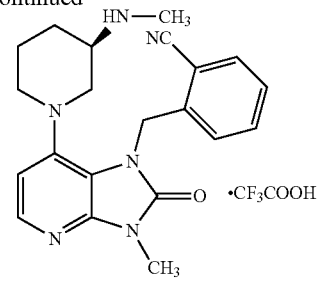

The steps (1)-(4) were same as the steps (1)-(4) described in the preparation example of Compound 1.

(5) (R)-1-[1-(2-cyano-benzyl)-3-methyl-2-oxo-2,3-dihydro-1H-imidazo[4,5-b]pyridin-7-yl]piperidin-3-yl carbamic acid ter.-butyl ester

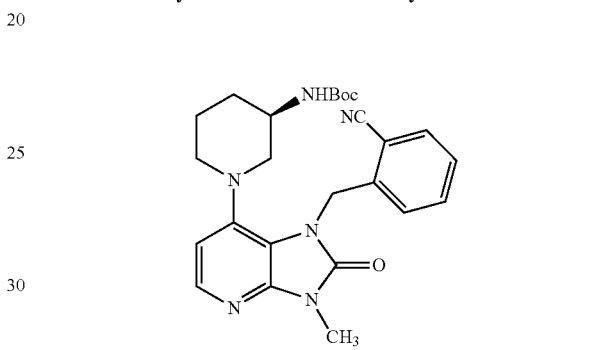

The specific operation referred to the step (5) in Example 1 for details. 694 mg (R)-1-(3-methyl-2-oxo-2,3-dihydro-1H-imidazo[4,5-b]pyridin-7-yl)piperidin-3-yl carbamic acid ter.-butyl ester (2 mmol) and 470 mg 2-(bromomethyl)benzonitrile (2.4 mmol) were charged to afford 830 mg crude product, which was directly used in the subsequent reaction.

(6) (R)-1-[1-(2-cyanobenzyl)-3-methyl-2-oxo-2,3-dihydro-1H-imidazo[4,5-b]pyridin-7-yl]piperidin-3-yl(methyl)carbamic acid ter.-butyl ester

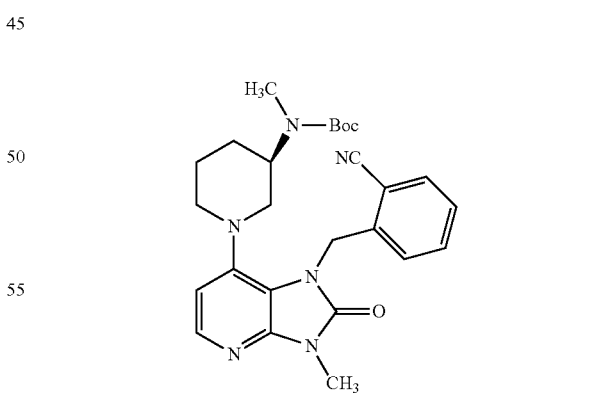

In a dry reaction bottle, 831.6 mg (R)-1-[1-(2-cyano-benzyl)-3-methyl-2-oxo-2,3-dihydro-1H-imidazo[4,5-b]pyridin-7-yl]piperidin-3-yl carbamic acid tert-butyl ester (1.8 mmol) was dissolved in 8 mL DMF. 86 mg 60% sodium hydride (2.16 mmol) was added at 0° C. It was stirred for 30 min at room temperature. 0.12 mL CH$_3$I (1.89 mmol) was added dropwise, and stirred for 4 h at room temperature. The excess NaH was quenched by adding water slowly. The reaction solution was exacted with ethyl acetate. The organic layer was washed with water and brine, respectively, dried with sodium sulfate, and purified through a column chromatography (petroleum ether:ethyl acetate=2:1) to afford 0.25 g titled product with a yield of 29.0%.

(7) (R)-2-[[3-methyl-7-[3-(methylamino)piperidin-1-yl]-2-oxo-2,3-dihydroimidazo[4,5-b]pyridin-1-yl]methyl]benzonitrile trifluoroacetate

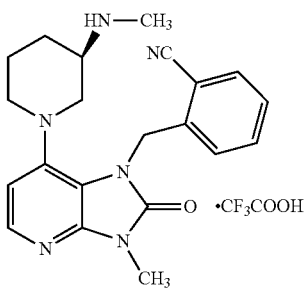 [SMILES: CN[C@@H]1CCCN(c2ccnc3c2n(Cc2ccccc2C#N)c(=O)n3C)C1 ; "·CF3COOH"]

The specific operation referred to the step (6) described in Example 1 for details. 247.5 mg (R)-1-[1-(2-cyano-benzyl)-3-methyl-2-oxo-2,3-dihydro-1H-imidazo[4,5-b]pyridin-7-yl]piperidin-3-yl(methyl)carbamic acid ter.-butyl ester (0.52 mmol) and 2 mL trifluoroacetic acid were charged to afford 80 mg titled product with a yield of 31.3%.

Molecular formula: $C_{21}H_{24}N_6O$ Molecular weight: 376.45
Mass spectrum (M+H): m/z: 377.2

$^1$H-NMR (d$_6$-DMSO-D$_2$O, 600 MHz): δ 8.04 (d, 1H), 7.72 (d, 1H), 7.51 (t, 1H), 7.38 (dd, 1H), 6.94 (d, 1H), 6.81 (d, 1H), 5.52 (q, 2H), 3.56 (s, 3H), 3.16 (d, 1H), 2.82 (s, 1H), 2.81 (d, 1H), 2.60 (m, 1H), 2.50 (s, 3H), 2.16 (m, 1H), 1.72 (m, 1H), 1.49 (m, 2H).

Example 7

The preparation of (R)-2-[[7-(3-aminopiperidin-1-yl)-3,3-dimethyl-2-oxo-2,3-dihydro-1H-pyrrolo[3,2-b]pyridin-1-yl]methyl]benzonitrile (Compound 7) trifluoroacetate

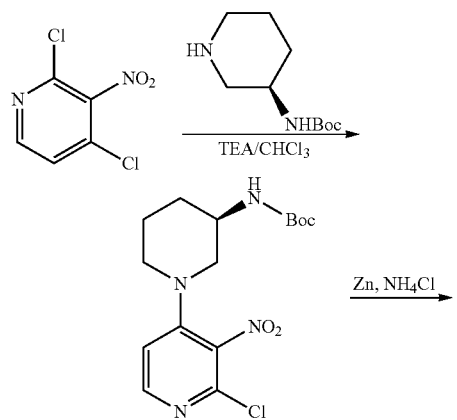

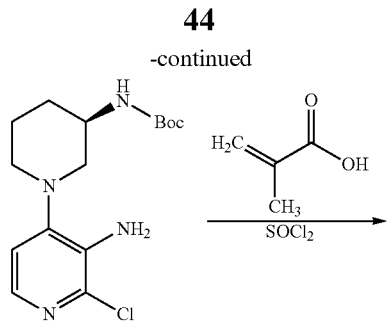

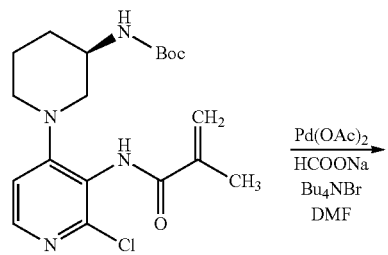

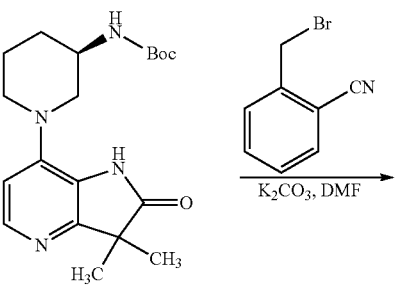

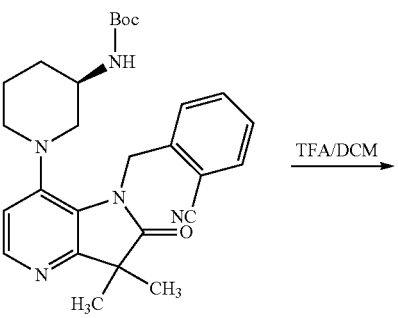

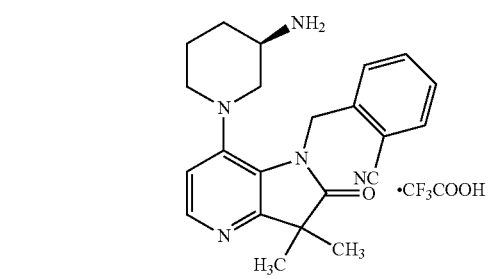

(1) (R)-tert-butyl1-(2-chloro-3-nitropyridin-4-yl)piperidin-3-yl carbamate

The specific operation referred to the step (1) described in Example 1.

(2) (R)-tert-butyl 1-(3-amino-2-chloropyridin-4-yl)piperidin-3-yl carbamate

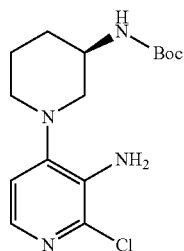 [SMILES: CC(C)(C)OC(=O)N[C@@H]1CCCN(c2ccnc(Cl)c2N)C1]

In a dry reaction bottle, 2.0 g (R)-1-(2-chloro-3-nitropyridin-4-yl)piperidin-3-yl tert-butyl carbamate (5.6 mmol), 3.6 g zinc dust (56 mmol), and 2.97 g ammonium chloride (56 mmol) were added, dissolved in 40 mL solution of methanol and tetrahydrofuran (1:1 ratio by volume), stirred for 5 h at room temperature, filtrated through an air pump, and washed with methanol. The filtrate was concentrated, and purified through a column chromatography (eluted with 10%-25% ethyl acetate/petroleum ether) to afford 1.4 g white solid with a yield of 78.0%.

(3) (R)-1-(2-chloro-3-methylacrylamide pyridin-4-yl)piperidin-3-yl tert-butyl carbamate

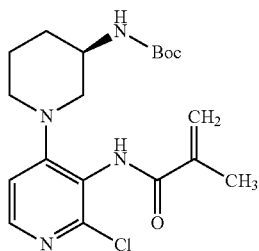 [SMILES: C=C(C)C(=O)Nc1c(N2CCC[C@@H](NC(=O)OC(C)(C)C)C2)ccnc1Cl]

In a dry reaction bottle, 480 mg 2-methacrylic acid (5.6 mmol) was added, and dissolved in 10 mL N,N-dimethylacetamide. 658 mg $SOCl_2$ (5.6 mmol) was added dropwise at 0° C., and stirred for 0.5 h. 1.4 g (R)-1-(3-amino-2-chloropyridin-4-yl)piperidin-3-yl tert-butyl carbamate (4.37 mmol) was added, and stirred overnight. After 30 mL water and 30 mL×3 ethyl acetate were added, it was extracted. The organic layer was washed with brine, dried with anhydrous sodium sulfate, and purified through a column chromatography (petroleum ether/ethyl acetate) to afford 1.3 g solid with a yield of 77.0%.

(4) (R)-1-(3,3-dimethyl-2-oxo-2,3-dihydro-1H-pyrrolo[3,2-b]pyridin-7-yl)piperidin-3-yl tert-butyl carbamate

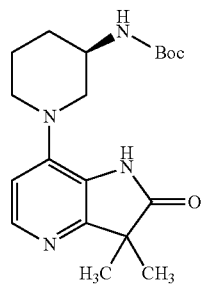 [SMILES: CC(C)(C)OC(=O)N[C@@H]1CCCN(c2ccnc3c2NC(=O)C3(C)C)C1]

In a dry reaction bottle, 1.3 g (R)-1-(2-chloro-3-methylacrylamide pyridin-4-yl)piperidin-3-yl tert-butyl carbamate (3 mmol), 56 mg diacetoxy palladium (0.3 mmol), 8.5 mg tetrabutylammonium bromide (2.5 mmol), and 173 mg sodium formate (3 mmol) were added and dissolved in 20 mL DMF, into which nitrogen gas was introduced, and reacted overnight at 80° C. Extraction was performed by adding water and ethyl acetate. The organic layer was washed with brine, dried with sodium sulfate, concentrated, and purified through a column chromatography (petroleum ether/ethyl acetate) to afford 250 mg solid with a yield of 23.1%.

(5) (R)-1-[1-(2-cyanobenzyl)-3,3-dimethyl-2-oxo-2,3-dihydro-1H-pyrrolo[3,2-b]pyridin-7-yl]piperidin-3-yl tert-butyl carbamate

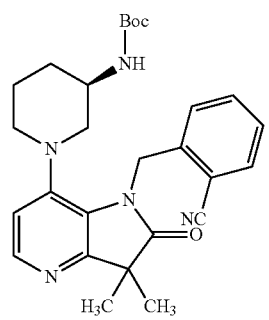 [SMILES: CC(C)(C)OC(=O)N[C@@H]1CCCN(c2ccnc3c2N(Cc2ccccc2C#N)C(=O)C3(C)C)C1]

The specific operation referred to the step (5) described in Example 1. 250 mg (R)-1-(3,3-dimethyl-2-oxo-2,3-dihydro-1H-pyrrolo[3,2-b]pyridin-7-yl)piperidin-3-yl tert-butyl carbamate (0.69 mmol), 161 mg 2-(bromomethyl)benzonitrile (0.83 mmol), and 191 mg potassium carbonate (1.4 mmol) were charged to afford 140 mg titled product with a yield of 42%.

(6) (R)-2-[[7-(3-aminopiperidin-1-yl)-3,3-dimethyl-2-oxo-2,3-dihydro-1H-pyrrolo[3,2-b]pyridin-1-yl]methyl]benzonitrile trifluoroacetate

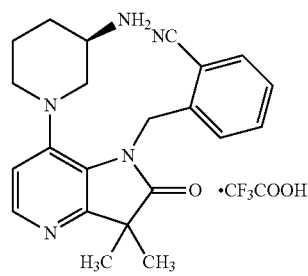 [SMILES: CC1(C)C(=O)N(Cc2ccccc2C#N)c2c(N3CCC[C@@H](N)C3)ccnc21 ; "·CF3COOH"]

The specific operation referred to the step (6) described in Example 1. 140 mg (R)-1-[1-(2-cyano-benzyl)-3,3-dimethyl-2-oxo-2,3-dihydro-1H-pyrrolo[3,2-b]pyridin-7-yl]piperidin-3-yl tert-butyl carbamate (0.29 mmol) and 2.4 mL trifluoroacetic acid were charged to afford 95 mg titled product with a yield of 66.9%.

Molecular formula: $C_{22}H_{25}N_5O$ Molecular weight: 375.47
Mass spectrum (M+H): m/z: 376.3
$^1$H-NMR ($d_6$-DMSO-$D_2O$, 600 MHz): δ 8.20 (d, 1H), 7.90 (d, 1H), 7.62 (t, 1H), 7.47 (t, 1H), 7.16 (d, 1H), 6.98 (d, 1H), 5.37 (d, 1H), 5.27 (d, 1H), 3.06 (s, 1H), 2.76 (d, 2H), 2.52 (s, 2H), 1.93 (d, 1H), 1.63 (d, 1H), 1.37 (s, 6H), 1.24 (t, 2H).

Example 8

The preparation of (R)-4-[[7-(3-aminopiperidin-1-yl)-3-methyl-2-oxo-2,3-dihydro-1H-pyrrolo[4,5-b]pyridin-1-yl]methyl]benzonitrile (Compound 8) trifluoroacetate

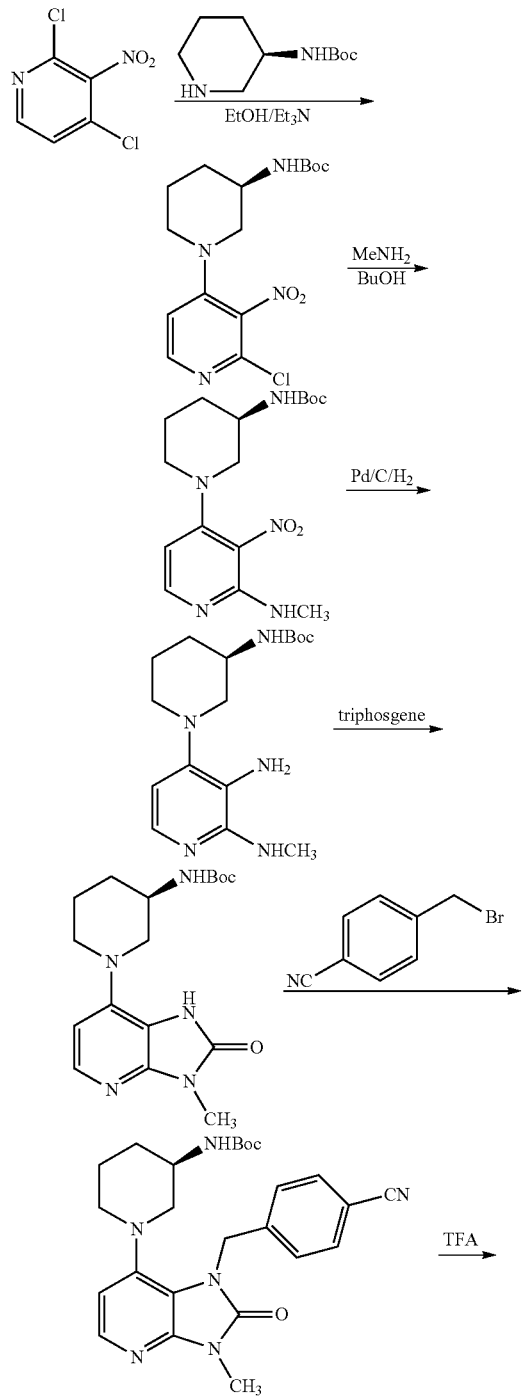

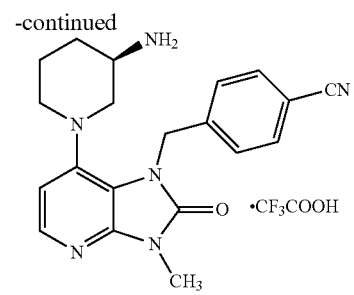

The steps (1)-(4) were same as the steps (1)-(4) described in the preparation example of Compound 1.

(5) (R)-1-[1-(4-cyanobenzyl)-3-methyl-2-oxo-2,3-dihydro-1H-imidazo[4,5-b]pyridin-7-yl]piperidin-3-yl carbamic acid tert-butyl ester

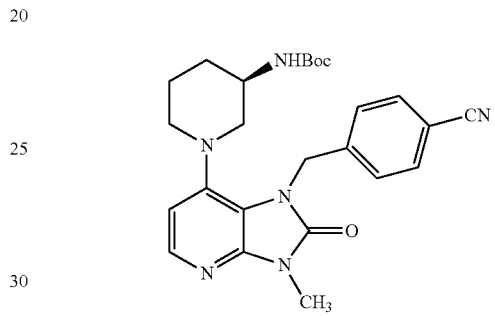

The specific operation referred to the step (5) described in Example 1 for details. 347 mg (R)-1-(3-methyl-2-oxo-2,3-dihydro-1H-imidazo[4,5-b]pyridin-7-yl)piperidin-3-yl carbamic acid ter.-butyl ester (1 mmol) and 235 mg 4-(bromomethyl)benzonitrile (1.2 mmol) were charged. A column chromatography was performed to afford 350 mg titled product with a yield of 75.6%.

(6) (R)-4-[[7-(3-aminopiperidin-1-yl)-3-methyl-2-oxo-2,3-dihydro-1H-pyrrolo[4,5-b]pyridin-1-yl]methyl]benzonitrile trifluoroacetate

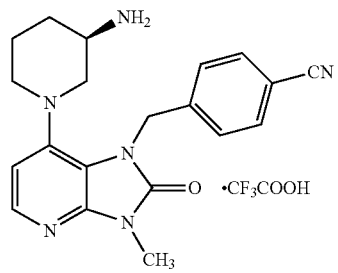 [SMILES: Cn1c(=O)n(Cc2ccc(C#N)cc2)c2c(N3CCC[C@@H](N)C3)ccnc21 ; "·CF3COOH"]

The operation referred to the step (6) described in Example 1. 348 mg (R)-1-[1-(4-cyanobenzyl)-3-methyl-2-oxo-2,3-dihydro-1H-imidazo[4,5-b]pyridin-7-yl]piperidin-3-yl carbamic acid ter.-butyl ester (0.75 mmol) and 2.0 mL trifluoroacetic acid were charged to afford 270 mg titled product with a yield of 99%.

Molecular formula: $C_{20}H_{22}N_6O$ Molecular weight: 362.43
Mass spectrum (M+H): m/z: 363.2
$^1$H-NMR ($d_6$-DMSO-$D_2O$, 600 MHz): δ 8.00 (d, 1H), 7.77 (d, 2H), 7.35 (d, 2H), 6.91 (d, 1H), 5.30 (d, 1H), 5.22 (d, 1H), 3.38 (s, 3H), 3.16 (d, 1H), 3.04 (m, 1H), 2.87 (d, 1H), 2.69 (m, 1H), 2.56 (m, 1H), 1.97 (m, 1H), 1.65 (m, 1H), 1.35 (m, 2H).

Example 9

The preparation of (R)-3-[[7-(3-aminopiperidin-1-yl)-3-methyl-2-oxo-2,3-dihydro-1H-pyrrolo[4,5-b]pyridin-1-yl]methyl]benzonitrile (Compound 9) trifluoroacetate

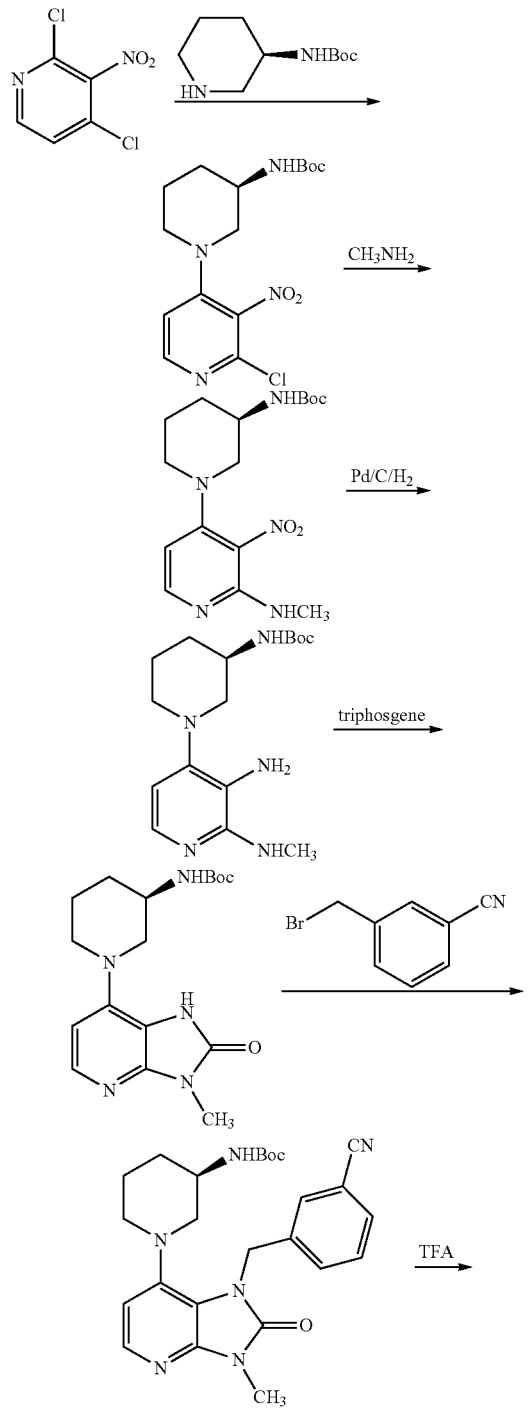

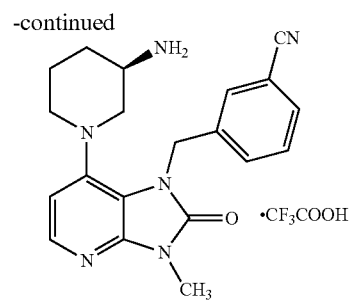

The steps (1)-(4) were same as the steps (1)-(4) described in the preparation example of Compound 1.

(5) (R)-1-[1-(3-cyano-benzyl)-3-methyl-2-oxo-2,3-dihydro-1H-imidazo[4,5-b]pyridin-7-yl]piperidin-3-yl carbamic acid tert-butyl ester

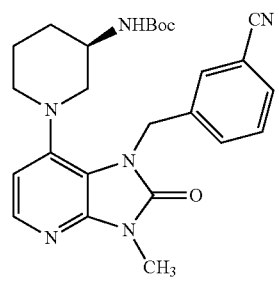 [SMILES: Cn1c(=O)n(Cc2cccc(C#N)c2)c2c(N3CCC[C@@H](NC(=O)OC(C)(C)C)C3)ccnc21]

The specific operation referred to the step (5) described in Example 1 for details. 347 mg (R)-1-(3-methyl-2-oxo-2,3-dihydro-1H-imidazo[4,5-b]pyridin-7-yl)piperidin-3-yl carbamic acid ter.-butyl ester (1 mmol) and 235 mg 3-(bromomethyl)benzonitrile (1.2 mmol) were charged. A column chromatography was performed to afford 292 mg titled product with a yield of 63.2%.

(6) (R)-3-[[7-(3-aminopiperidin-1-yl)-3-methyl-2-oxo-2,3-dihydro-1H-pyrrolo[4,5-b]pyridin-1-yl]methyl]benzonitrile trifluoroacetate

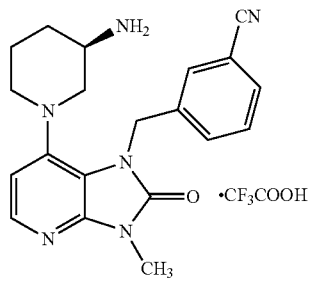 [SMILES: Cn1c(=O)n(Cc2cccc(C#N)c2)c2c(N3CCC[C@@H](N)C3)ccnc21 ; "·CF3COOH"]

The operation referred to the step (6) described in Example 1. 290 mg (R)-1-[1-(3-cyanobenzyl)-3-methyl-2-oxo-2,3-dihydro-1H-imidazo[4,5-b]pyridin-7-yl]piperidin-3-yl carbamic acid ter.-butyl ester (0.63 mmol) and 1.0 mL trifluoroacetic acid were charged to afford 150 mg titled product with a yield of 50%.

Molecular formula: $C_{20}H_{22}N_6O$ Molecular weight: 362.43
Mass spectrum (M+H): m/z: 363.2
$^1$H-NMR (d$_6$-DMSO-D$_2$O, 600 MHz): δ 8.01 (d, 1H), 7.72 (d, 1H), 7.68 (s, 1H), 7.53 (t, 1H), 7.48 (d, 1H), 6.92 (d, 1H), 5.25 (s, 2H), 3.38 (s, 3H), 3.22 (d, 1H), 3.15 (m, 1H), 2.85 (d, 1H), 2.70 (m, 1H), 2.60 (m, 1H), 1.99 (m, 1H), 1.66 (m, 1H), 1.36 (m, 2H).

Example 10

The preparation of (R)-2-[[7-(3-aminopiperidin-1-yl)-3-methyl-2-oxo-2,3-dihydro-1H-imidazo[4,5-b]pyridin-1-yl]methyl]-5-chlorobenzonitrile (Compound 10) trifluoroacetate

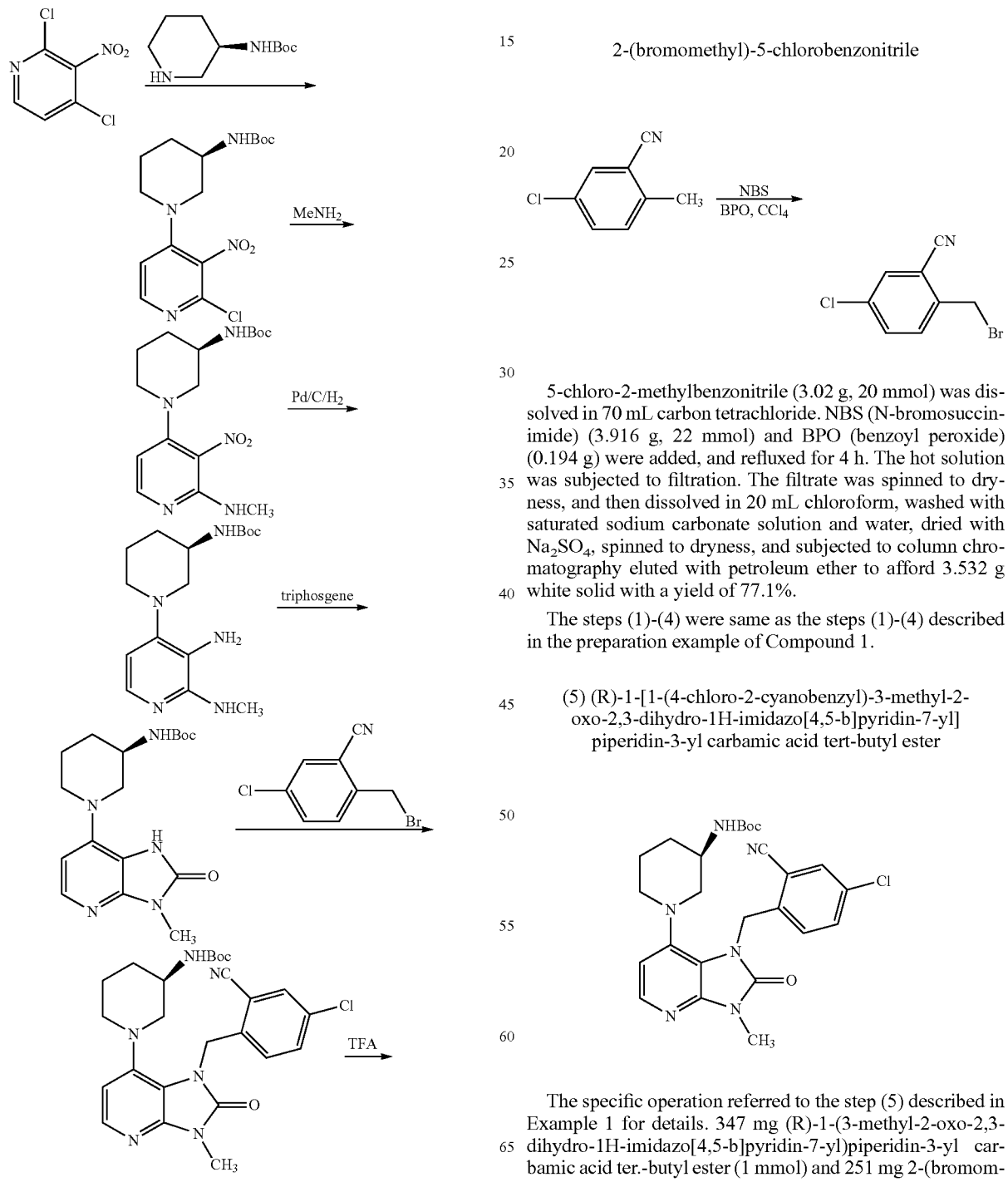

2-(bromomethyl)-5-chlorobenzonitrile 5-chloro-2-methylbenzonitrile (3.02 g, 20 mmol) was dissolved in 70 mL carbon tetrachloride. NBS (N-bromosuccinimide) (3.916 g, 22 mmol) and BPO (benzoyl peroxide) (0.194 g) were added, and refluxed for 4 h. The hot solution was subjected to filtration. The filtrate was spinned to dryness, and then dissolved in 20 mL chloroform, washed with saturated sodium carbonate solution and water, dried with Na$_2$SO$_4$, spinned to dryness, and subjected to column chromatography eluted with petroleum ether to afford 3.532 g white solid with a yield of 77.1%.

The steps (1)-(4) were same as the steps (1)-(4) described in the preparation example of Compound 1.

(5) (R)-1-[1-(4-chloro-2-cyanobenzyl)-3-methyl-2-oxo-2,3-dihydro-1H-imidazo[4,5-b]pyridin-7-yl]piperidin-3-yl carbamic acid tert-butyl ester The specific operation referred to the step (5) described in Example 1 for details. 347 mg (R)-1-(3-methyl-2-oxo-2,3-dihydro-1H-imidazo[4,5-b]pyridin-7-yl)piperidin-3-yl carbamic acid ter.-butyl ester (1 mmol) and 251 mg 2-(bromomethyl)-5-chlorobenzonitrile (1.1 mmol) were charged. A column chromatography was performed to afford 300 mg titled product with a yield of 60.5%.

(6) (R)-2-[[7-(3-aminopiperidin-1-yl)-3-methyl-2-oxo-2,3-dihydro-1H-imidazo[4,5-b]pyridin-1-yl]methyl]-5-chlorobenzonitrile trifluoroacetate

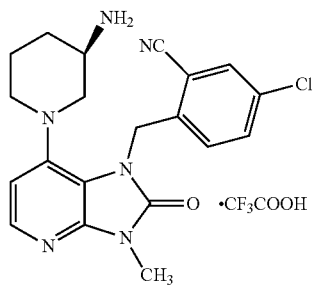 [SMILES: Cn1c(=O)n(Cc2ccc(Cl)cc2C#N)c2c(N3CCC[C@@H](N)C3)ccnc21 ; "·CF3COOH"]

The operation referred to the step (6) described in Example 1. 300 mg (R)-1-[1-(4-chloro-2-cyano-benzyl)-3-methyl-2-oxo-2,3-dihydro-1H-imidazo[4,5-b]pyridin-7-yl]piperidin-3-yl carbamic acid tert-butyl ester (0.605 mmol) and 4.15 mL trifluoroacetic acid were charged to afford 112 mg titled product with a yield of 36.2%.

Molecular formula: $C_{20}H_{21}ClN_6O$ Molecular weight: 396.87 Mass spectrum (M+H): m/z: 397.2

$^1$H-NMR ($d_6$-DMSO-$D_2$O, 600 MHz): δ 8.05 (d, 1H), 8.04 (d, 1H), 7.67 (dd, 1H), 7.07 (d, 1H), 6.98 (d, 1H), 5.43 (d, 1H), 5.34 (d, 1H), 3.38 (s, 3H), 3.18 (d, 1H), 3.01 (m, 1H), 2.86 (d, 1H), 2.70 (m, 1H), 2.60 (m, 1H), 1.97 (m, 1H), 1.70 (m, 1H), 1.35 (m, 2H).

Example 11

The preparation of (R)-2-[[7-(3-aminopiperidin-1-yl)-2-oxo-oxazolo[5,4-b]pyridin-1(2H)-yl]methyl]benzonitrile (Compound 11) trifluoroacetate

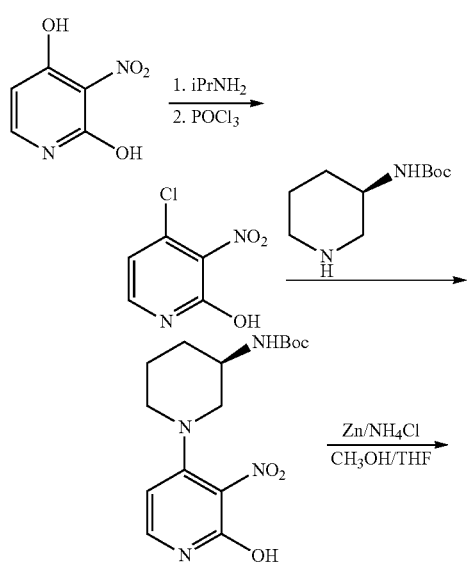

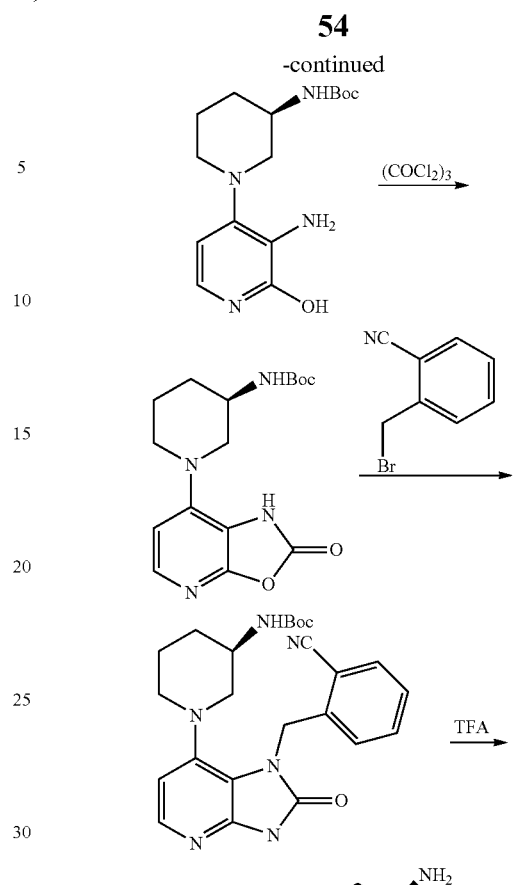

(1) 4-chloro-3-nitropyridin-2-ol

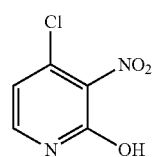

3-nitropyridin-2,4-diol (1.56 g, 10 mmol) was dissolved in 10 mL MeOH, to which isopropylamine (2.14 mL, 25 mmol) was added, heated to 50° C. and reacted for 2 h. The solvent was concentrated. The residue was dissolved in POCl$_3$ (6 mL), and the stirring was continued for 36 h at room temperature. It was poured into cold water, and the solid obtained through filtration was dried under vacuum to afford 1.2 g light yellow solid with a yield of 69%.

(2) (R)-1-(2-hydroxy-3-nitropyridin-4-yl)piperidin-3-yl tert-butyl carbamate

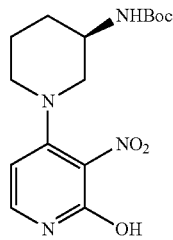 [SMILES: CC(C)(C)OC(=O)N[C@@H]1CCCN(c2ccnc(O)c2[N+](=O)[O-])C1]

The operation referred to the step (1) described in Example 1. 1.2 g 4-chloro-3-nitropyridin-2-ol (6.89 mmol), and 1.6 g (R)-tert-butylpiperidin-3-yl-carbamate (8.0 mmol) were charged to afford 1.7 g titled product with a yield of 72.9%.

(3) (R)-1-(2-hydroxy-3-aminopyridin-4-yl)piperidin-3-yl tert-butyl carbamate

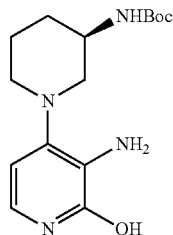 [SMILES: CC(C)(C)OC(=O)N[C@@H]1CCCN(c2ccnc(O)c2N)C1]

(R)-1-(2-hydroxy-3-nitropyridin-4-yl)piperidin-3-yl tert-butyl carbamate (0.676 g, 2 mmol), zinc dust (1.3 g, 20 mmol) and $NH_4Cl$ (1.06 g, 20 mmol) were mixed in MeOH and THF (20 mL, V:V=1:1), stirred overnight at room temperature, and filtrated. The filter cake was washed with MeOH. The filtrate was spinned to dryness and subjected to column chromatography ($CH_2Cl_2$:MeOH=20:1) to afford 320 mg solid with a yield of 52%.

(4) (R)-1-(2-oxo-1,2-dihydrooxazole) [5,4-b]pyridin-7-yl piperidin-3 tert-butyl carbamate

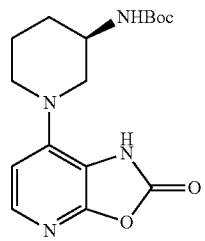 [SMILES: CC(C)(C)OC(=O)N[C@@H]1CCCN(c2ccnc3oc(=O)[nH]c23)C1]

The operation referred to the step (4) described in Example 1. 320 mg (R)-1-(2-hydroxy-3-aminopyridin-4-yl)piperidin-3-yl tert-butyl carbamate (1.04 mmol) and 0.339 g triphosgene (1.14 mmol) were charged to afford 300 mg titled product with a yield of 86.4%.

(5) (R)-1-[1-(2-cyano-benzyl)-2-oxo-1,2-dihydrooxazole][5,4-b]pyridin-7-yl piperidin-3 tert-butyl carbamate

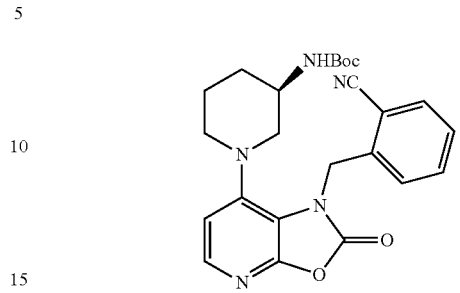

The operation referred to the step (5) described in Example 1. 300 mg (R)-1-(2-oxo-1,2-dihydrooxazole)[5,4-b]pyridin-7-ylpiperidin-3 tert-butyl carbamate (0.89 mmol) and 192 mg o-cyanobenzyl bromide (0.98 mmol) were charged to afford 220 mg titled product with a yield of 54.9%.

(6) (R)-2-[[7-(3-aminopiperidin-1-yl)-2-oxo-oxazolo[5,4-b]pyridin-1(2H)-yl]methyl]benzonitrile trifluoroacetate

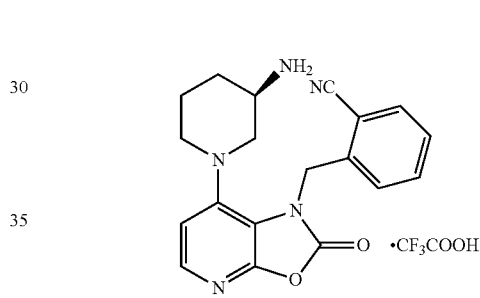

The operation referred to the step (6) described in Example 1. 220 mg (R)-1-[1-(2 cyanobenzyl)-2-oxo-1,2-dihydrooxazole][5,4-b]pyridin-7-ylpiperidin-3 tert-butyl carbamate (0.489 mmol) and 4 mL trifluoroacetic acid were charged to afford 160 mg titled product with a yield of 70.6%.

Molecular formula: $C_{19}H_{19}N_5O_2$ Molecular weight: 349.39 Mass spectrum (M+H): m/z: 350.2

$^1$H-NMR ($d_6$-DMSO-$D_2O$, 600 MHz): δ 8.01 (d, 1H), 7.89 (d, 1H), 7.69 (t, 1H), 7.53 (t, 1H), 7.40 (d, 1H), 7.13 (d, 1H), 5.41 (d, 1H), 5.30 (d, 1H), 3.25 (d, 1H), 3.05 (m, 1H), 2.93 (d, 1H), 2.77 (m, 1H), 2.65 (m, 1H), 1.95 (m, 1H), 1.66 (m, 1H), 1.46-1.26 (m, 2H).

Example 12

The preparation of (R)-2-[[7-(3-aminopyrrolidin-1-yl)-3-methyl-2-oxo-2,3-dihydro-1H-imidazo[4,5-b]pyridin-1-yl]methyl]benzonitrile (Compound 12) trifluoroacetate

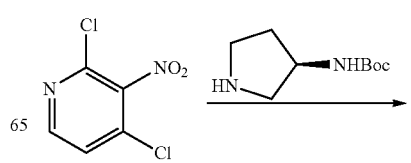

57
-continued

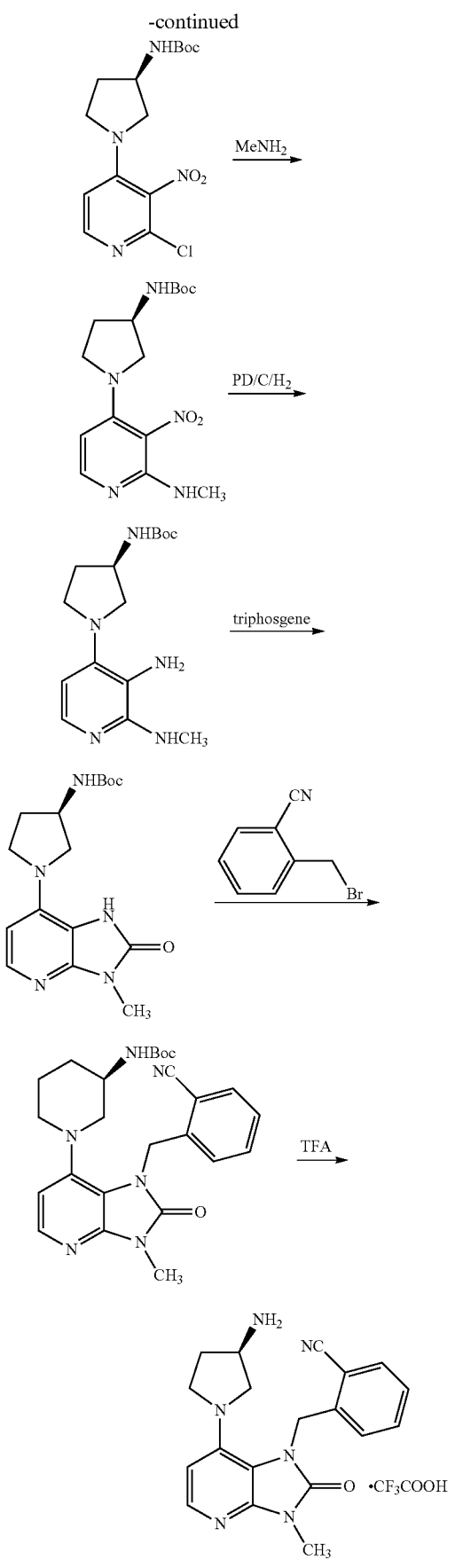

58

(1) (R)-1-(2-chloro-3-nitropyridin-4-yl)pyrrolidin-3-yl tert-butyl carbamate

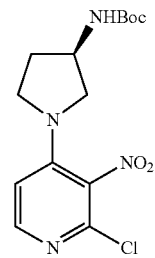

The operation referred to the step (1) described in Example 1. 960 mg 2,4-dichloro-3-nitropyridine (5 mmol) and 931 mg (R)-tert-butylpyrrolidin-3-yl-carbamate (5 mmol) were charged to afford 1.55 g titled product with a yield of 91.2%.

(2) (R)-1-(2-methylamino-3-nitropyridin-4-yl)pyrrolidin-3-yl tert-butyl carbamate

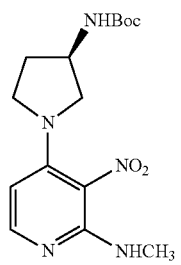

The operation referred to the step (2) described in Example 1. 1550 mg (R)-1-(2-chloro-3-nitropyridin-4-yl)pyrrolidin-3-yl tert-butyl carbamate (4.52 mmol), and 15 mL solution of methylamine in alcohol were charged to afford 1.30 g titled product with a yield of 85.0%.

(3) (R)-1-(2-methylamino-3-aminopyridin-4-yl)pyrrolidin-3-yl tert-butyl carbamate

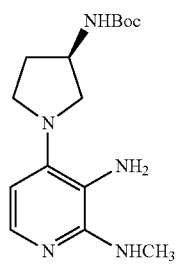

The operation referred to the step (3) described in Example 1. 1.30 g (R)-1-(2-methylamino-3-nitropyridin-4-yl)pyrrolidin-3-yl tert-butyl carbamate (3.86 mmol), and 130 mg 10% Pd—C were charged to afford 0.91 g titled product with a yield of 76.8%.

(4) (R)-1-(3-methyl-2-oxo-2,3-dihydro-1H-imidazo[4,5-b]pyridin-7-yl)pyrrolidin-3-yl tert-butyl carbamate

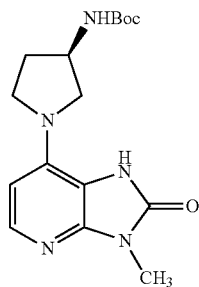 [SMILES: Cn1c(=O)[nH]c2c(N3CC[C@@H](NC(=O)OC(C)(C)C)C3)ccnc21]

The operation referred to the step (4) described in Example 1, 0.91 g (R)-1-(2-methylamino-3-aminopyridin-4-yl)pyrrolidin-3-yl tert-butyl carbamate (2.96 mmol), and 879 mg triphosgene (2.96 mmol) were charged to afford 0.89 g titled product with a yield of 90.3%.

(5) (R)-1-[1-(2-cyano-benzyl)-3-methyl-2-oxo-2,3-dihydro-1H-imidazo[4,5-b]pyridin-7-yl]pyrrolidin-3-yl tert-butyl carbamate

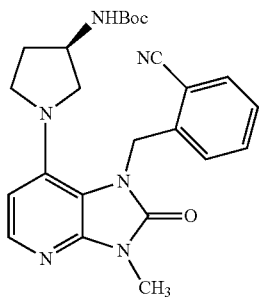 [SMILES: Cn1c(=O)n(Cc2ccccc2C#N)c2c(N3CC[C@@H](NC(=O)OC(C)(C)C)C3)ccnc21]

The operation referred to the step (5) described in Example 1. 0.89 g (R)-1-(3-methyl-2-oxo-2,3-dihydro-1H-imidazo[4,5-b]pyridin-7-yl)pyrrolidin-3-yl tert-butyl carbamate (2.67 mmol) and 523 mg o-cyanobenzyl bromide (2.67 mmol) were charged to afford 600 mg titled product with a yield of 50.2%.

(6) (R)-2-[[7-(3-aminopyrrolidin-1-yl)-3-methyl-2-oxo-2,3-dihydroimidazo[4,5-b]pyridin-1-yl]methyl]benzonitrile trifluoroacetate

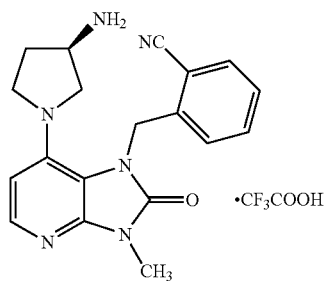 [SMILES: Cn1c(=O)n(Cc2ccccc2C#N)c2c(N3CC[C@@H](N)C3)ccnc21 ; "·CF3COOH"]

The operation referred to the step (6) described in Example 1. 600 mg (R)-1-[1-(2-cyanobenzyl)-3-methyl-2-oxo-2,3-dihydro-1H-imidazo[4,5-b]pyridin-7-yl]pyrrolidin-3-yl tert-butyl carbamate (1.34 mmol) and 5 mL trifluoroacetic acid were charged to afford 360 mg titled product with a yield of 77.2%.

Molecular formula: $C_{19}H_{20}N_6O$ Molecular weight: 348.40
Mass spectrum (M+H): m/z: 349.2
$^1$H-NMR (D$_2$O, 400 MHz): δ 7.86 (d, 1H), 7.66 (d, 1H), 7.46 (t, 1H), 7.33 (t, 1H), 7.09 (d, 1H), 6.86 (d, 1H), 5.42 (d, 1H), 5.38 (d, 1H), 3.84 (d, 1H), 3.37 (m, 1H), 3.32 (s, 3H), 3.12 (m, 1H), 3.03 (m, 1H), 2.94 (m, 1H), 2.26 (m, 1H), 1.82 (m, 1H).

Example 13

The preparation of (R)-2-[[7-(3-aminopiperidin-1-yl)-3-methyl-2-thio-2,3-dihydro-1H-imidazo[4,5-b]pyridin-1-yl]methyl]benzonitrile (Compound 13) trifluoroacetate

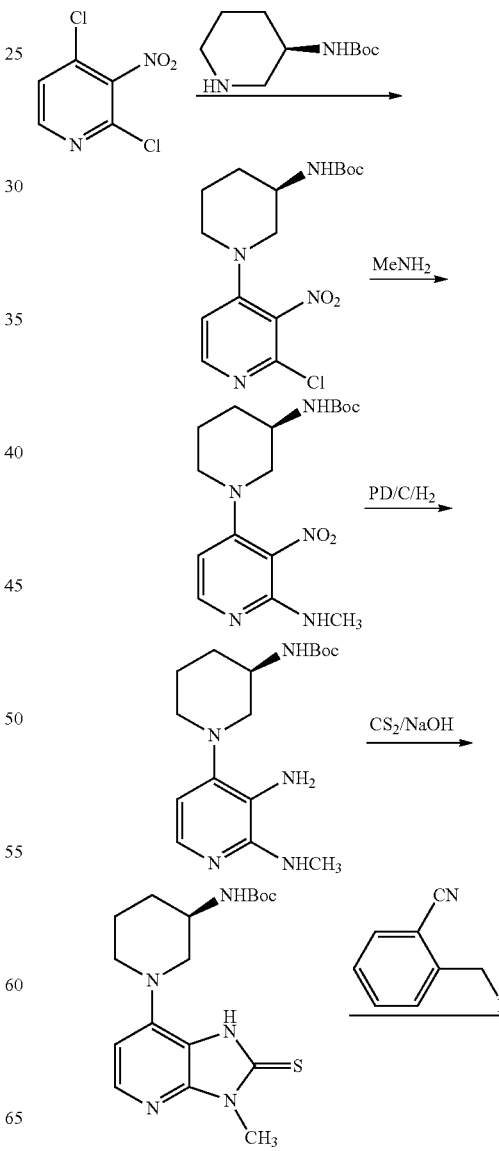

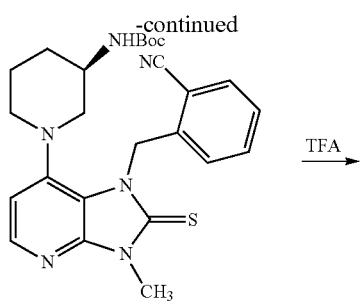

The steps (1)-(3) were same as the steps (1)-(3) described in the preparation example of Compound 1.

(4) (R)-1-(3-methyl-2-thio-2,3-dihydro-1H-imidazo[4,5-b]pyridin-7-yl)piperidin-3-yl carbamic acid tert-butyl ester

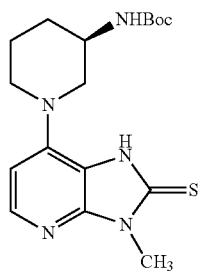 [SMILES: Cn1c(=S)[nH]c2c(N3CCC[C@@H](NC(=O)OC(C)(C)C)C3)ccnc21]

CS$_2$ (167 mg, 2.2 mmol) and 1 N NaOH (0.22 mL, 2.2 mmol) were dissolved in EtOH (3 mL). (R)-1-[3-amino-2-(methylamino)pyridin-4-yl]piperidin-3-yl tert-butyl carbamate (321 mg, 1.0 mmol) was added, stirred for 2 days at 50° C., diluted by adding EA, and washed sequentially with NH$_4$Cl, H$_2$O, and brine. The organic layer was dried with Na$_2$SO$_4$, and spinned to dryness to afford 320 mg titled product as white solid with a yield of 88%.

(5) (R)-1-[1-(2-cyanobenzyl)-3-methyl-2-thio-2,3-dihydro-1H-imidazo[4,5-b]pyridin-7-yl]piperidin-3-yl tert-butyl carbamate

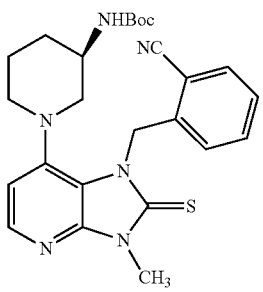 [SMILES: Cn1c(=S)n(Cc2ccccc2C#N)c2c(N3CCC[C@@H](NC(=O)OC(C)(C)C)C3)ccnc21]

The operation referred to the step (5) described in Example 1 for details. 160 mg (R)-1-(3-methyl-2-thio-2,3-dihydro-1H-imidazo[4,5-b]pyridin-7-yl)piperidin-3-ylcarbamic acid tert-butyl ester (0.44 mmol) and 95 mg o-cyanobenzyl bromide (0.48 mmol) were charged. A column chromatography was performed to afford 150 mg titled product as white solid with a yield of 71.0%.

(6) (R)-2-[[7-(3-aminopiperidin-1-yl)-3-methyl-2-thio-2,3-dihydro-1H-imidazo[4,5-b]pyridin-1-yl]methyl]benzonitrile trifluoroacetate

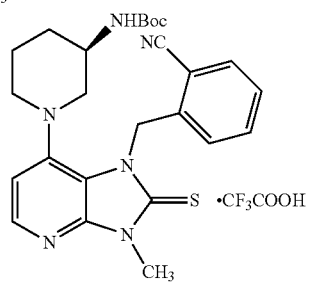

The operation referred to the step (6) described in Example 1. 150 mg (R)-1-[1-(2-cyanobenzyl)-3-methyl-2-thio-2,3-dihydro-1H-imidazo[4,5-b]pyridin-7-yl]piperidin-3-yl tert-butyl carbamate (0.31 mmol) and 1.8 mL trifluoroacetic acid were charged to afford 102 mg titled product with a yield of 86.0%.

Molecular formula: C$_{20}$H$_{22}$N$_6$S Molecular weight: 378.49
Mass spectrum (M+H): m/z: 379.2

1H-NMR (D2O, 400 MHz): δ 7.79 (d, 1H), 7.50 (m, 2H), 7.43 (d, 1H), 7.30 (t, 1H), 6.71 (d, 1H), 4.65 (m, 1H), 4.38 (s, 2H), 4.23 (m, 1H), 3.73 (m, 1H), 3.60 (s, 3H), 3.50 (m, 1H), 3.39 (m, 1H), 2.09 (m, 1H), 1.83 (m, 1H), 1.66 (m, 2H).

Example 14

The preparation of 2-[[7-(1,4-homopiperazin-1-yl)-3-methyl-2-oxo-2,3-dihydro-1H-imidazo[4,5-b]pyridin-1-yl]methyl]benzonitrile (Compound 14) trifluoroacetate

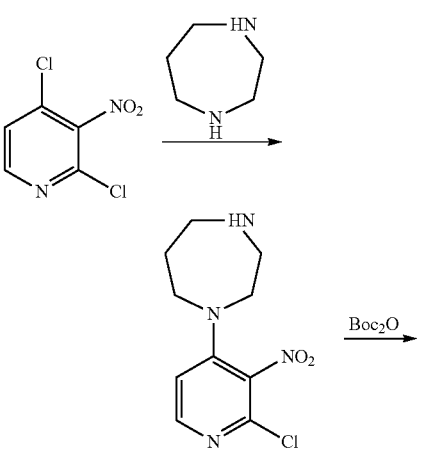

-continued

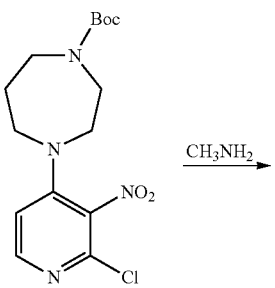

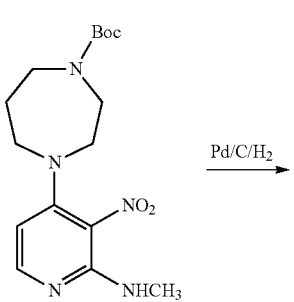

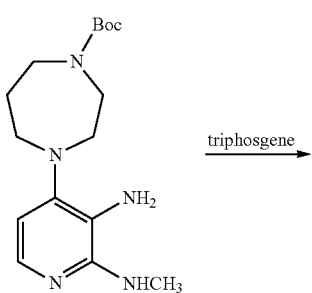

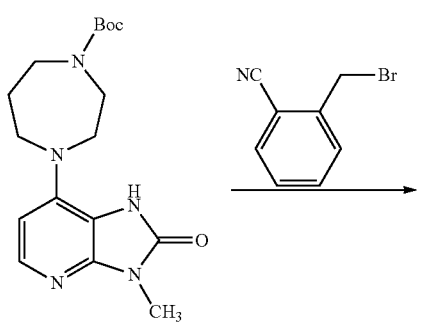

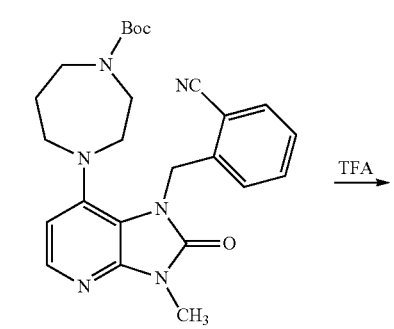

-continued

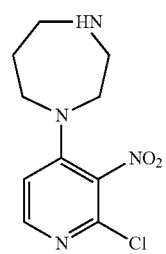 [SMILES: O=[N+]([O-])c1c(N2CCCNCC2)ccnc1Cl]

(1) 1-(2-chloro-3-nitropyridin-4-yl)-1,4-homopiperazine

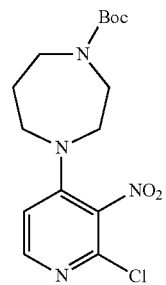 [SMILES: CC(C)(C)OC(=O)N1CCCN(c2ccnc(Cl)c2[N+](=O)[O-])CC1]

The operation referred to the step (1) described in Example 1 for details. 3.072 g 2,4-dichloro-3-nitropyridine (16.0 mmol) and 1.75 g homopiperazine (17.5 mmol) were charged to afford 2.873 g titled product with a yield of 70.1%.

(2) 4-(2-chloro-3-nitropyridin-4-yl)-1,4-homopiperazin-1-yl tert-butyl formate 1-(2-chloro-3-nitropyridin-4-yl)-1,4-homopiperazine (2.873 g, 11.223 mmol), Di-tert-butyl dicarbonate (2.93 mL, 13.441 mmol) and triethylamine (3.13 mL, 22.483 mmol) were dissolved in 110 mL acetonitrile/water (1:1), and the stirring was continued for 3 h at room temperature. CH₂Cl₂ and water were added. The organic phase was separated and the aqueous phase was extracted with CH₂Cl₂. The organic phase was combined, washed with saturated brine, died with anhydrous Na₂SO₄, and concentrated to afford a crude product as 4.484 g yellow solid.

(3) 4-(2-methylamino-3-nitropyridin-4-yl)-1,4-homopiperazin-1-yl tert-butyl formate

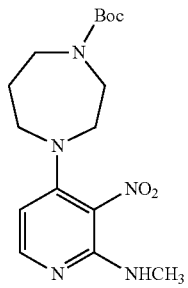 [SMILES: CNc1nccc(N2CCCN(C(=O)OC(C)(C)C)CC2)c1[N+](=O)[O-]]

The specific operation referred to the step (2) described in Example 1 for details. 3.965 g 4-(2-chloro-3-nitropyridin-4-yl)-1,4-homopiperazin-1-yl tert-butyl formate (11.138 mmol), and 6.279 g 27% solution of methylamine in alcohol were charged to afford 4.07 g crude product.

(4) 4-(2-methylamino-3-aminopyridin-4-yl)-1,4-homopiperazin-1-yl tert-butyl formate

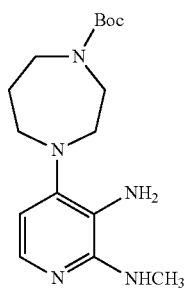 [SMILES: CNc1nccc(N2CCCN(C(=O)OC(C)(C)C)CC2)c1N]

The specific operation referred to the step (3) described in Example 1 for details. 4-(2-methylamino-3-nitropyridin-4-yl)-1,4-homopiperazin-1-yl tert-butyl formate (3.558 g, 10.138 mmol) and 0.356 g 10% Pd—C were charged to afford 3.614 g crude product.

(5) 4-(3-methyl-2-oxo-2,3-dihydro-1H-imidazo[4,5-b]pyridin-7-yl)-1,4-homopiperazin-1-yl tert-butyl formate

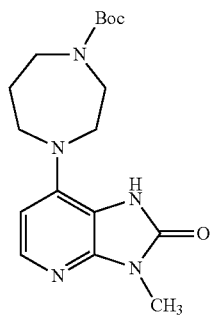 [SMILES: Cn1c(=O)[nH]c2c(N3CCCN(C(=O)OC(C)(C)C)CC3)ccnc21]

The specific operation referred to the step (4) described in Example 1 for details. 4-(2-methylamino-3-aminopyridin-4-yl)-1,4-homopiperazin-1-yl tert-butyl formate (3.185 g, 9.922 mmol), triphosgene (3.238 g, 10.913 mmol), and triethylamine (5.52 mL, 39.651 mmol) were charged. A column chromatography (CH$_2$Cl$_2$: MeOH=30:1) was performed to afford 0.505 g titled product with a yield of 14.7%.

(6) 4-[1-(2-cyanobenzyl)-3-methyl-2-oxo-2,3-dihydro-1H-imidazo[4,5-b]pyridin-7-yl]-1,4-homopiperazin-1-yl tert-butyl formate

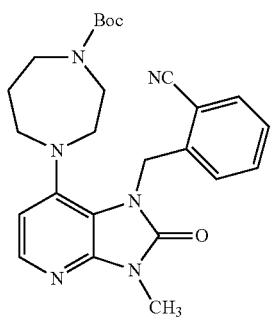 [SMILES: Cn1c(=O)n(Cc2ccccc2C#N)c2c(N3CCCN(C(=O)OC(C)(C)C)CC3)ccnc21]

The specific operation referred to the step (5) described in Example 1 for details. 4-(3-methyl-2-oxo-2,3-dihydro-1H-imidazo[4,5-b]pyridin-7-yl)-1,4-homopiperazin-1-yl tert-butyl formate (0.505 g, 1.455 mmol), 2-(bromomethyl)benzonitrile (0.284 g, 1.456 mmol), and potassium carbonate (0.402 g, 2.913 mmol) were charged. A column chromatography (Ethyl acetate: CH$_2$Cl$_2$=1:1) was performed to afford 0.287 g titled product with a yield of 42.7%.

(7) 2-[[7-(1,4-homopiperazin-1-yl)-3-methyl-2-oxo-2,3-dihydro-1H-imidazo[4,5-b]pyridin-1-yl]methyl]benzonitrile trifluoroacetate

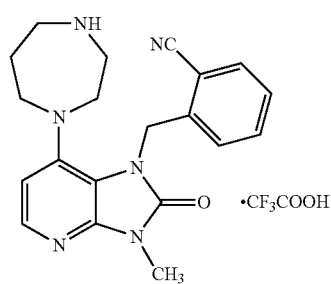 [SMILES: Cn1c(=O)n(Cc2ccccc2C#N)c2c(N3CCCNCC3)ccnc21 ; "·CF3COOH"]

The specific operation referred to the step (6) described in Example 1 for details. 4-[1-(2-cyanobenzyl)-3-methyl-2-oxo-2,3-dihydro-1H-imidazo[4,5-b]pyridin-7-yl]-1,4-homopiperazin-1-yl tert-butyl formate (0.285 g, 0.618 mmol) and 4 mL trifluoroacetic acid were charged to afford 0.238 g titled product with a yield of 80.9%.

Molecular formula: C$_{20}$H$_{22}$N$_6$O Molecular weight: 362.43
Mass spectrum (M+H): m/z: 363.2

1H-NMR (d6-DMSO-D2O, 400 MHz): δ8.00 (1H, d), 7.88 (1H, d), 7.60 (1H, t), 7.47 (1H, t), 7.07 (1H, d), 7.01 (1H, d), 5.41 (2H, s), 3.37 (3H, s), 3.23-3.21 (m, 2H), 3.18-3.15 (m, 2H), 3.01-2.94 (m, 4H), 1.76 (s, 2H).

Example 15

The preparation of 2-[[7-(3-aminohomopiperidin-1-yl)-3-methyl-2-oxo-2,3-dihydro-1H-imidazo[4,5-b]pyridin-1-yl]methyl]benzonitrile (Compound 15) trifluoroacetate

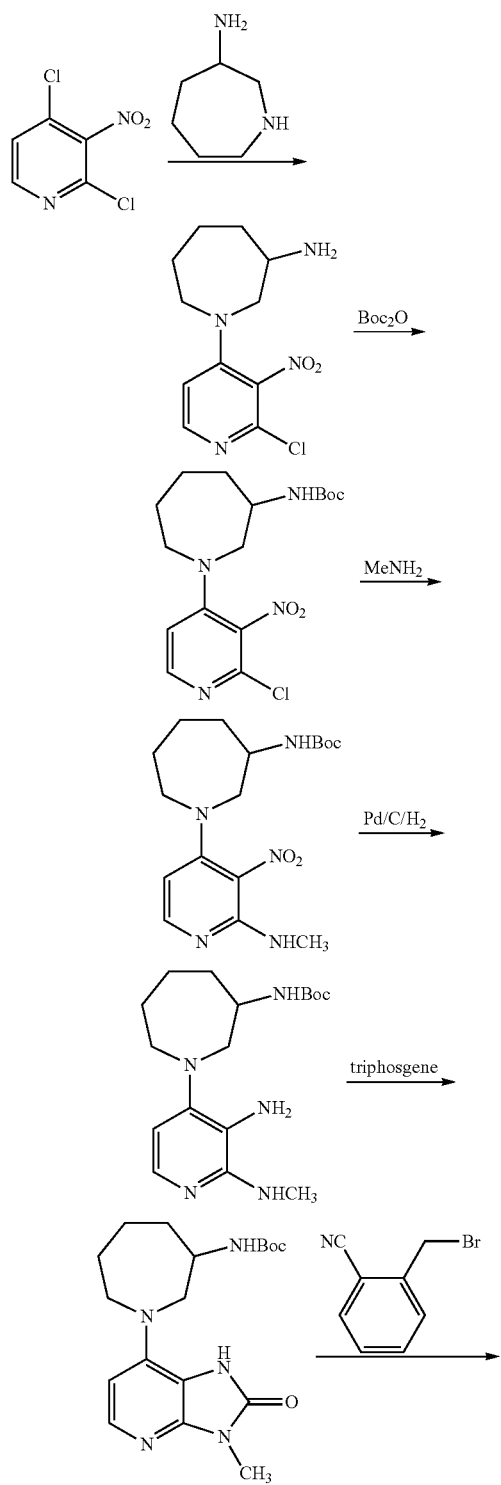

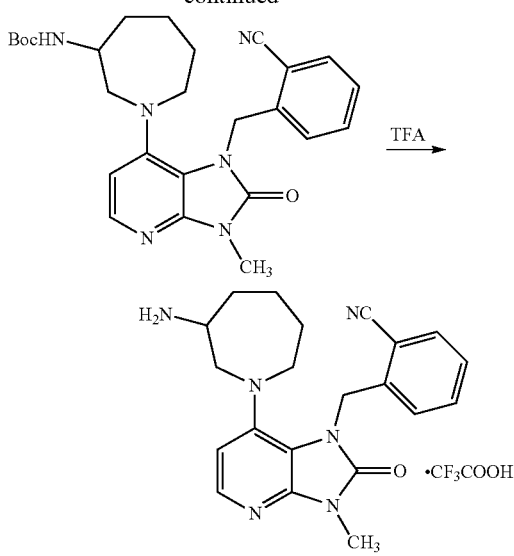

(1) 1-(2-chloro-3-nitropyridin-4-yl)-3-aminohomopiperidine

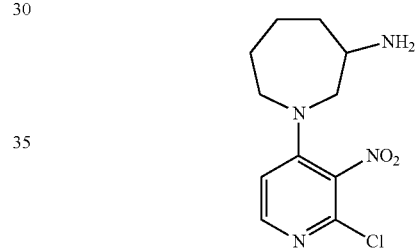

The specific operation referred to the step (1) described in Example 1 for details. 2,4-dichloro-3-nitropyridine (1.417 g, 7.38 mmol), and 3-aminohomopiperidine (0.914 g, 8.018 mmol) were charged to afford 2.765 g tilted product with a crude product yield of 100%.

(2) 1-(2-chloro-3-nitropyridin-4-yl)homopiperidin-3-yl tert-butyl carbamate

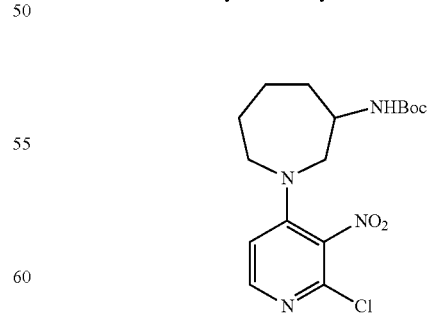

The specific operation referred to the step (2) described in Example 14 for details. 1-(2-chloro-3-nitropyridin-4-yl)-3-aminohomopiperidine (1.993 g, 7.38 mmol) and Di-tert-butyl dicarbonate (1.93 mL, 8.858 mmol) were charged. A column chromatography (EA:PE=1:6) was performed to afford 1.886 g yellow solid with a yield of 69.1%.

(3) 1-(2-methylamino-3-nitropyridin-4-yl)homopiperidin-3-yl tert-butyl carbamate

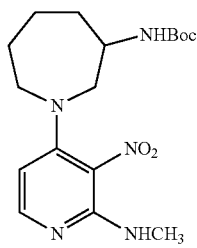 [SMILES: CNc1nccc(N2CCCCC(NC(=O)OC(C)(C)C)C2)c1[N+](=O)[O-]]

The specific operation referred to the step (2) described in Example 1 for details. 1-(2-chloro-3-nitropyridin-4-yl)homopiperidin-3-yl tert-butyl carbamate (1.882 g, 5.086 mmol) and 9.13 g 27% solution of methylamine in alcohol were charged to afford 1.59 g titled product with a yield of 85.7%.

(4) 1-(2-methylamino-3-aminopyridin-4-yl)homopiperidin-3-yl tert-butyl carbamate

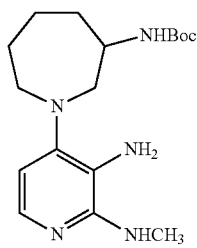 [SMILES: CNc1nccc(N2CCCCC(NC(=O)OC(C)(C)C)C2)c1N]

The specific operation referred to the step (3) described in Example 1 for details. 1-(2-methylamino-3-nitropyridin-4-yl)homopiperidin-3-yl tert-butyl carbamate (1.59 g, 4.356 mmol) and 0.159 g 10% Pd—C were charged to afford 1.446 g titled product with a yield of 99.1%.

(5) 1-(3-methyl-2-oxo-2,3-dihydro-1H-imidazo[4,5-b]pyridin-7-yl)-homopiperidin-3-yl tert-butyl carbamate

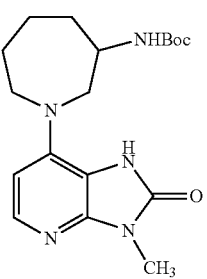

The specific operation referred to the step (4) described in Example 1 for details. 1-(2-methylamino-3-aminopyridin-4-yl)homopiperidin-3-yl tert-butyl carbamate (1.441 g, 4.301 mmol), triphosgene (1.403 g, 4.729 mmol), and triethylamine (2.4 mL, 17.24 mmol) were charged. A column chromatography (EA: $CH_2Cl_2$=1:1) was performed to afford 0.41 g titled product with a yield of 26.4%.

(6) 1-[1-(2-cyanobenzyl)-3-methyl-2-oxo-2,3-dihydro-1H-imidazo[4,5-b]pyridin-7-yl]-homopiperidin-3-yl tert-butyl carbamate

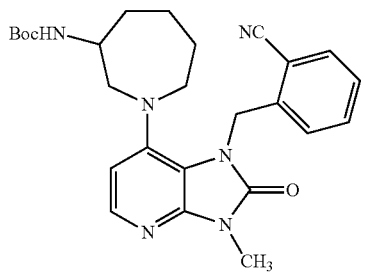 [SMILES: Cn1c(=O)n(Cc2ccccc2C#N)c2c(N3CCCCC(NC(=O)OC(C)(C)C)C3)ccnc21]

The specific operation referred to the step (5) described in Example 1 for details. 1-(3-methyl-2-oxo-2,3-dihydro-1H-imidazo[4,5-b]pyridin-7-yl)-homopiperidin-3-yl tert-butyl carbamate (0.41 g, 1.136 mmol), 2-(bromomethyl)benzonitrile (0.222 g, 1.138 mmol), and potassium carbonate (0.314 g, 2.275 mmol) were charged. A column chromatography (Ethyl acetate:Petroleum Ether=1:1) was performed to afford 0.255 g titled product with a yield of 47.1%.

(7) 2-[[7-(3-aminohomopiperidin-1-yl)-3-methyl-2-oxo-2,3-dihydro-1H-imidazo[4,5-b]pyridin-1-yl]methyl]benzonitrile trifluoroacetate

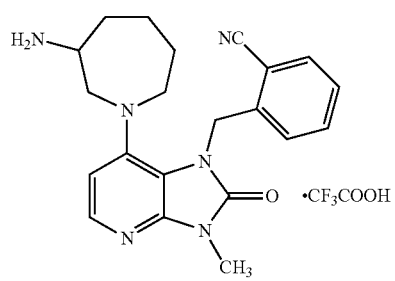 [SMILES: Cn1c(=O)n(Cc2ccccc2C#N)c2c(N3CCCCC(N)C3)ccnc21 ; "·CF3COOH"]

The specific operation referred to the step (6) described in Example 1 for details. 1-[1-(2-cyanobenzyl)-3-methyl-2-oxo-2,3-dihydro-1H-imidazo[4,5-b]pyridin-7-yl]-homopiperidin-3-yl tert-butyl carbamate (0.255 g, 0.536 mmol) and trifluoroacetic acid 3.7 mL were charged to afford 144 mg titled product with a yield of 71.5%.

Molecular formula: $C_{21}H_{24}N_6O$ Molecular weight: 376.45 Mass spectrum (M+H): m/z: 377.2

1H-NMR (d6-DMSO-$D_2O$, 400 MHz): δ 8.01 (1H, d), 7.90 (1H, d), 7.60 (1H, t), 7.47 (1H, t), 7.01 (1H, d), 6.98 (1H, m), 5.46 (2H, m), 3.38 (3H, s), 3.26-3.14 (m, 2H), 2.93-2.91 (m, 2H), 2.84-2.83 (m, 1H), 1.70-1.66 (m, 1H), 1.52-1.47 (m, 1H), 1.37 (br s, 1H), 1.22 (br s, 3H).

Example 16

The preparation of (R)-2-[[7-(3-aminopiperidin-1-yl)-3-methyl-2-oxo-2,3-dihydro-1H-imidazo[4,5-b]pyridin-1-yl]methyl]naphthonitrile (Compound 16) trifluoroacetate

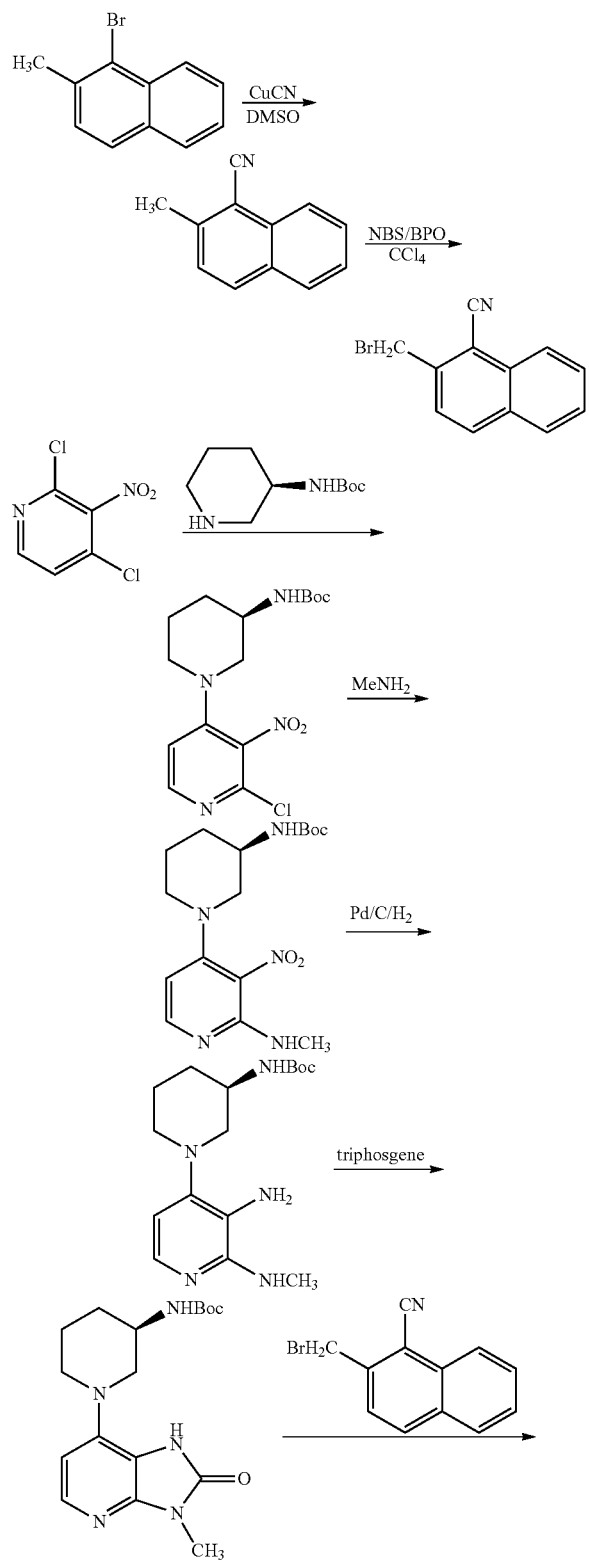

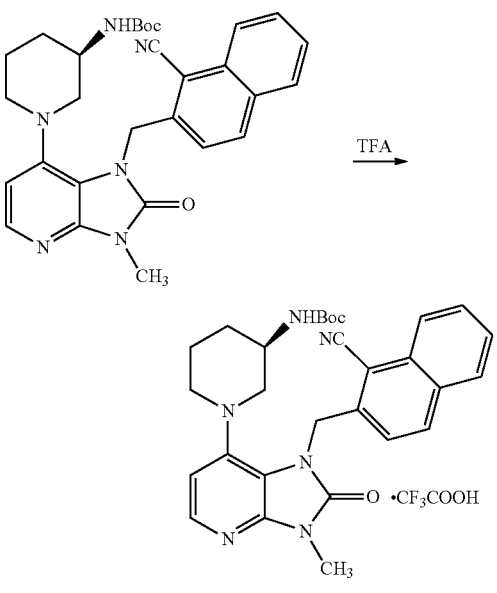

The steps (1)-(4) were same as the steps (1)-(4) described in the preparation example of Compound 1.

(5) 2-methyl-1-naphthonitrile

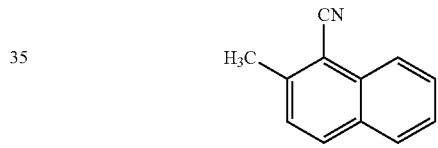

1-bromo-2-methylnaphthalene (4.42 g, 20 mmol) was dissolved in 25 mL DMSO, to which cuprous cyanide (1.8 g, 20 mmol) was added, reacted for 24 h at 120° C., and cooled to room temperature. About 100 mL water was added, and the solid was filtrated off. A column chromatography (Ethyl acetate:Petroleum Ether=5:1) was performed to afford 2.335 g white solid with a yield of 69.6%.

(6)-2-bromomethyl-1-naphthonitrile

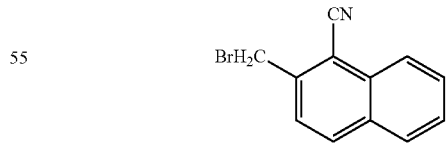

2-methyl-1-naphthonitrile (1.17 g, 7.00 mmol) was dissolved in 20 mL $CCl_4$. NBS (1.31 g, 7.36 mmol) and benzoyl peroxide (55 mg) were added, refluxed for 18 h, filtrated immediately when the reaction solution was hot, The filtrate was spinned to dryness, dissolved in 20 mL $CHCl_3$, washed with saturated sodium carbonate solution and water, and dried with anhydrous sodium sulfate. A column chromatography (Ethyl acetate:Petroleum Ether=5:1) was performed to afford 1.05 g white solid with a yield of 61.0%.

(7) (R)-1-[1-(1-cyano-2-naphthylmethylene)-3-methyl-2-oxo-2,3-dihydro-1H-imidazo[4,5-b]pyridin-7-yl]piperidin-3-yl tert-butyl carbamate

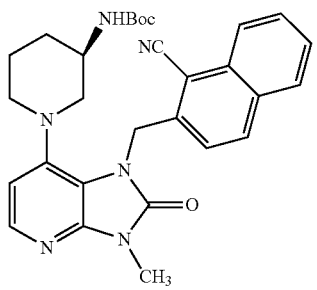 [SMILES: Cn1c(=O)n(Cc2ccc3ccccc3c2C#N)c2c(N3CCC[C@@H](NC(=O)OC(C)(C)C)C3)ccnc21]

The specific operation referred to the step (5) described in Example 1 for details. (R)-1-(3-methyl-2-oxo-2,3-dihydro-1H-imidazo[4,5-b]pyridin-7-yl)piperidin-3-yl tert-butyl carbamate (378 mg, 1.09 mmol), 2-bromomethyl-1-naphthonitrile (294 mg, 1.19 mmol), and potassium carbonate (310 mg, 2.25 mmol) were charged to afford 283 mg titled product with a yield of 50.4%.

(8) (R)-2-[[7-(3-aminopiperidin-1-yl)-3,5-dimethyl-2-oxo-2,3-dihydro-1H-imidazo[4,5-b]pyridin-1-yl]methyl]naphthonitrile trifluoroacetate

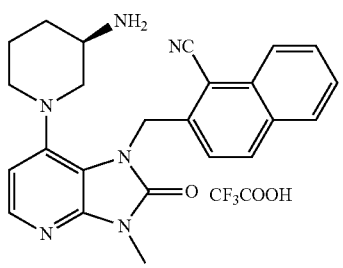 [SMILES: Cn1c(=O)n(Cc2ccc3ccccc3c2C#N)c2c(N3CCC[C@@H](N)C3)ccnc21 ; "CF3COOH"]

The specific operation referred to the step (6) described in Example 1 for details. (R)-1-[1-(1-cyano-2-naphthylmethylene)-3-methyl-2-oxo-2,3-dihydro-1H-imidazo[4,5-b]pyridin-7-yl]piperidin-3-yl tert-butyl carbamate (280 mg, 0.546 mmol) and 3.08 mL trifluoroacetic acid were charged to afford 220 mg titled product with a yield of 76.6%.

Molecular formula: $C_{24}H_{24}N_6O$ Molecular weight: 412.49 Mass spectrum (M+H): m/z: 413.2

$^1$H-NMR ($D_2O$, 400 MHz): δ 7.91 (m, 3H), 7.80 (s, 1H), 7.59 (d, 1H), 7.51 (d, 1H), 7.06 (t, 1H), 6.92 (d, 1H), 5.54 (t, 1H), 5.41 (t, 1H), 3.35 (s, 3H), 3.11 (d, 1H), 2.89 (s, 1H), 2.74 (m, 2H), 2.52 (d, 1H), 1.87 (d, 1H), 1.48 (d, 1H), 1.28 (m, 2H).

Example 17

The preparation of (R)-2-[[7-(3-aminopiperidin-1-yl)-3,5-dimethyl-2-oxo-2,3-dihydro-1H-imidazo[4,5-b]pyridin-1-yl]methyl]benzonitrile (Compound 17) trifluoroacetate

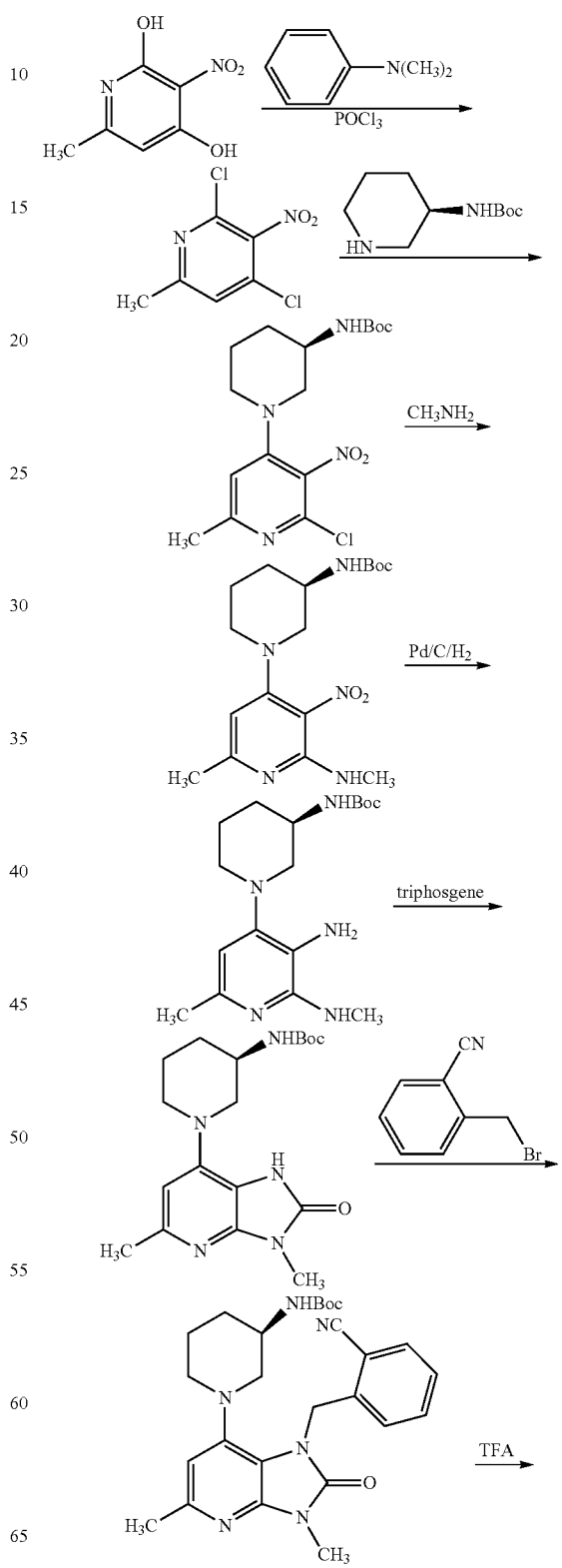

-continued

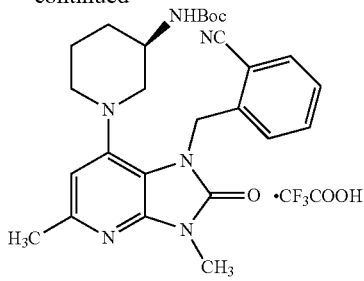

(1) 2,4-dichloro-6-methyl-3-nitropyridine

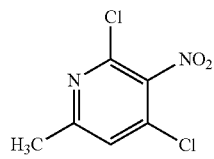

6-methyl-3-nitropyridin-2,4-diol (1.7 g, 10 mmol) was dissolved in 10 mL POCl₃, heated to 95° C., and stirred for 1.5 h. The excess POCl₃ was removed through centrifugation. 100 mL ice water was carefully added. The reaction solution was extracted with ethyl acetate (80 mL×3). The organic phase was combined, washed with saturated brine, dried with anhydrous Na₂SO₄, and spinned to dryness to afford 1.773 g yellow powder with a yield of 85.7%.

(2) (R)-1-(2-chloro-3-nitro-6-methylpyridin-4-yl)piperidin-3-yl tert-butyl carbamate

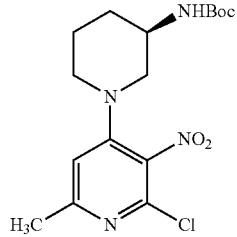

The specific operation referred to the step (1) described in Example 1 for details. 0.96 g 2,4-dichloro-6-methyl-3-nitropyridin (4.64 mmol), and 0.933 g R-tert-butylpiperidin-3-yl-carbamate (4.66 mmol) were charged to afford 1.1 g titled product with a yield of 63.9%.

(3) (R)-1-(2-methylamino-3-nitro-6-methylpyridin-4-yl)piperidin-3-yl tert-butyl carbamate

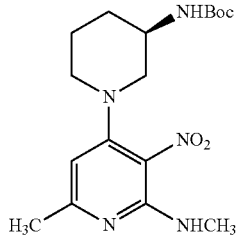 [SMILES: CNc1nc(C)cc(N2CCC[C@@H](NC(=O)OC(C)(C)C)C2)c1[N+](=O)[O-]]

The specific operation referred to the step (2) described in Example 1 for details. 1.1 g (R)-1-(2-chloro-3-nitro-6-methylpyridin-4-yl)piperidin-3-yl tert-butyl carbamate (2.97 mmol), and 5 mL 27% solution of methylamine in alcohol were charged to afford 1.0 g titled product with a yield of 92.1%.

(4) (R)-1-(2-methylamino-3-amino-6-methylpyridin-4-yl)piperidin-3-yl tert-butyl carbamate

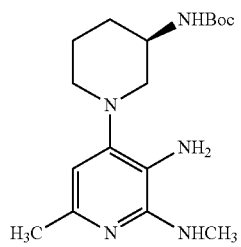

The specific operation referred to the step (3) described in Example 1 for details. 1.0 g (R)-1-(2-methylamino-3-nitro-6-methylpyridin-4-yl)piperidin-3-yl tert-butyl carbamate (2.74 mmol), and 0.1 g 10% Pd—C were charged to afford 0.873 g titled product with a yield of 95%.

(5) (R)-1-(3,5-dimethyl-2-oxo-2,3-dihydro-1H-imidazo[4,5-b]pyridin-7-yl)piperidin-3-yl tert-butyl carbamate

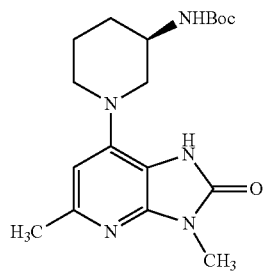 [SMILES: Cc1cc(N2CCC[C@@H](NC(=O)OC(C)(C)C)C2)c2[nH]c(=O)n(C)c2n1]

The specific operation referred to the step (4) described in Example 1 for details. 873 mg (R)-1-(2-methylamino-3-amino-6-methylpyridin-4-yl)piperidin-3-yl tert-butyl carbamate (2.60 mmol), 849 mg triphosgene (2.86 mmol), and 1.39 mL triethylamine (10.4 mmol) were charged to afford 0.813 g titled product with a yield of 86.5%.

(6) (R)-1-[1-(2-cyanobenzyl)-3,5-dimethyl-2-oxo-2,3-dihydro-1H-imidazo[4,5-b]pyridin-7-yl]piperidin-3-yl tert-butyl carbamate

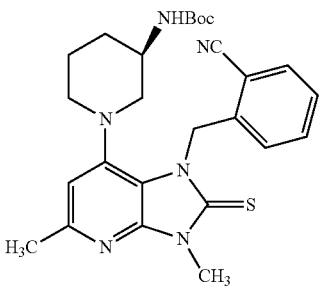 [SMILES: Cc1cc(N2CCC[C@@H](NC(=O)OC(C)(C)C)C2)c2c(n1)n(C)c(=S)n2Cc1ccccc1C#N]

The specific operation referred to the step (5) described in Example 1 for details. 813 mg (R)-1-(3,5-dimethyl-2-oxo-2,3-dihydro-1H-imidazo[4,5-b]pyridin-7-yl)piperidin-3-yl tert-butyl carbamate (2.25 mmol), 441 mg 2-(bromomethyl)

benzonitrile (2.25 mmol), and 621 mg potassium carbonate (4.50 mmol) were charged to afford 0.757 g titled product with a yield of 70.5%.

(7) (R)-2-[[7-(3-aminopiperidin-1-yl)-3,5-dimethyl-2-oxo-2,3-dihydro-1H-imidazo[4,5-b]pyridin-1-yl]methyl]benzonitrile trifluoroacetate

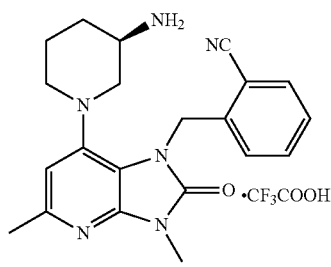 [SMILES: Cc1cc(N2CCC[C@@H](N)C2)c2c(n1)n(C)c(=O)n2Cc1ccccc1C#N ; "·CF3COOH"]

The specific operation referred to the step (6) described in Example 1 for details. 750 mg (R)-1-[1-(2-cyanobenzyl)-3,5-dimethyl-2-oxo-2,3-dihydro-1H-imidazo[4,5-b]pyridin-7-yl]piperidin-3-yl tert-butyl carbamate (1.57 mmol), and 8.5 mL trifluoroacetic acid were charged to afford 0.680 g titled product with a yield of 88.3%.

Molecular formula: $C_{21}H_{24}N_6O$ Molecular weight: 376.45
Mass spectrum (M+H): m/z: 377.2

$^1$H-NMR (D$_2$O, 400 MHz): δ 7.64 (d, 1H), 7.42 (t, 1H), 7.29 (d, 1H), 6.93 (d, 1H), 6.76 (s, 1H), 5.39 (d, 1H), 5.25 (d, 1H), 3.27 (s, 3H), 3.04 (m, 1H), 2.90 (m, 2H), 2.80-2.60 (m, 2H), 2.48 (m, 1H), 2.32 (s, 3H), 1.90 (m, 1H), 1.54 (m, 1H), 1.32 (m, 1H).

Example 18

The preparation of (R)-2-[[9-(3-aminopiperidin-1-yl)-3-methyl-2-oxo-2,3-dihydro-1H-imidazo[4,5-b]quinolin-1-yl]methyl]benzonitrile (Compound 18) trifluoroacetate

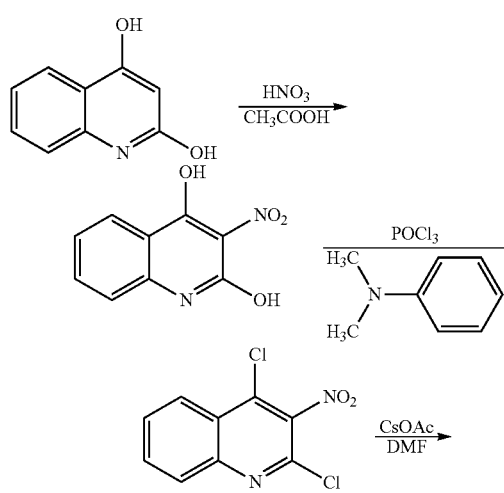
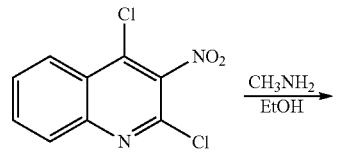
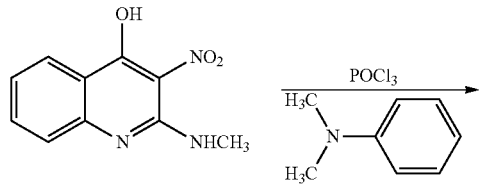
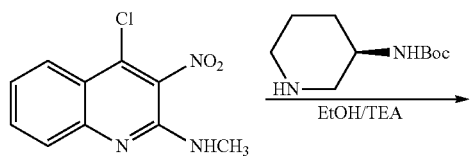
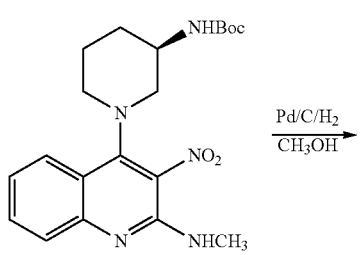
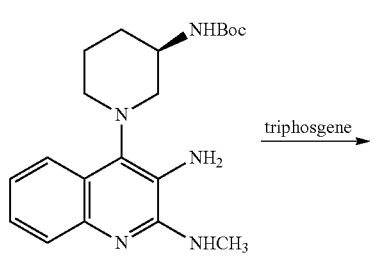
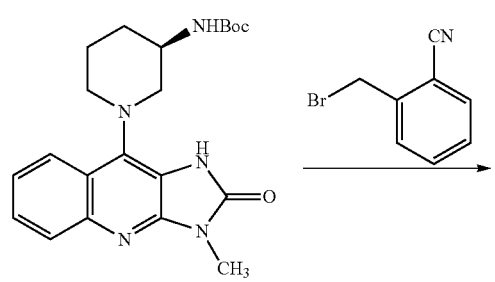
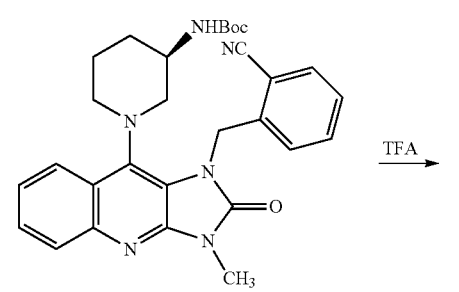

-continued

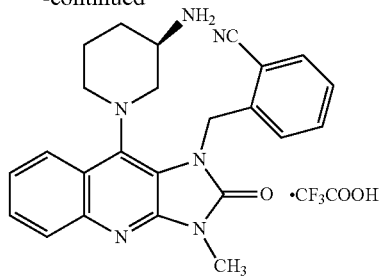

•CF₃COOH (1) 3-nitroquinoline-2,4-diol

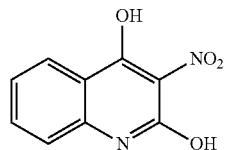 [SMILES: O=[N+]([O-])c1c(O)nc2ccccc2c1O]

To a 50 mL round bottom flask were sequentially added quinoline-2,4-diol (2 g, 12.4 mmol), glacial acetic acid 12.5 mL, and concentrated nitric acid 3.25 mL, stirred for 30 min at room temperature, and then stirred for 10 min in an oil bath of 105° C., followed by cooling to room temperature. 25 mL water was added to form precipitates, which were filtrated through an air pump, washed sequentially with water and ethyl ether. The solid was dried under vacuum to afford 2 g titled product with a yield of 78.2%.

(2) 2,4-dichloro-3-nitroquinoline

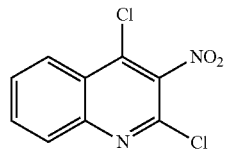

To a 20 mL round bottom flask were sequentially added 3-nitroquinoline-2,4-diol (1 g, 4.85 mmol), phosphorus oxychloride 5 mL, N,N-dimethylphenylamine 0.19 mL. And then, after reacting for 2 h at 90° C., the reaction solution was cooled to room temperature, poured into ice water and stirred for 0.5 h. The formed precipitates were subjected to suction filtration, dried overnight under vacuum, and the resultant solid was subjected to silica gel column chromatography (petroleum ether:ethyl acetate=5:1) to afford 0.7 g white solid with a yield of 59.4%.

(3)-2-chloro-3-nitroquinoline-4-ol

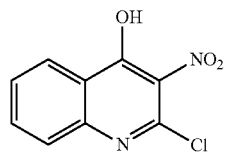 [SMILES: O=[N+]([O-])c1c(Cl)nc2ccccc2c1O]

To a 20 mL round bottom flask were sequentially added 2,4-dichloro-3-nitroquinoline (0.48 g, 1.97 mmol), 5 mL N,N-dimethylformamide, and cesium acetate (1.15 g, 6 mmol). After reacting for 14 h at 80° C., the reaction solution was cooled to room temperature, adjusted to pH=6 with 1 N hydrochloric acid. The formed precipitates were subjected to suction filtration, and the solid was dried under vacuum to afford 0.43 g titled product with a yield of 97.2%.

(4)-2-(methylamino)-3-nitroquinoline-4-ol

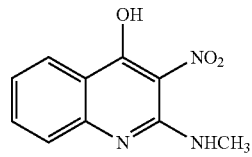 [SMILES: CNc1nc2ccccc2c(O)c1[N+](=O)[O-]]

To a 20 mL round bottom flask were sequentially added 2-chloro-3-nitroquinoline-4-ol (0.47 g, 2.09 mmol), 20 mL ethanol, and 0.8 mL 27% solution of methylamine in alcohol, refluxed and stirred for 14 h. The solution was cooled to room temperature and was concentrated to afford 0.4 g of titled product with a yield of 87.3%.

(5)-4-chloro-N-methyl-3-nitroquinoline-2-amine

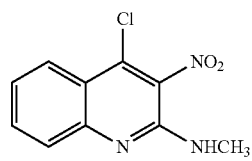 [SMILES: CNc1nc2ccccc2c(Cl)c1[N+](=O)[O-]]

To a 20 mL round bottom flask were sequentially added 2-(methylamino)-3-nitroquinoline-4-ol (0.35 g, 1.60 mmol), 0.825 mL phosphorus oxychloride, and 0.03 mL N,N-dimethyl phenylamine. And then, after reacting for 2 h at 90° C., the reaction solution was cooled to room temperature, poured into ice water, adjusted to pH=8 with saturated sodium carbonate solution, and then extracted with ethyl acetate (100 mL×3). The organic phase was dried with anhydrous sodium sulfate, and concentrated. The resultant crude product was subjected to silica gel column chromatography (dichloromethane:petroleum ether=3:1) to afford 0.26 g white solid with a yield of 68.4%.

(6) (R)-1-[2-(methylamino)-3-nitroquinolin-4-yl] piperidin-3-yl tert-butyl carbamate

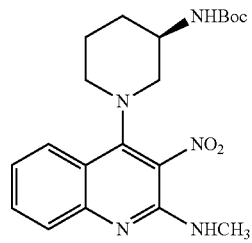 [SMILES: CNc1nc2ccccc2c(N2CCC[C@@H](NC(=O)OC(C)(C)C)C2)c1[N+](=O)[O-]]

To 15 mL solution of 4-chloro-N-methyl-3-nitroquinoline-2-amine (0.26 g, 1.09 mmol) in ethanol was added triethylamine (0.3 mL, 2.2 mmol), and stirred in an ice bath. After 10 mL solution of (R)-tert-butylpiperidin-3-yl-carbamate (0.22 g, 1.1 mmol) in ethanol was slowly added dropwise with a constant pressure funnel, the reaction solution was stirred for 14 h at room temperature, and concentrated. The resultant crude product was subjected to silica gel column chromatography (ethyl acetate:petroleum ether=1:3) to afford 0.27 g titled product with a yield of 61.7%.

(7) (R)-1-[3-amino-2-(methylamino)quinolin-4-yl]piperidin-3-yl tert-butyl carbamate

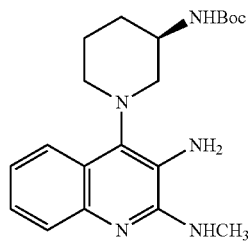 [SMILES: CNc1nc2ccccc2c(N2CCC[C@@H](NC(=O)OC(C)(C)C)C2)c1N]

In a dry reaction bottle, (R)-1-[2-(methylamino)-3-nitroquinolin-4-yl]piperidin-3-yl tert-butyl carbamate (282 mg, 0.702 mmol) was added, and dissolved in 10 mL methanol. 0.03 g 10% Pd—C was added at room temperature, into which hydrogen gas was introduced, and stirred for 3 h. The reaction solution was filtrated, concentrated, and dried under vacuum to afford 224 mg red solid with a yield of 85.9%.

(8) (R)-1-(3-methyl-2-oxo-2,3-dihydro-1H-imidazo[4,5-b]quinolin-9-yl)piperidin-3-yl tert-butyl carbamate

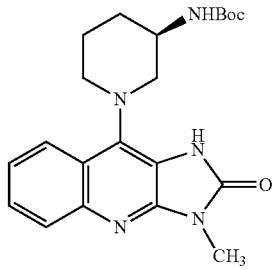 [SMILES: Cn1c(=O)[nH]c2c(N3CCC[C@@H](NC(=O)OC(C)(C)C)C3)c3ccccc3nc21]

In a dry reaction bottle, triphosgene (197 mg, 1.65 mmol) and triethylamine (0.37 mL, 2.65 mmol) were dissolved in 50 mL tetrahydrofuran. A solution of (R)-1-[3-amino-2-(methylamino)quinolin-4-yl]piperidin-3-yl tert-butyl carbamate (224 mg, 0.603 mmol) in 10 mL tetrahydrofuran was slowly added dropwise with a constant pressure funnel at −10° C. The reaction solution was stirred for 0.5 h, adjusted to pH=8 with saturated sodium carbonate solution, and then extracted with ethyl acetate (100 mL×3). The organic phase was dried with anhydrous sodium sulfate, and concentrated to afford 0.239 g solid with a yield of 100%.

(9) (R)-1-[1-(2-cyanobenzyl)-3-methyl-2-oxo-2,3-dihydro-1H-imidazo[4,5-b]quinolin-9-yl]piperidin-3-yl tert-butyl carbamate

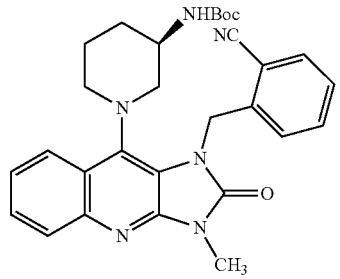 [SMILES: Cn1c(=O)n(Cc2ccccc2C#N)c2c(N3CCC[C@@H](NC(=O)OC(C)(C)C)C3)c3ccccc3nc21]

In a dry reaction bottle, (R)-1-(3-methyl-2-oxo-2,3-dihydro-1H-imidazo[4,5-b]quinolin-9-yl)piperidin-3-yl tert-butyl carbamate (239 mg, 0.601 mmol) was added, and dissolved in 2 mL DMF. 179 mg 2-(bromomethyl)benzonitrile (0.91 mmol), and 253 mg potassium carbonate (1.82 mmol) were added dropwise at −10° C. The reaction was continued for 1 h while stirring at room temperature. The reaction solution was exacted by ethyl acetate, and washed with saturated sodium chloride solution, The organic layer was dried with anhydrous sodium sulfate, and purified through a silica gel column chromatography (dichloromethane:ethyl acetate=10:1) to afford 142 mg white powder with a yield of 46.1%.

(10) (R)-2-[[9-(3-aminopiperidin-1-yl)-3-methyl-2-oxo-2,3-dihydro-1H-imidazo[4,5-b]quinolin-1-yl]methyl]benzonitrile trifluoroacetate

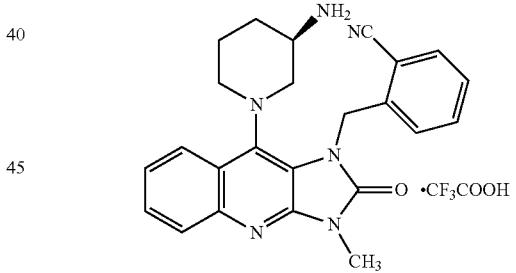

In a dry reaction bottle, (R)-1-[1-(2-cyanobenzyl)-3-methyl-2-oxo-2,3-dihydro-1H-imidazo[4,5-b]quinolin-9-yl]piperidin-3-yl tert-butyl carbamate (142 mg, 0.277 mmol) was added and dissolved in 5 mL $CH_2Cl_2$. 3 mL trifluoroacetic acid was added dropwise at 0° C. The reaction solution was stirred for 1 h at room temperature. The reaction solution was evaporated to dryness. The residue was dissolved in a small amount of methanol and ethyl ether to afford a white solid. The resultant product was 110.5 mg with a yield of 75.8%.

Molecular formula: $C_{24}H_{24}N_6O$ Molecular weight: 412.49
Mass spectrum (M+H): m/z: 413.2

$^1$H-NMR ($D_2O$, 400 MHz): δ 8.01 (d, 1H), 7.84 (d, 1H), 7.78 (d, 1H), 7.53 (m, 2H), 7.39 (dd, 2H), 7.02 (d, 1H), 5.54 (d, 1H), 5.32 (d, 1H), 3.42 (s, 3H), 3.32 (t, 2H), 2.91 (d, 1H), 2.67 (d, 1H), 1.86 (m, 2H), 1.58 (d, 1H), 1.31 (m, 1H), 1.06 (m, 1H).

Example 19

The preparation of (R)-2-[[7-(3-aminopiperidin-1-yl)-2-oxo-2,3-dihydro-1H-imidazo[4,5-b]pyridin-1-yl]methyl]benzonitrile (Compound 19) trifluoroacetate

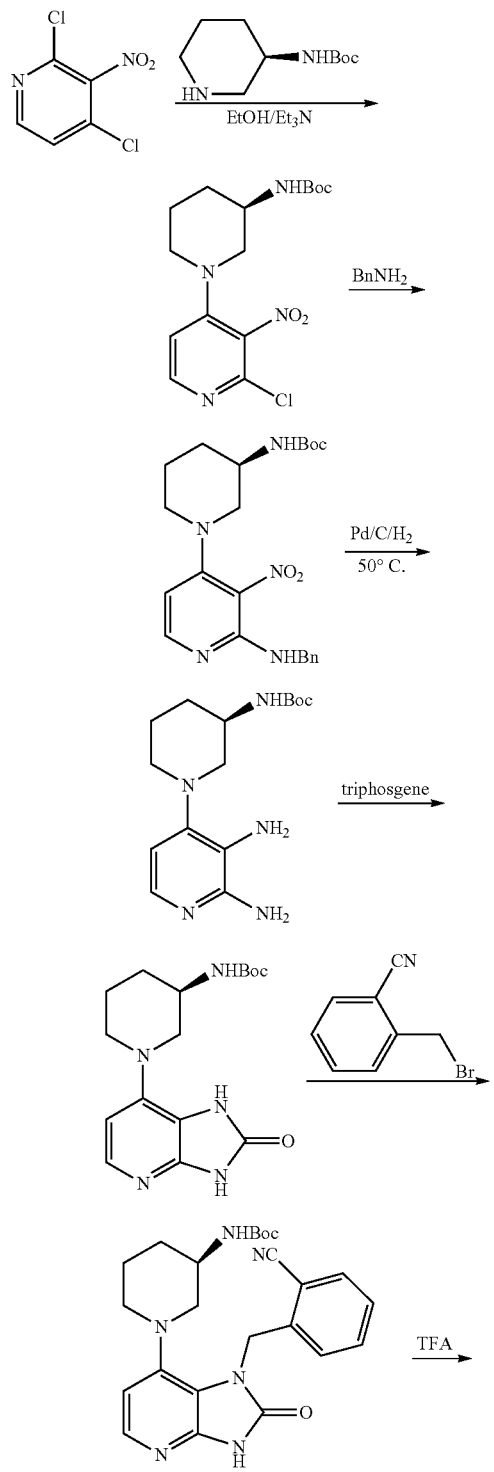

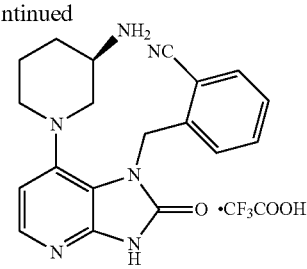

(1) (R)-1-(2-chloro-3-nitropyridin-4-yl)piperidin-3-yl tert-butyl carbamate

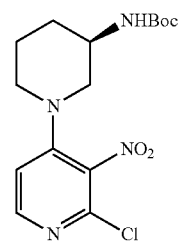 [SMILES: CC(C)(C)OC(=O)N[C@@H]1CCCN(c2ccnc(Cl)c2[N+](=O)[O-])C1]

The operation referred to the step (1) described in Example 1. 907 mg product was obtained with a yield of 85.0%.

(2) (R)-1-[2-(benzylamino)-3-nitropyridin-4-yl]piperidin-3-yl tert-butyl carbamate

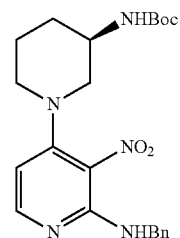

In a dry reaction bottle, 1.07 g (R)-1-(2-chloro-3-nitropyridin-4-yl)piperidin-3-yl tert-butyl carbamate (3.0 mmol) was added and dissolved in 10 mL ethanol, to which 0.49 mL (4.5 mmol) benzylamine was added, and stirred for 48 h at 90° C. The reaction solution was concentrated and subjected to column chromatography to afford 1.2 g titled product with a yield of 93.6%.

(3) (R)-1-(2,3-diaminopyridin-4-yl)piperidin-3-yl tert-butyl carbamate

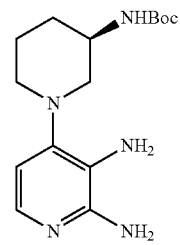 [SMILES: CC(C)(C)OC(=O)N[C@@H]1CCCN(c2ccnc(N)c2N)C1]

In a dry reaction bottle, 800 mg (R)-1-[2-(benzylamino)-3-nitropyridin-4-yl]piperidin-3-yl tert-butyl carbamate (1.87 mmol) was added and dissolved in 13 mL ethanol, to which 0.2 g 10% Pd—C was added at room temperature, and hydrogen gas was introduced. The reaction was continued overnight at 50° C. The reaction solution was filtrated, concentrated, dissolved in CH₂Cl₂, washed with water and saturated brine, dried, and concentrated to afford 455 mg titled product with a yield of 79.1%.

(4) (R)-1-(2-oxo-2,3-dihydro-1H-imidazo[4,5-b]pyridin-7-yl)piperidin-3-yl tert-butyl carbamate

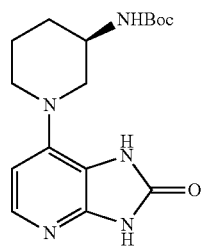 [SMILES: CC(C)(C)OC(=O)N[C@@H]1CCCN(c2ccnc3[nH]c(=O)[nH]c23)C1]

In a dry reaction bottle, 489 mg triphosgene (1.65 mmol), and 0.83 mL (6.0 mmol) triethylamine were added and dissolved in 50 mL tetrahydrofuran. 0.455 g (R)-1-(2,3-diaminopyridin-4-yl)piperidin-3-yl tert-butyl carbamate (1.48 mmol) was added at −10° C., dissolved in 10 mL tetrahydrofuran, and stirred for 0.5 h. The reaction solution was exacted with ethyl acetate, washed with saturated sodium carbonate solution and strong brine. The organic layer was dried with anhydrous sodium sulfate, and concentrated to afford 314 mg titled product with a yield of 63.6%.

(5) (R)-1-[1-(2-cyanobenzyl)-2-oxo-2,3-dihydro-1H-imidazo[4,5-b]pyridin-7-yl]piperidin-3-yl tert-butyl carbamate

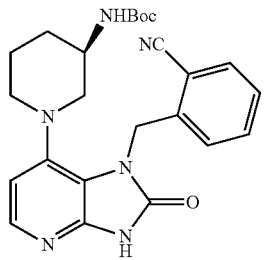 [SMILES: CC(C)(C)OC(=O)N[C@@H]1CCCN(c2ccnc3[nH]c(=O)n(Cc4ccccc4C#N)c23)C1]

In a dry reaction bottle, (R)-1-(2-oxo-2,3-dihydro-1H-imidazo[4,5-b]pyridin-7-yl)piperidin-3-yl tert-butyl carbamate (314 mg, 0.942 mmol) was added and dissolved in 2 mL DMF. 204 mg 2-(bromomethyl)benzonitrile (1.04 mmol) and 195 mg potassium carbonate (1.41 mmol) were added at 0° C. The reaction was continued for 1 h by stirring at room temperature. The reaction solution was exacted with ethyl acetate, washed with saturated sodium chloride solution. The organic layer was dried with anhydrous sodium sulfate, and purified through a column chromatography (petroleum ether: ethyl acetate=1:2) to afford 120 mg titled product with a yield of 28.5%.

(6) (R)-2-[[7-(3-aminopiperidin-1-yl)-2-oxo-2,3-dihydro-1H-imidazo[4,5-b]pyridin-1-yl]methyl]benzonitrile trifluoroacetate

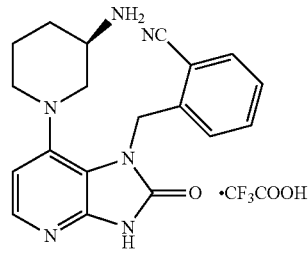 [SMILES: N#Cc1ccccc1Cn1c(=O)[nH]c2nccc(N3CCC[C@@H](N)C3)c21 ; "·CF3COOH"]

The operation referred to the step (6) described in Example 1 for details. 120 mg (R)-1-[1-(2-cyanobenzyl)-2-oxo-2,3-dihydro-1H-imidazo[4,5-b]pyridin-7-yl]piperidin-3-yl tert-butyl carbamate (0.268 mmol) and 1.8 mL trifluoroacetic acid were added to afford 82 mg titled product with a yield of 66.0%.

Molecular formula: $C_{19}H_{20}N_6O$ Molecular weight: 348.40
Mass spectrum (M+H): m/z: 349.2

$^1$H-NMR (D₂O, 400 MHz): δ 7.89 (d, 1H), 7.72 (d, 1H), 7.50 (m, 1H), 7.36 (t, 1H), 7.05 (d, 1H), 6.97 (d, 1H), 5.44 (d, 1H), 5.33 (d, 1H), 3.23 (s, 1H), 3.20 (s, 1H), 3.03 (m, 1H), 2.92 (d, 1H), 2.80 (t, 1H), 2.63 (m, 1H), 1.97 (m, 1H), 1.62 (m, 1H), 1.38 (m, 2H).

Example 20

The preparation of 2-[[7-(3-aminoazetidin-1-yl)-3-methyl-2-oxo-2,3-dihydro-1H-imidazo[4,5-b]pyridin-1-yl]methyl]benzonitrile (Compound 20) trifluoroacetate

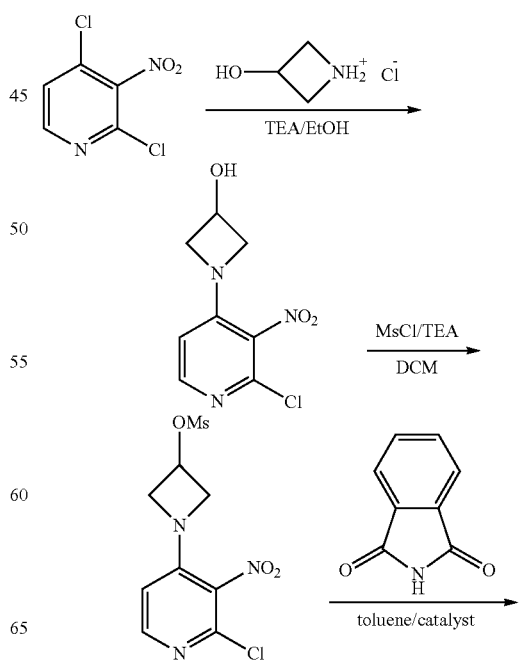

-continued

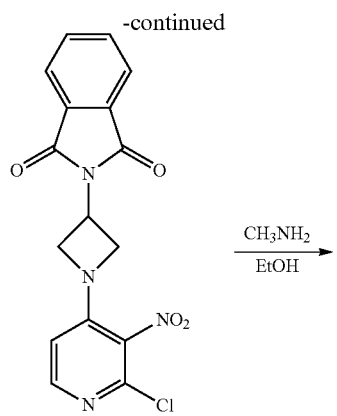

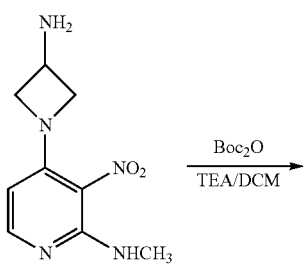

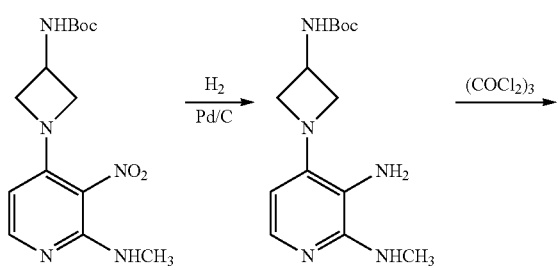

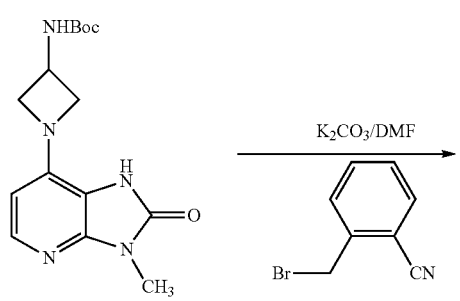

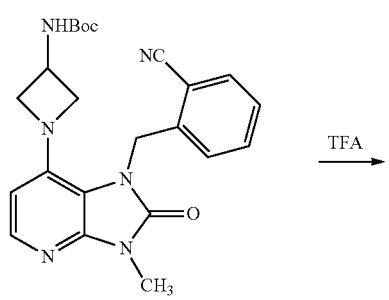

-continued

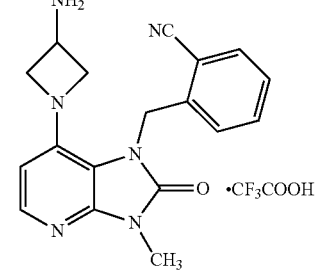

(1) 1-(2-chloro-3-nitropyridin-4-yl)azetidine-3-ol

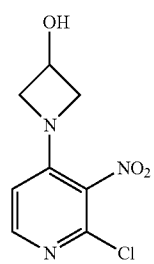

In a dry reaction bottle, 10 mL ethanol, 1 g 2,4-dichloro-3-nitropyridine (5.18 mmol), 1.38 g 3-hydroxyazetidine hydrochlorate (12.75 mmol), and 1.38 mL triethylamine were added, and stirred for 16 h at room temperature. A yellow solid was precipitated from the reaction solution. The reaction solution was subjected to suction filtration to afford 780 mg titled product with a yield of 65.6%.

(2) 1-(2-chloro-3-nitropyridin-4-yl)azetidine-3-methanesulfonate

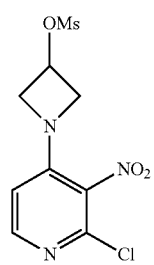

In a dry reaction bottle were sequentially added 30 mL dichloromethane, 0.459 g 1-(2-chloro-3-nitropyridin-4-yl)azetidine-3-ol (2 mmol), and 1 mL triethylamine, and stirred for 0.5 h in an ice bath. 0.19 mL methanesulfonyl chloride was slowly added dropwise with a constant pressure funnel. After the reaction solution was stirred for 2 h in an ice bath, 30 mL water was added. The reaction solution was extracted with dichloromethane (100 mL×3), dried with anhydrous sodium sulfate, and concentrated to afford 0.6 g crude product with a yield of 97.5%.

(3)-2-[1-(2-chloro-3-nitropyridin-4-yl)azetidin-3-yl]isodihydroindole-1,3-dione

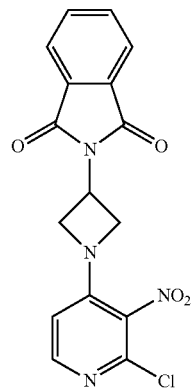 [SMILES: O=C1c2ccccc2C(=O)N1C1CN(c2ccnc(Cl)c2[N+](=O)[O-])C1]

To 30 mL toluene were sequentially added 1-(2-chloro-3-nitropyridin-4-yl)azetidine-3-methanesulfonate (1.53 g, 5 mmol), phthalimide potassium salt (1.13 g, 6.05 mmol) and hexadecyltributylphosphonium bromide (0.313 g, 0.62 mmol). The reaction solution was refluxed and stirred for 6 h, cooled to room temperature, and subjected to suction filtration. The resultant precipitate was washed with ethyl acetate. The organic phase was combined, washed with water, dried with anhydrous sodium sulfate, concentrated, and subjected to silica gel column chromatography (dichloromethane:ethyl acetate=9:1) to afford 0.25 g yellow solid with a yield of 14%.

(4)-4-(3-aminoazetidin-1-yl)-N-methyl-3-nitropyridine-2-amine

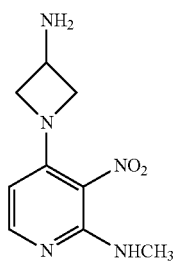 [SMILES: CNc1nccc(N2CC(N)C2)c1[N+](=O)[O-]]

In a dry reaction bottle, 0.25 g 2-[1-(2-chloro-3-nitropyridin-4-yl)azetidin-3-yl]isodihydroindole-1,3-dione (0.7 mmol) was added and dissolved in 10 mL ethanol. 1 mL 27% solution of methylamine in ethanol was added, and stirred for 24 h at 110° C. The reaction solution was dried under a reduced pressure to afford 245 mg crude product as yellow solid.

(5)1-[2-(methylamino)-3-nitropyridin-4-yl]azetidine-3-tert-butyl carbamate

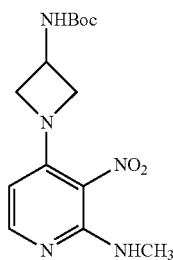

To 10 mL solution of 4-(3-aminoazetidin-1-yl)-N-methyl-3-nitropyridine-2-amine (0.245 g crude sample, 0.7 mmol) in dichloromethane were added 0.2 mL triethylamine and Di-tert-butyl dicarbonate (0.183 g, 0.84 mmol). The reaction solution was stirred for 5 h at room temperature. The resultant reaction solution was dried under a reduced pressure. The resultant crude product was subjected to silica gel column chromatography (ethyl acetate) to afford 0.22 g yellow solid with a yield of 97.1%.

(6)1-[3-amino-2-(methylamino)pyridin-4-yl]azetidine-3-tert-butyl carbamate

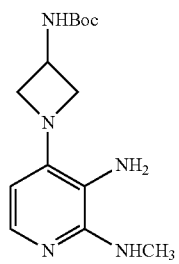

In a dry reaction bottle, 1-[2-(methylamino)-3-nitropyridin-4-yl]azetidine-3-tert-butyl carbamate (220 mg, 0.68 mmol) was added and dissolved in 10 mL methanol, to which 0.02 g 10% Pd—C was added at room temperature, and hydrogen gas was introduced. The stirring was continued for 3 h. The reaction solution was filtrated. The solvent was removed through evaporation under a reduced pressure to afford 199 mg red solid with a yield of 100%.

(7)1-(3-methyl-2-oxo-2,3-dihydro-1H-imidazo[4,5-b]pyridin-7-yl)azetidin-3-yl tert-butyl carbamate

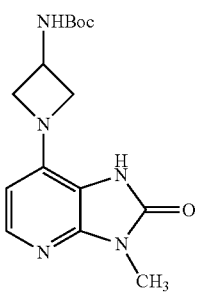 [SMILES: Cn1c(=O)[nH]c2c(N3CC(NC(=O)OC(C)(C)C)C3)ccnc21]

In a dry reaction bottle, triphosgene (185 mg, 0.93 mol) and 0.83 mL triethylamine (6.0 mmol) were added and dissolved in 50 mL tetrahydrofuran. A solution of 1-[3-amino-2-(methylamino)pyridin-4-yl]azetidine-3-tert-butyl carbamate (250 mg, 0.85 mmol) in 10 mL tetrahydrofuran was added at −10° C., and stirred for 0.5 h. The reaction solution was exacted with ethyl acetate, and washed with saturated sodium carbonate solution and saturated brine. The organic layer was dried with anhydrous sodium sulfate, and purified through a column chromatography to afford 200 mg white powder with a yield of 73.6%.

(8)1-[1-(2-cyanobenzyl)-3-methyl-2-oxo-2,3-dihydro-1H-imidazo[4,5-b]pyridin-7-yl]azetidin-3-yl tert-butyl carbamate

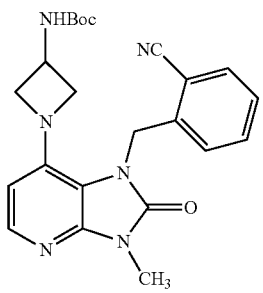

In a dry reaction bottle, 1-(3-methyl-2-oxo-2,3-dihydro-1H-imidazo[4,5-b]pyridin-7-yl)azetidin-3-yl tert-butyl carbamate (200 mg, 0.626 mmol) was added and dissolved in 2 mL DMF. 2-(bromomethyl)benzonitrile (123 mg, 0.626 mmol) and 173 mg potassium carbonate (1.254 mmol) were added dropwise at −10° C. The reaction was continued for 1 h by stirring at room temperature. The reaction solution was exacted with ethyl acetate, and washed with saturated sodium chloride solution. The organic layer was dried with anhydrous sodium sulfate, and purified through a column chromatography (petroleum ether:ethyl acetate=1:1) to afford 78 mg white powder with a yield of 28.8%.

(9)2-[[7-(3-aminoazetidin-1-yl)-3-methyl-2-oxo-2,3-dihydro-1H-imidazo[4,5-b]pyridin-1-yl]methylene]benzonitrile trifluoroacetate

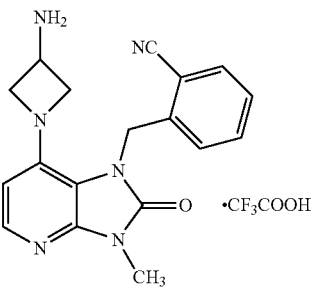 [SMILES: Cn1c(=O)n(Cc2ccccc2C#N)c2c(N3CC(N)C3)ccnc21 ; "·CF3COOH"]

The operation referred to the step (6) described in Example 1. 1-[1-(2-cyanobenzyl)-3-methyl-2-oxo-2,3-dihydro-1H-imidazo[4,5-b]pyridin-7-yl]azetidin-3-yl tert-butyl carbamate (78 mg, 0.18 mmol) and 1.2 mL trifluoroacetic acid were charged to afford 51 mg titled product with a yield of 63.3%.

Molecular formula: $C_{18}H_{18}N_6O$ Molecular weight: 334.38
Mass spectrum (M+H): m/z: 335.1

1H-NMR (D$_2$O, 400 MHz): δ7.83 (d, 1H), 7.73 (d, 1H), 7.52 (t, 1H), 7.37 (t, 1H), 7.12 (d, 1H), 6.50 (d, 1H), 5.34 (s, 2H), 4.14 (t, 2H), 3.99 (m, 1H), 3.84 (m, 2H), 3.32 (s, 3H).

Example 21

The preparation of (R)-2-[[7-(3-aminopyrrolidin-1-yl)-3,5-dimethyl-2-oxo-2,3-dihydro-1H-imidazo[4,5-b]pyridin-1-yl]methyl]benzonitrile (Compound 21) trifluoroacetate

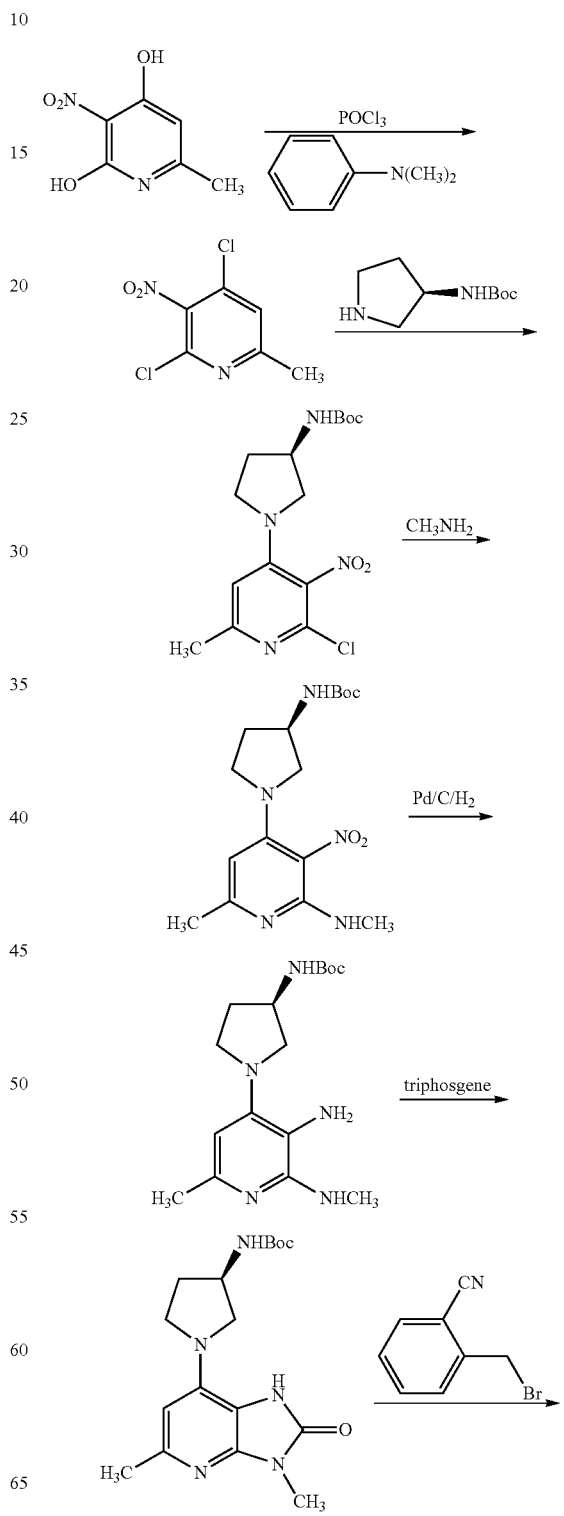

-continued

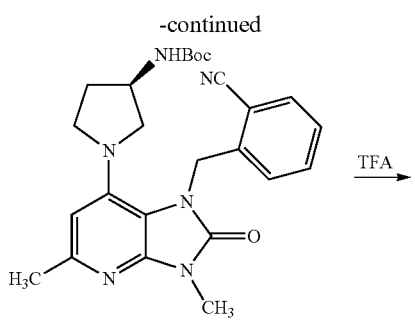

↓ TFA

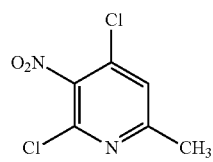

(1) 2,4-dichloro-6-methyl-3-nitropyridine

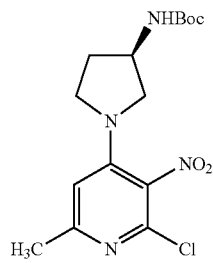 [SMILES: Cc1cc(N2CC[C@@H](NC(=O)OC(C)(C)C)C2)c([N+](=O)[O-])c(Cl)n1]

6-methyl-3-nitropyridine-2,4-diol (1.7 g, 10 mM) was dissolved in 10 mL POCl₃, heated to 95° C., and stirred for 1.5 h. The excess POCl₃ was removed through centrifugation. The reaction was quenched by carefully adding ice water. The reaction solution was extracted with ethyl acetate. The organic phase was combined, washed with saturated brine, dried with anhydrous Na₂SO₄, and spinned to dryness to afford 1.34 g yellow powder with a yield of 64.7%.

(2) (R)-1-(2-chloro-3-nitro-6-methylpyridin-4-yl)pyrrolidin-3-yl tert-butyl carbamate

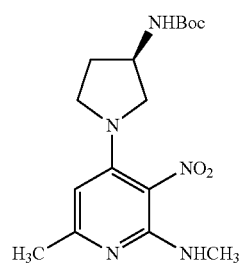

The operation referred to the step (1) described in Example 1. 1.34 g 2,4-dichloro-6-methyl-3-nitropyridine (6.47 mmol), 1.21 g (R)-pyrrolidin-3-yl tert-butyl carbamate (6.5 mmol), and 1.81 mL triethylamine were charged to afford 1.7 g titled product with a yield of 73.6%.

(3) (R)-1-(2-methylamino-3-nitro-6-methylpyridin-4-yl)pyrrolidin-3-yl tert-butyl carbamate

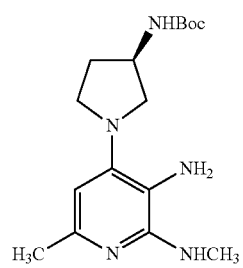

The specific operation referred to the step (2) described in Example 1 for details. 1.7 g (R)-1-(2-chloro-3-nitro-6-methylpyridin-4-yl)pyrrolidin-3-yl tert-butyl carbamate (4.76 mmol) was charged to afford 1.65 g titled product with a yield of 98.6%.

(4) (R)-1-(2-methylamino-3-amino-6-methylpyridin-4-yl)pyrrolidin-3-yl tert-butyl carbamate

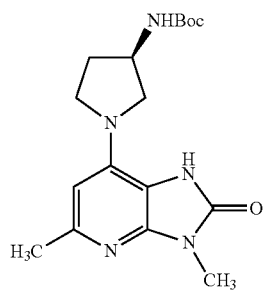 [SMILES: Cc1cc(N2CC[C@@H](NC(=O)OC(C)(C)C)C2)c2[nH]c(=O)n(C)c2n1]

The specific operation referred to the step (3) described in Example 1 for details. 1.65 g (R)-1-(2-methylamino-3-nitro-6-methylpyridin-4-yl)pyrrolidin-3-yl tert-butyl carbamate (4.70 mmol) was charged to afford 1.4 g titled product with a yield of 92.7%.

(5) (R)-1-(3,5-dimethyl-2-oxo-2,3-dihydro-1H-imidazo[4,5-b]pyridin-7-yl)pyrrolidin-3-yl tert-butyl carbamate The specific operation referred to the step (4) described in Example 1 for details. 1.4 g (R)-1-(2-methylamino-3-amino- 6-methylpyridin-4-yl)pyrrolidin-3-yl tert-butyl carbamate (4.36 mmol) was charged to afford 1.4 g white powder with a yield of 92.5%.

(6) (R)-1-[1-(2-cyanobenzyl)-3,5-dimethyl-2-oxo-2, 3-dihydro-1H-imidazo[4,5-b]pyridin-7-yl]pyrrolidin-3-yl tert-butyl carbamate

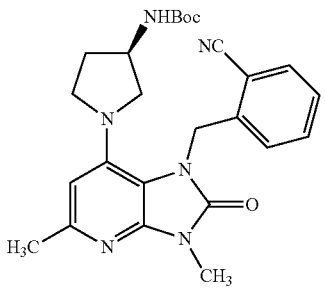 [SMILES: Cc1cc(N2CC[C@@H](NC(=O)OC(C)(C)C)C2)c2c(n1)n(C)c(=O)n2Cc1ccccc1C#N]

The specific operation referred to the step (5) described in Example 1 for details. (R)-1-(3,5-dimethyl-2-oxo-2,3-dihydro-1H-imidazo[4,5-b]pyridin-7-yl)pyrrolidin-3-yl tert-butyl carbamate (1.4 g, 4.03 mmol) was charged to afford 1.05 g white powder with a yield of 56.3%.

(7) (R)-2-[[7-(3-aminopyrrolidin-1-yl)-3,5-dimethyl-2-oxo-2,3-dihydro-1H-imidazo[4,5-b]pyridin-1-yl] methyl]benzonitrile trifluoroacetate

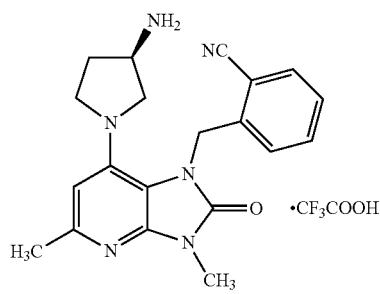 [SMILES: Cc1cc(N2CC[C@@H](N)C2)c2c(n1)n(C)c(=O)n2Cc1ccccc1C#N ; "·CF3COOH"]

The specific operation referred to the step (6) described in Example 1 for details. 1.05 g (R)-1-[1-(2-cyanobenzyl)-3,5-dimethyl-2-oxo-2,3-dihydro-1H-imidazo[4,5-b]pyridin-7-yl]pyrrolidin-3-yl tert-butyl carbamate (2.27 mmol) was charged to afford 770 mg titled product with a yield of 71.2%.

Molecular formula: $C_{20}H_{22}N_6O$ Molecular weight: 362.43 Mass spectrum (M+H): m/z: 363.2

$^1$H-NMR (DMSO-D$_2$O, 400 MHz): δ 7.82 (d, 1H), 7.59 (t, 1H), 7.44 (t, 1H), 7.06 (d, 1H), 6.75 (s, 1H), 5.36 (d, 1H), 5.31 (d, 1H), 3.76 (br s, 1H,), 3.32 (s, 3H), 3.35-3.25 (m, 1H), 3.20-3.10 (m, 1H), 3.00-2.85 (m, 2H), 2.40 (s, 3H), 2.28-2.08 (m, 1H), 1.87-1.73 (m, 1H).

Example 22

The preparation of (R)-2-[[(7-(3-aminopiperidin-1-yl)-5-chloro-3-methyl-2-oxo-2,3-dihydro-1H-imidazo[4,5-b]pyridin-1-yl]methyl]benzonitrile (Compound 22) trifluoroacetate

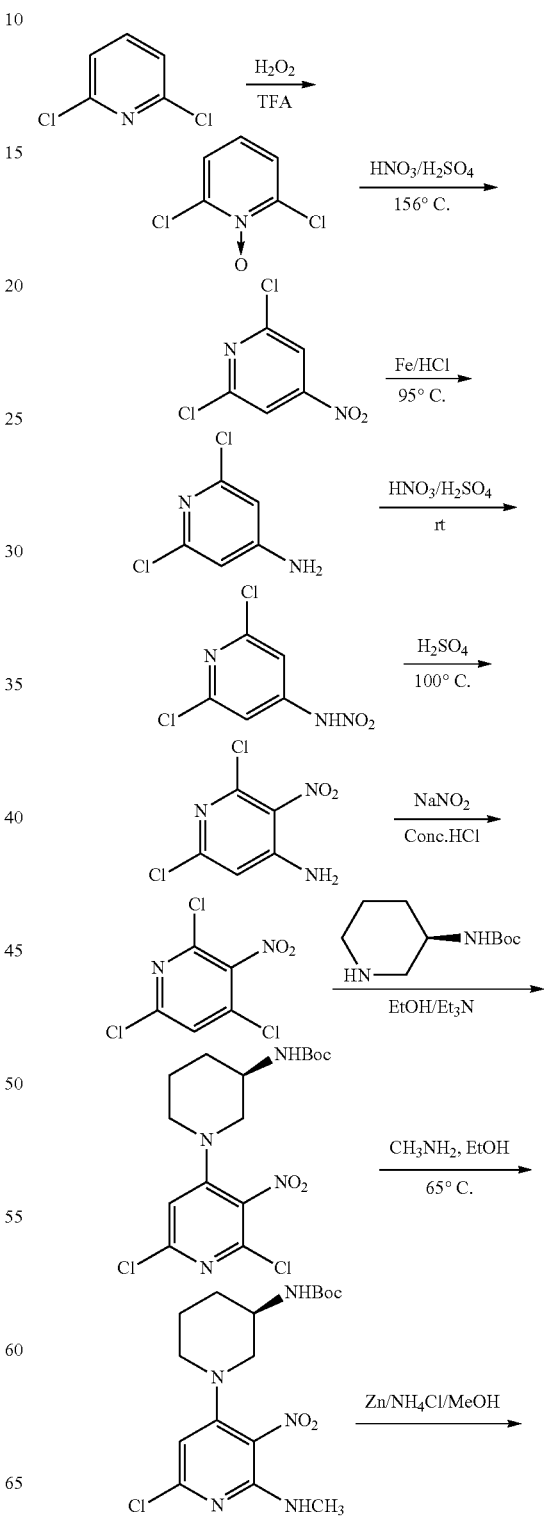

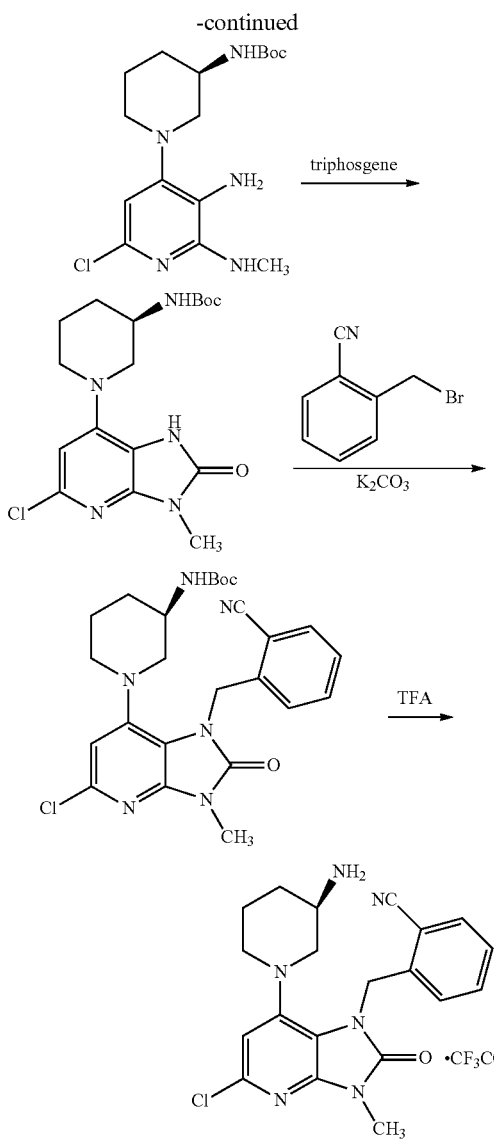

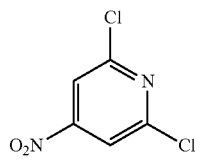 [SMILES: O=[N+]([O-])c1cc(Cl)nc(Cl)c1]

(1) 2,6-dichloropyridine-N-oxide

After the reaction solution of trifluoroacetic acid (485 mL, 6.3 mol), 2,6-dichloropyridine (48 g, 324 mmol) and 35% hydrogen peroxide (85.0 mL, 971 mmol) was stirred for 6.5 h under the condition of reflux, it was cooled to room temperature. The reaction solution was poured into beaker contained 2.4 L water, and cooled overnight at 0° C. The solid (unreacted 2,6-dichloropyridine) was removed through a suction filtration. The filtrate was concentrated, to which 500 mL chloroform was added, and potassium carbonate was added until no gas was produced. It was filtrated. The filtrate was concentrated under vacuum to afford 46.6 g light yellow solid, 87.6%.

(2) 2,6-dichloro-4-nitropyridine

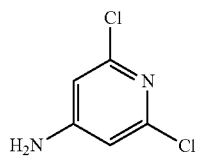

To a solution of 95% concentrated nitric acid (21 mL) and 98% concentrated sulfuric acid (50 mL) was added 2,6-dichloropyridine-N-oxide (12.8 g, 78 mmol). After the reaction was performed at 148° C. by stirring for 1 h, it was continued when the temperature was increased to 156° C. until no nitrogen dioxide was released. The reaction solution was cooled to room temperature, poured into 150 g ice water, and adjusted to pH=6 with ammonia water to precipitate a solid product. It was subjected to suction filtration. The resultant crude product was recrystallized with petroleum ether to afford 10 g yellow solid with a yield of 66.4%.

(3) 2,6-dichloropyridine-4-amine

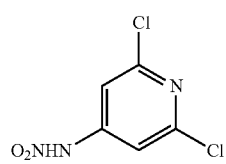

To a solution of 2,6-dichloro-4-nitropyridine (14.82 g, 76.79 mmol) in 350 mL ethanol were sequentially added iron powder (19.91 g, 356.58 mmol), water (65.8 mL, 3.6 mol) and concentrated hydrochloric acid (14.1 mL, 464.1 mmol). After the reaction was performed by stirring for 16 h at 95° C., the reaction solution was cooled to room temperature, adjusted to neutral pH, and subjected to suction filtration. After the filtrate was concentrated, it was extracted with ethyl acetate. The organic phase was combined, dried with anhydrous $MgSO_4$, and subjected to rotary evaporation to afford 11.9 g titled product with a yield of 95.1%.

(4) N-(2,6-dichloropyridin-4-yl)nitramide

To 11 mL concentrated sulfuric acid was added 2,6-dichloropyridin-4-amine (2.18 g, 13.4 mmol) in an ice bath. After it was cooled to 0° C., 4.4 mL 90% nitric acid was added dropwise. After the reaction was performed by stirring for 1 h at room temperature, the reaction solution was poured into ice water to precipitate a solid product, and subjected to suction filtration. The resultant solid was washed with water and dried to afford 2.28 g titled product with a yield of 81.8%.

(5) 2,6-dichloro-3-nitropyridine-4-amine

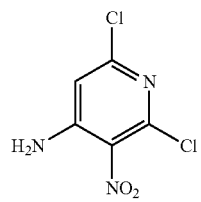 [SMILES: Nc1cc(Cl)nc(Cl)c1[N+](=O)[O-]]

N-(2,6-dichloropyridin-4-yl)nitramide (2.27 g, 10.9 mmol) was added to 18 mL concentrated sulfuric acid, reacted for 20 min at 100° C., and cooled to room temperature. The reaction solution was poured into ice water, and adjusted to pH=8 with strong aqua to precipitate a white solid. The reaction system was left below 10° C. overnight, and subjected to suction filtration. The resultant residue was washed with water and dried to afford 2.27 g white solid with a yield of 100%.

(6) 2,4,6-trichloro-3-nitropyridine

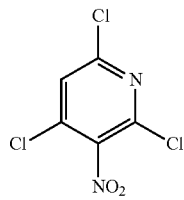 [SMILES: O=[N+]([O-])c1c(Cl)cc(Cl)nc1Cl]

2,6-dichloro-3-nitropyridine-4-amine (2.27 g, 10.9 mmol) was added to 48 mL concentrated hydrochloric acid, and cooled to 0-5° C. To the solution was added sodium nitrite (2.26 g, 32.7 mmol) in batches. After the addition of sodium nitrite, the reaction solution was stirred for 1 h at 0-5° C., and then stirred for 2 h at 25° C., adjusted to pH=7 with 40% sodium hydroxide solution, and extracted with ethyl ether. After the organic phase was dried (Na$_2$SO$_4$) and concentrated, it was subjected to column chromatography eluted with petroleum ether to afford 2 g white solid with a yield of 80.7%.

(7) (R)-1-(2,6-dichloro-3-nitropyridin-4-yl)piperidine-3-tert-butyl carbamate

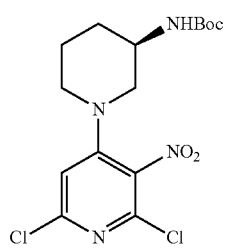 [SMILES: CC(C)(C)OC(=O)N[C@@H]1CCCN(c2cc(Cl)nc(Cl)c2[N+](=O)[O-])C1]

To 30 mL, solution of 2,4,6-trichloro-3-nitropyridine (1.14 g, 5.0 mmol) in ethanol was added triethylamine (1.4 mL, 10 mmol) at −10° C., and stirred in an ice bath. After 15 mL solution of (R)-tert-butylpiperidin-3-yl-carbamate (1 g, 5.0 mmol) in ethanol was slowly added dropwise with a constant pressure funnel, the reaction solution was stirred for 1 h at −10° C., and concentrated. The resultant crude product was subjected to silica gel column chromatography (ethyl acetate:petroleum ether=1:2) to afford 0.78 g titled product with a yield of 39.9%.

(8) (R)-1-[6-chloro-2-(methylamino)-3-nitropyridin-4-yl]piperidine-3-tert-butyl carbamate

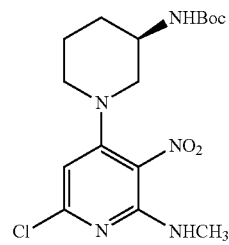 [SMILES: CNc1nc(Cl)cc(N2CCC[C@@H](NC(=O)OC(C)(C)C)C2)c1[N+](=O)[O-]]

To a 100 mL round bottom flask were sequentially added (R)-1-(2,6-dichloro-3-nitropyridin-4-yl)piperidine-3-tert-butyl carbamate (2.7 g, 6.9 mmol), 30 mL ethanol, and 4 mL 27% solution of methylamine in alcohol. It was stirred for 24 h at room temperature, and concentrated. The resultant crude product was subjected to silica gel column chromatography (ethyl acetate:petroleum ether=1:2) to afford 1.62 g yellow solid with a yield of 60.9%.

(9) (R)-1-(3-amino-6-chloro-2-(methylamino)pyridin-4-yl)piperidine-3-tert-butyl carbamate

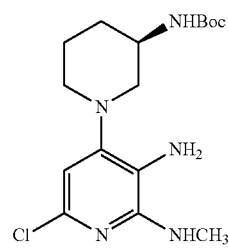

In a dry reaction bottle, (R)-1-[6-chloro-2-(methylamino)-3-nitropyridin-4-yl]piperidine-3-tert-butyl carbamate (217 mg, 0.563 mmol) was added, and dissolved in 10 mL tetrahydrofuran and 10 mL methanol. Zinc dust (0.366 g, 5.60 mmol) and ammonium chloride (0.302 g, 5.70 mmol) were added at room temperature. It was stirred for 16 h at room temperature and filtrated. The reaction solution was concentrated to afford 193 mg titled product with a yield of 96.1%.

(10) (R)-1-(5-chloro-3-methyl-2-oxo-2,3-dihydro-1H-imidazo[4,5-b]pyridin-7-yl)piperidine-3-tert-butyl carbamate

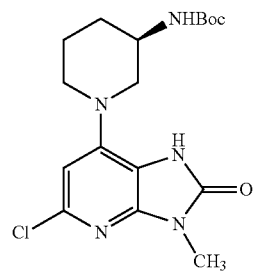 [SMILES: Cn1c(=O)[nH]c2c(N3CCC[C@@H](NC(=O)OC(C)(C)C)C3)cc(Cl)nc21]

The specific operation referred to the step (4) described in Example 1 for details. (R)-1-[3-amino-6-chloro-2-(methylamino)pyridin-4-yl]piperidine-3-tert-butyl carbamate (150 mg, 0.422 mmol) was charged to afford 152 mg titled product with a yield of 94.4%.

(11) (R)-1-[5-chloro-1-(2-cyanobenzyl)-3-methyl-2-oxo-2,3-dihydro-1H-imidazo[4,5-b]pyridin-7-yl]piperidine-3-tert-butyl carbamate

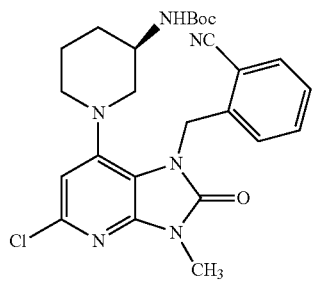

The specific operation referred to the step (5) described in Example 1 for details. (R)-1-(5-chloro-3-methyl-2-oxo-2,3-dihydro-1H-imidazo[4,5-b]pyridin-7-yl)piperidine-3-tert-butyl carbamate (152 mg, 0.398 mmol) was charged to afford 110 mg white powder with a yield of 55.6%.

(12) (R)-2-[[7-(3-aminopiperidin-1-yl)-5-chloro-3-methyl-2-oxo-2,3-dihydro-1H-imidazo[4,5-b]pyridin-1-yl]methyl]benzonitrile trifluoroacetate

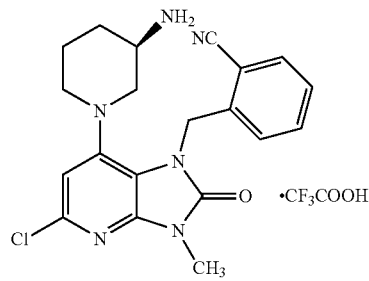 [SMILES: Cn1c(=O)n(Cc2ccccc2C#N)c2c(N3CCC[C@@H](N)C3)cc(Cl)nc21 ; "·CF3COOH"]

The specific operation referred to the step (6) described in Example 1 for details. (R)-1-[5-chloro-1-(2-cyanobenzyl)-3-methyl-2-oxo-2,3-dihydro-1H-imidazo[4,5-b]pyridin-7-yl]piperidine-3-tert-butyl carbamate (110 mg, 0.22 mmol) was charged to afford 74 mg titled product with a yield of 65.8%.

Molecular formula: $C_{20}H_{21}ClN_6O$ Molecular weight: 396.87 Mass spectrum (M+H): m/z: 397.2

$^1$H-NMR (D$_2$O, 400 MHz): δ 7.72 (d, 1H), 7.50 (t, 1H), 7.37 (t, 1H), 7.03 (d, 1H), 7.00 (s, 1H), 5.47 (d, 1H), 5.36 (d, 1H), 3.33 (s, 3H), 3.13 (d, 1H), 3.00 (br s, 1H), 2.87 (d, 1H), 2.73 (t, 1H), 2.68-2.47 (br s, 1H), 2.05-1.90 (m, 1H), 1.70-1.53 (m, 1H), 1.45-1.26 (m, 2H).

Example 23

The preparation of (R)-2-[[7-(3-aminopiperidin-1-yl)-5-(dimethylamino)-3-methyl-2-oxo-2,3-dihydro-1H-imidazo[4,5-b]pyridin-1-yl]methyl]benzonitrile (Compound 23) trifluoroacetate

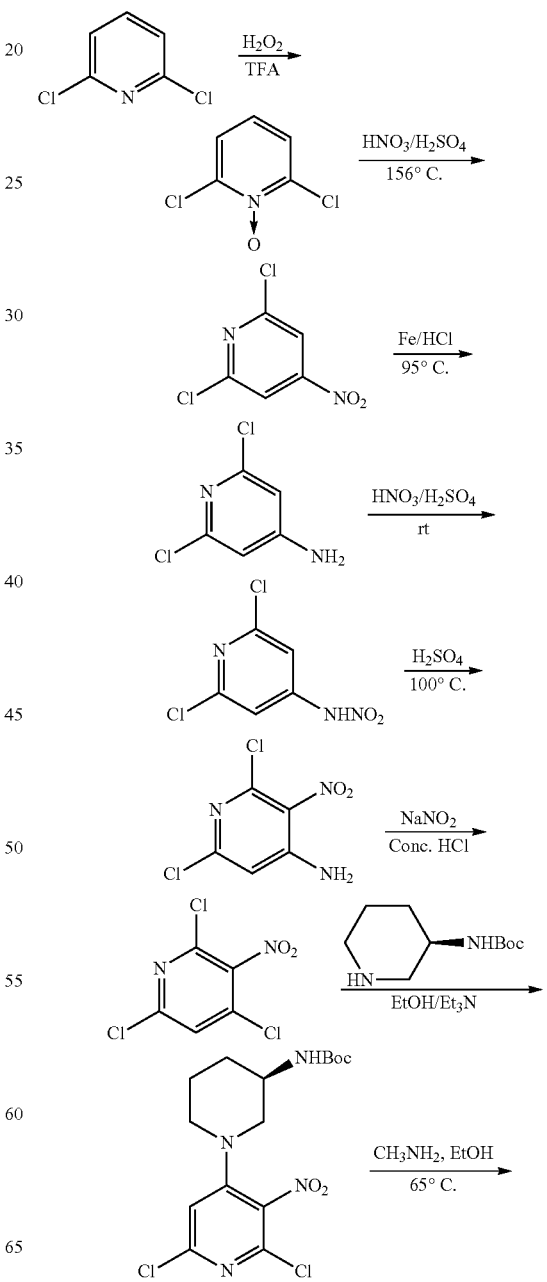

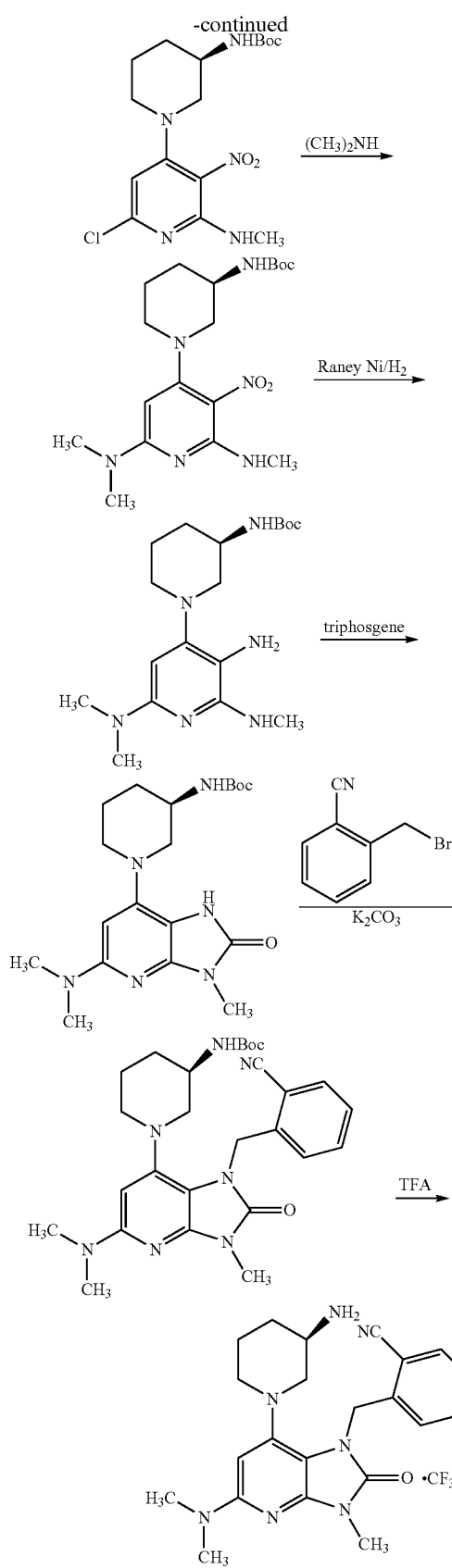

The steps (1)-(8) were same as the steps (1)-(8) described in the preparation example of Compound 22.

(9) (R)-1-[6-(dimethylamino)-2-(methylamino)-3-nitropyridin-4-yl]piperidine-3-tert-butyl carbamate To a 100 mL round bottom flask were sequentially added (R)-1-[6-chloro-2-(methylamino)-3-nitropyridin-4-yl]piperidine-3-tert-butyl carbamate (0.3 g, 0.778 mmol), 10 mL ethanol, and 0.12 mL 33% dimethylamine aqueous solution. It was stirred for 24 h at room temperature, and concentrated. The resultant crude product was subjected to silica gel column chromatography (ethyl acetate:petroleum ether=1:3) to afford 0.196 g yellow solid with a yield of 63.9%.

(10) (R)-1-[3-amino-6-(dimethylamino)-2-(methylamino)pyridin-4-yl]piperidine-3-tert-butyl carbamate In a dry reaction bottle, (R)-1-[6-(dimethylamino)-2-(methylamino)-3-nitropyridin-4-yl]piperidine-3-tert-butyl carbamate (124 mg, 0.314 mmol) was added and dissolved in 10 mL tetrahydrofuran, to which 0.09 g raney nickel was added at room temperature, and hydrogen gas was introduced. It was stirred for 1 h and filtrated. The reaction solution was directly used in the subsequent reaction.

(11) (R)-1-[5-(dimethylamino)-3-methyl-2-oxo-2,3-dihydro-1H-imidazo[4,5-b]pyridin-7-yl]piperidine-3-tert-butyl carbamate In a dry reaction bottle, triphosgene (100 mg, 0.34 mmol), and triethylamine (0.19 mL, 1.38 mmol) were dissolved in 20 mL tetrahydrofuran. The reaction solution obtained in the step described above (i.e., a solution of (R)-1-[3-amino-6-(dimethylamino)-2-(methylamino)pyridin-4-yl]piperidine-3-tert-butyl carbamate in tetrahydrofuran) was slowly added dropwise with a constant pressure funnel at −10° C. It was stirred for 0.5 h, adjusted to pH=8 with saturated sodium carbonate solution, and then extracted with ethyl acetate (100 mL×3). The organic phase was dried with anhydrous sodium sulfate, and concentrated to afford 36 mg titled product (the yield of two-step was 29.1%).

(12) (R)-1-[1-(2-cyanobenzyl)-5-(dimethylamino)-3-methyl-2-oxo-2,3-dihydro-1H-imidazo[4,5-b]pyridin-7-yl]piperidine-3-tert-butyl carbamate

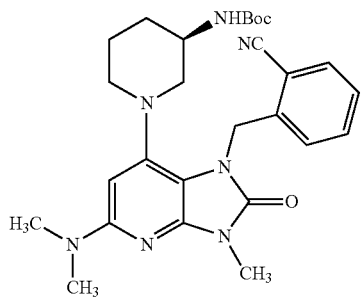 [SMILES: CN(C)c1cc(N2CCC[C@@H](NC(=O)OC(C)(C)C)C2)c2c(n1)n(C)c(=O)n2Cc1ccccc1C#N]

To a dry reaction bottle were sequentially added (R)-1-[5-(dimethylamino)-3-methyl-2-oxo-2,3-dihydro-1H-imidazo[4,5-b]pyridin-7-yl]piperidine-3-tert-butyl carbamate (36 mg, 0.0922 mmol), 2 mL DMF and potassium carbonate K$_2$CO$_3$ (25 mg, 0.184 mmol). A solution of 2-(bromomethyl)benzonitrile (19.9 mg, 0.101 mmol) in 2 mL DMF was added dropwise at −10° C., and stirred for 3 h at room temperature. The reaction solution was added dropwise to water to precipitate a solid, dried, and purified through a silica gel column chromatography (petroleum ether:ethyl acetate=1:3) to afford 25 mg yellow powder with a yield of 54.1%.

(13) (R)-2-[[7-(3-aminopiperidin-1-yl)-5-(dimethylamino)-3-methyl-2-oxo-2,3-dihydro-1H-imidazo[4,5-b]pyridin-1-yl]methyl]benzonitrile trifluoroacetate

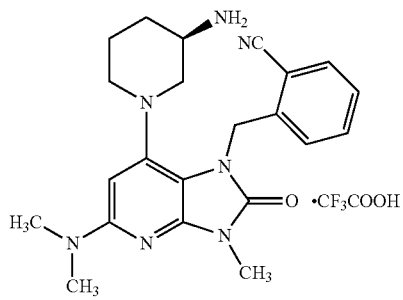 [SMILES: CN(C)c1cc(N2CCC[C@@H](N)C2)c2c(n1)n(C)c(=O)n2Cc1ccccc1C#N ; "·CF3COOH"]

The operation referred to the step (6) described in Example 1 for details. (R)-1-[1-(2-cyanobenzyl)-5-(dimethylamino)-3-methyl-2-oxo-2,3-dihydro-1H-imidazo[4,5-b]pyridin-7-yl]piperidine-3-tert-butyl carbamate (100 mg, 0.198 mmol) was charged to afford 60 mg titled product with a yield of 58.4%.

Molecular formula: C$_{22}$H$_{27}$N$_7$O Molecular weight: 405.23
Mass spectrum (M+H): m/z: 406.2

$^1$H-NMR (D$_2$O, 400 MHz): δ 7.69 (d, 1H), 7.47 (t, 1H), 7.33 (t, 1H), 6.95 (d, 1H), 6.06 (s, 1H), 5.38 (d, 1H), 5.27 (d, 1H), 3.30 (s, 3H), 3.09 (d, 1H), 2.89 (s, 6H), 2.82 (m, 1H), 2.79 (d, 1H), 2.72 (m, 1H), 2.49 (m, 1H), 1.94 (m, 1H), 1.59 (m, 1H), 1.34 (m, 2H).

Example 24

The preparation of 2-[[3-methyl-2-oxo-7-(piperazin-1-yl)-2,3-dihydro-1H-imidazo[4,5-b]pyridin-1-yl]methyl]benzonitrile (Compound 24) trifluoroacetate

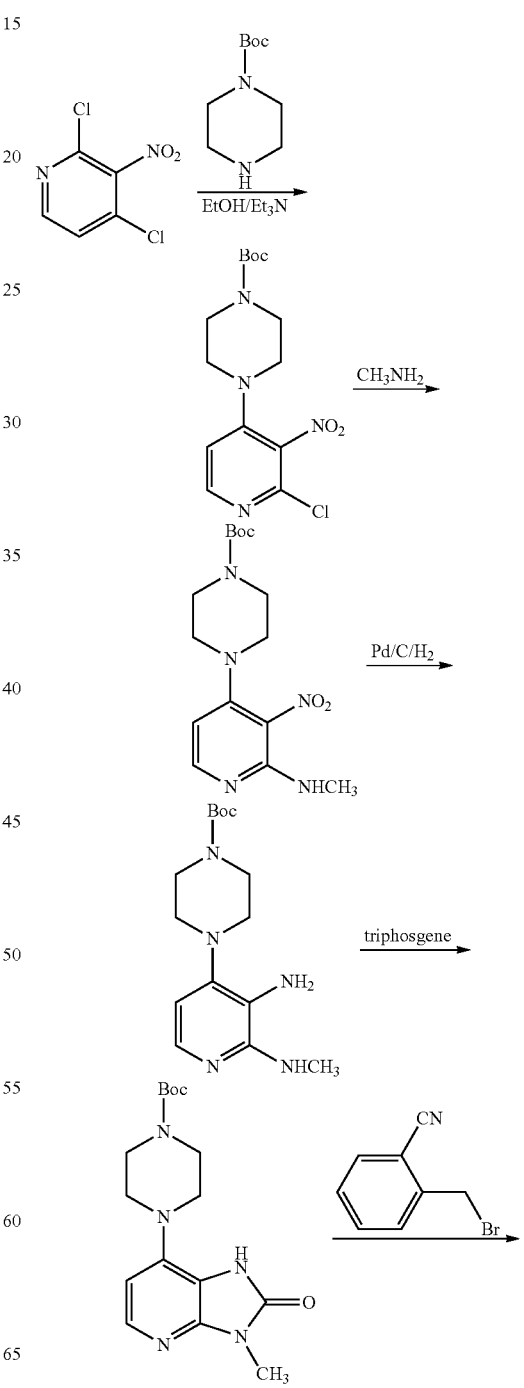

107

-continued

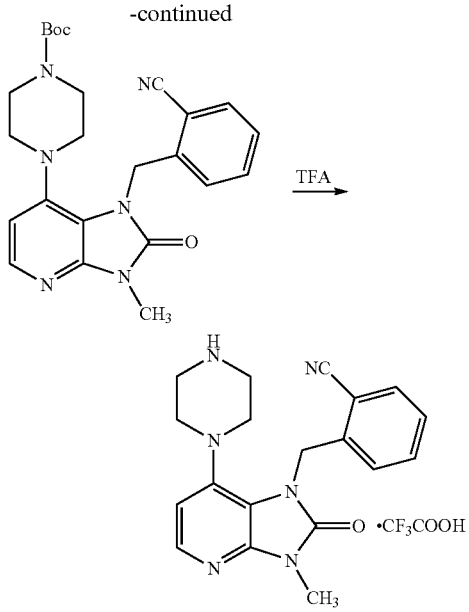

(1) 4-(2-chloro-3-nitropyridin-4-yl)piperazine-1-carboxylic acid tert-butyl ester

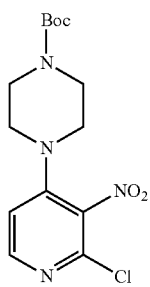 [SMILES: CC(C)(C)OC(=O)N1CCN(c2ccnc(Cl)c2[N+](=O)[O-])CC1]

The specific operation referred to the step (1) described in Example 1 for details. 2,4-dichloro-3-nitropyridine (772 mg, 4.0 mmol), and piperazine-1-carboxylic acid tert-butyl ester (744 mg, 4.0 mmol) were charged to afford 1.299 g crude product with a yield of 94.7%, which was directly used in the subsequent reaction.

(2) 4-[2-(methylamino)-3-nitropyridin-4-yl]piperazine-1-carboxylic acid tert-butyl ester

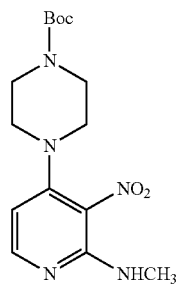 [SMILES: CNc1nccc(N2CCN(C(=O)OC(C)(C)C)CC2)c1[N+](=O)[O-]]

The specific operation referred to the step (2) described in Example 1 for details. 1.299 g 4-(2-chloro-3-nitropyridin-4-yl)piperazine-1-carboxylic acid tert-butyl ester (3.79 mmol) was charged to afford 1.102 g titled product with a yield of 86.2%.

108

(3) 4-[3-amino-2-(methylamino)pyridin-4-yl]piperazine-1-carboxylic acid tert-butyl ester

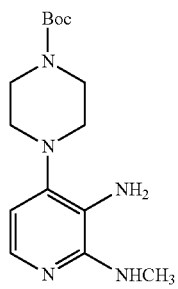 [SMILES: CNc1nccc(N2CCN(C(=O)OC(C)(C)C)CC2)c1N]

The specific operation referred to the step (3) described in Example 1 for details. 1.102 g 4-[2-(methylamino)-3-nitropyridin-4-yl]piperazine-1-carboxylic acid tert-butyl ester (3.266 mmol) was charged to afford 0.556 g titled product with a yield of 55.4%.

(4) 4-(3-methyl-2-oxo-2,3-dihydro-1H-imidazo[4,5-b]pyridin-1-yl)piperazine-1-carboxylic acid tert-butyl ester

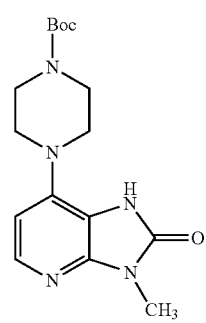 [SMILES: Cn1c(=O)[nH]c2c(N3CCN(C(=O)OC(C)(C)C)CC3)ccnc21]

The specific operation referred to the step (4) described in Example 1 for details. 0.556 g 4-[3-amino-2-(methylamino)pyridin-4-yl]piperazine-1-carboxylic acid tert-butyl ester (1.81 mmol) was charged to afford 0.60 g titled product with a yield of 99.4%.

(5) 4-[1-(2-cyanobenzyl)-3-methyl-2-oxo-2,3-dihydro-1H-imidazo[4,5-b]pyridin-1-yl]piperazine-1-carboxylic acid tert-butyl ester

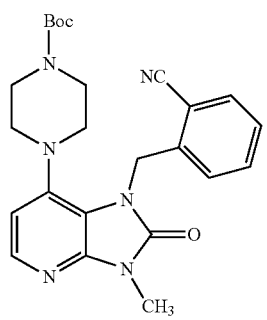 [SMILES: Cn1c(=O)n(Cc2ccccc2C#N)c2c(N3CCN(C(=O)OC(C)(C)C)CC3)ccnc21]

The specific operation referred to the step (5) described in Example 1 for details. 0.60 g 4-(3-methyl-2-oxo-2,3-dihydro-1H-imidazo[4,5-b]pyridin-1-yl)piperazine-1-carboxylic acid tert-butyl ester (1.80 mmol) was charged to afford 0.514 g titled product with a yield of 63.7%.

(6)2-[[3-methyl-2-oxo-7-(piperazin-1-yl)-2,3-dihydro-1H-imidazo[4,5-b]pyridin-1-yl]methyl]benzonitrile trifluoroacetate

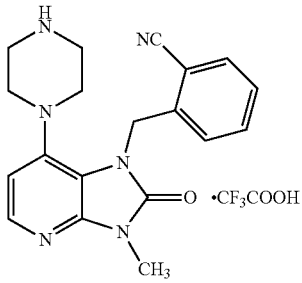 [SMILES: Cn1c(=O)n(Cc2ccccc2C#N)c2c(N3CCNCC3)ccnc21 ; "·CF3COOH"]

The specific operation referred to the step (6) described in Example 1 for details. 0.51 g 4-[1-(2-cyanobenzyl)-3-methyl-2-oxo-2,3-dihydro-1H-imidazo[4,5-b]pyridin-1-yl]piperazine-1-carboxylic acid tert-butyl ester (1.14 mmol) was charged to afford 0.30 g titled product with a yield of 75.5%.

Molecular formula: $C_{19}H_{20}N_6O$ Molecular weight: 348.4
Mass spectrum (M+H): m/z: 349.2
$^1$H NMR (600 MHz, d6-DMSO+D$_2$O): δ 8.05 (d, 1H), 7.88 (d, 1H), 7.62 (t, 1H), 7.49 (t, 1H), 7.08 (d, 1H), 7.03 (d, 1H), 5.43 (s, 2H), 3.39 (s, 3H), 3.00 (s, 8H).

Example 25

The preparation of (R)-2-[[7-(3-aminopiperidin-1-yl)-5-ethyl-3-methyl-2-oxo-2,3-dihydro-1H-imidazo[4,5-b]pyridin-1-yl]methyl]benzonitrile (Compound 25) trifluoroacetate

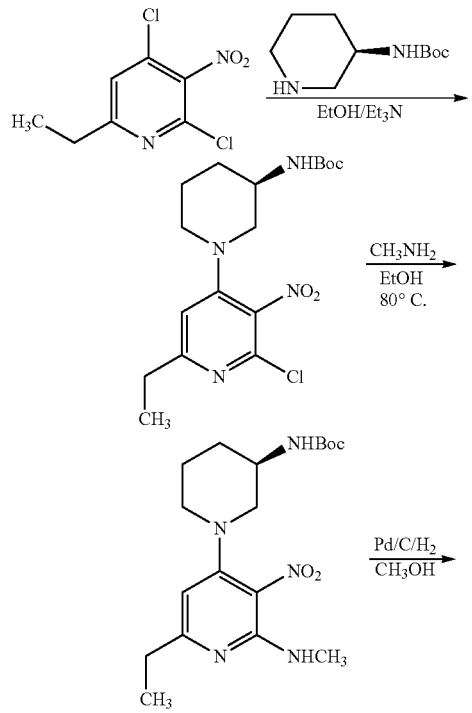

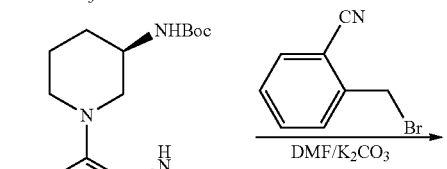

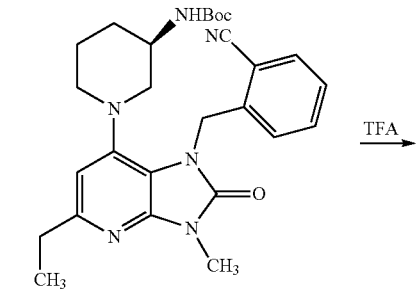

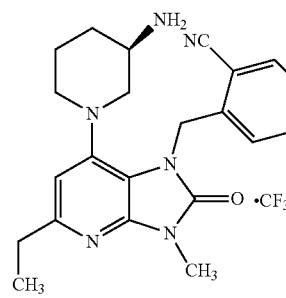

(1) (R)-1-(2-chloro-6-ethyl-3-nitropyridin-4-yl)piperidin-3-yl tert-butyl carbamate

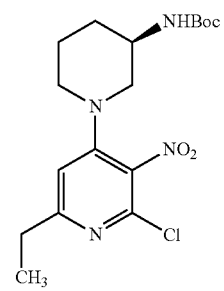

In a dry reaction bottle, 3.74 g (16.92 mmol) 2,4-dichloro-6-ethyl-3-nitropyridine and 4.74 mL triethylamine were added sequentially to 83 mL ethanol. A solution of 4.04 g R-tert-butylpiperidin-3-yl-carbamate (20.172 mmol) in 55 mL ethanol was added dropwise to the above reaction system at room temperature, and stirred for 21 h at room temperature. The reaction solution was concentrated under a reduced pressure, and purified through a column chromatography (Ethyl acetate:Petroleum Ether=1:10) to afford 3.598 g yellow solid with a yield of 55.3%.

The steps (2)-(5) were same as the steps (2)-(5) described in the preparation example of Compound 1.

(6) (R)-2-[[7-(3-aminopiperidin-1-yl)-5-ethyl-3-methyl-2-oxo-2,3-dihydro-1H-imidazo[4,5-b]pyridin-1-yl]methyl]benzonitrile trifluoroacetate

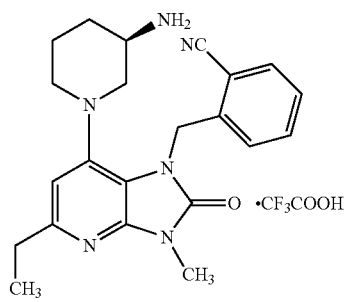 [SMILES: CCc1cc(N2CCC[C@@H](N)C2)c2c(n1)n(C)c(=O)n2Cc1ccccc1C#N ; "·CF3COOH"]

The specific operation referred to the step (6) described in Example 1 for details. 0.69 g (R)-1-[1-(2-cyanophenyl)-5-ethyl-3-methyl-2-oxo-2,3-dihydro-1H-imidazo[4,5-b]pyridin-7-yl]piperidin-3-yl tert-butyl carbamate (1.406 mmol) was charged to afford 0.458 g trifluoroacetate of the titled product with a yield of 64.5%.

Molecular formula: $C_{22}H_{26}N_6O$ Molecular weight: 390.48
Mass spectrum (M+H): m/z: 391.2
$^1$H-NMR (D$_2$O, 400 MHz): δ 7.68 (d, 1H), 7.47 (t, 1H), 7.34 (t, 1H), 7.00 (d, 1H), 6.85 (s, 1H), 5.43 (d, 1H), 5.32 (d, 1H), 3.36 (s, 3H), 3.19-3.17 (m, 1H), 3.01 (br s, 1H), 2.89-2.71 (m, 2H), 2.68 (q, 2H), 2.64-2.55 (m, 1H), 1.98 (br s, 1H), 1.63-1.60 (m, 1H), 1.41-1.37 (m, 2H), 1.14 (t, 3H).

Example 26

The preparation of (R)-2-[[7-(3-aminopiperidin-1-yl)-3-ethyl-5-methyl-2-oxo-2,3-dihydro-1H-imidazo[4,5-b]pyridin-1-yl]methyl]benzonitrile (Compound 26) trifluoroacetate

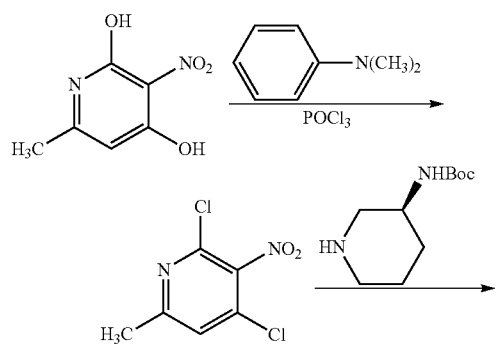

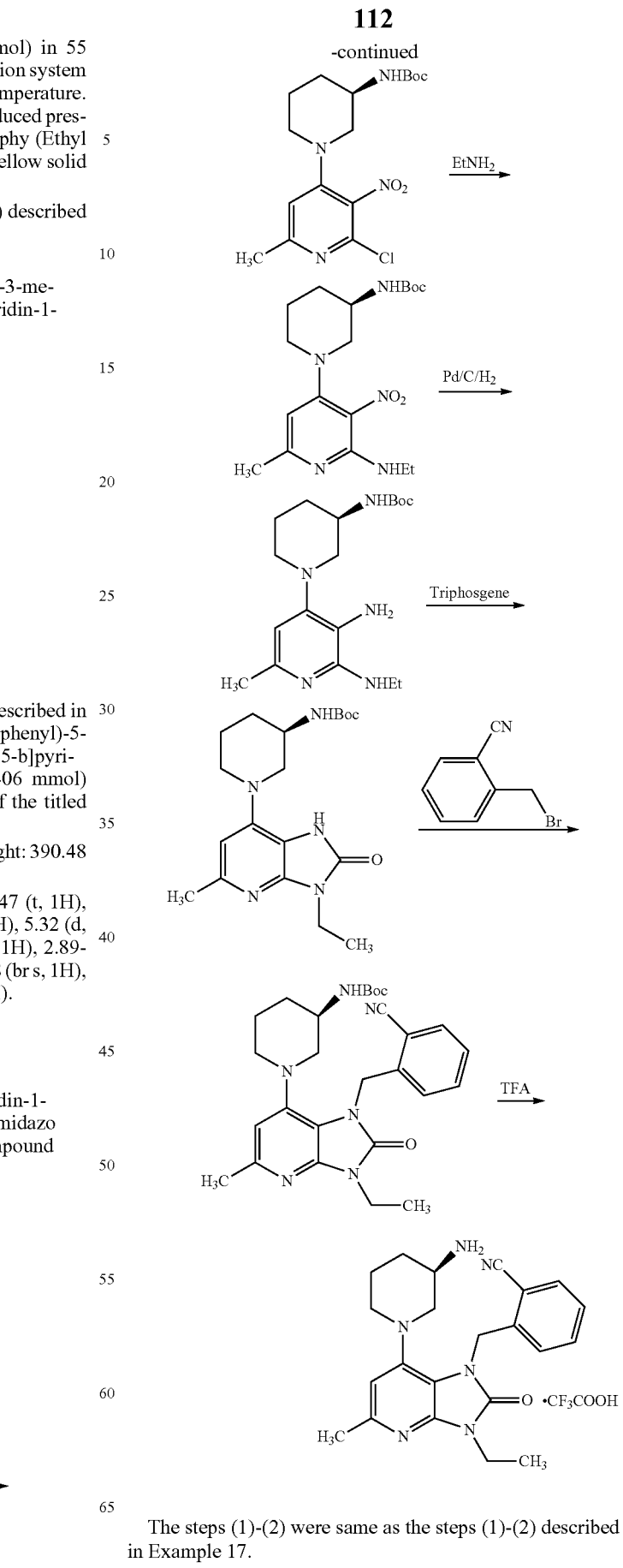

The steps (1)-(2) were same as the steps (1)-(2) described in Example 17.

(3) (R)-1-(2-ethylamino-6-methyl-3-nitro-pyridin-4-yl)piperidin-3-yl tert-butyl carbamate

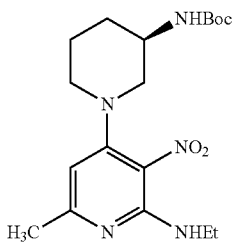

In a single-neck flask was added 10 mL ethanol, and 1.9 g (R)-1-(2-chloro-3-nitro-6-methylpyridin-4-yl)piperidin-3-yl tert-butyl carbamate (5.1 mmol) was added 0.66 g (10.2 mmol) ethylamine aqueous solution at a concentration of 70% at a low temperature. When the temperature was increased to 60° C., the reaction was continued for 5 h. The reaction system was spinned to dryness and purified through column to afford 1.2 g yellow solid with a yield of 62.0%.

(4) (R)-1-(3-amino-2-ethylamino-6-methyl-pyridin-4-yl)piperidin-3-yl tert-butyl carbamate

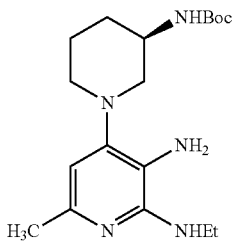

1.2 g (R)-1-(2-ethylamino-6-methyl-3-nitro-pyridin-4-yl)piperidin-3-yl tert-butyl carbamate (3.16 mmol) was dissolved in 40 mL methanol, to which 0.2 g 10% Pd—C was added. The reaction was continued for 3 h at room temperature by introducing hydrogen gas. After the starting materials were reacted completely as monitored by TLC, the reaction system was subjected to suction filtration. After the filtrate was spinned to dryness, 10 mL water was added. It was extracted with (3×10 mL) dichloromethane, washed with water, dried, and spinned to dryness to afford 1.0 g titled product with a yield of 90.5%.

(5) (R)-1-(3-ethyl-5-methyl-2-oxo-2,3-dihydro-1H-imidazo[4,5-b]pyridin-7-yl)piperidin-3-yl tert-butyl carbamate

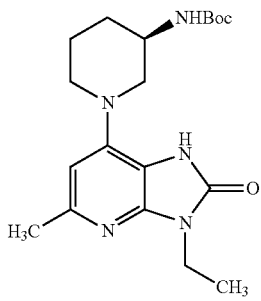 [SMILES: CCn1c(=O)[nH]c2c(N3CCC[C@@H](NC(=O)OC(C)(C)C)C3)cc(C)nc21]

0.936 g triphosgene solid (3.15 mmol) was added to 30 mL THF at −10° C., to which 1.16 g triethylamine (11.46 mmol) was added. A solution of 1.0 g (R)-1-(3-amino-2-ethylamino-6-methyl-pyridin-4-yl)piperidin-3-yl tert-butyl carbamate (2.86 mmol) in 20 mL THF was added dropwise. The reaction was continued for 2 h at a low temperature. And then, the reaction solution was treated by adding saturated NaHCO$_3$ solution, extracted with dichloromethane, dried, and spinned to dryness. A column chromatography was performed to afford 0.3 g titled product with a yield of 27.9%.

(6) (R)-1-[1-(2-cyanobenzyl)-3-ethyl-5-methyl-2-oxo-2,3-dihydro-1H-imidazo[4,5-b]pyridin-7-yl]piperidin-3-yl tert-butyl carbamate

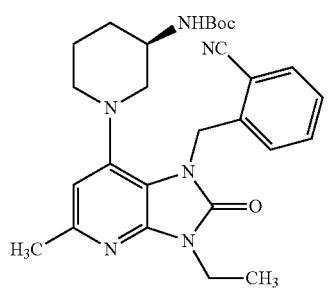

The specific operation referred to the step (5) described in Example 1 for details. 0.3 g (R)-1-(3-ethyl-5-methyl-2-oxo-2,3-dihydro-1H-imidazo[4,5-b]pyridin-7-yl)piperidin-3-yl tert-butyl carbamate (0.80 mmol) was charged to afford 200 mg crude product. It was recrystallized to afford 150 mg pure product with a yield of 38.2%.

(7) (R)-2-[[7-(3-aminopiperidin-1-yl)-3-ethyl-5-methyl-2-oxo-2,3-dihydro-1H-imidazo[4,5-b]pyridin-1-yl]methyl]benzonitrile trifluoroacetate

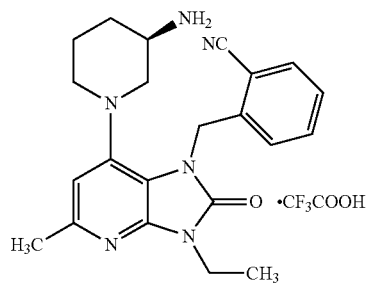 [SMILES: CCn1c(=O)n(Cc2ccccc2C#N)c2c(N3CCC[C@@H](N)C3)cc(C)nc21 ; "·CF3COOH"]

150 mg (R)-1-[1-(2-cyanobenzyl)-3-ethyl-5-methyl-2-oxo-2,3-dihydro-1H-imidazo[4,5-b]pyridin-7-yl]piperidin-3-yl tert-butyl carbamate (0.306 mmol) was dissolved in 2.5 mL dichloromethane at 0° C. 3.2 mL trifluoroacetic acid was added dropwise. After the reaction was continued for 0.5 h at 0° C., it was continued for 0.5 h at room temperature. After the reaction was finished, the reaction system was spinned to dryness, and then evaporated after adding dichloromethane. And then, the reaction system was treated by adding 2 drops of ethanol to slightly dissolve, and added dropwise to 20 mL ethyl ether. The ethyl ether layer was poured off, and the remaining undissolved oil was dissolved by adding dichloromethane, and spinned to dryness to afford 100 mg (R)-2-[[7-(3-aminopiperidin-1-yl)-3-ethyl-5-methyl-2-oxo-2,3-dihydro-1H-imidazo[4,5-b]pyridin-1-yl]methyl]benzonitrile trifluoroacetate as white solid with a yield of 64.8%.

Molecular formula: $C_{22}H_{26}N_6O$ Molecular weight: 390.48
Mass spectrum (M+H): m/z: 391.2

$^1$H-NMR (D$_2$O, 400 MHz): δ 7.70 (d, 1H), 7.50 (t, 1H), 7.36 (t, 1H), 7.05 (d, 1H), 6.86 (s, 1H), 5.44 (d, 1H), 5.34 (d, 1H), 3.92 (q, 2H), 3.28-3.20 (m, 1H), 3.15-3.02 (br s, 1H), 2.97 (d, 1H), 2.82 (t, 1H), 2.70-2.57 (m, 1H), 2.43 (s, 3H), 2.05-1.92 (m, 1H), 1.68-1.52 (br s, 1H), 1.50-1.31 (m, 2H), 1.19 (t, 3H).

Example 27

The preparation of (R)—N-[1-[1-(2-cyanobenzyl)-3,5-dimethyl-2-oxo-2,3-dihydro-1H-imidazo[4,5-b]pyridin-7-yl]piperidin-3-yl]acetamide (Compound 27)

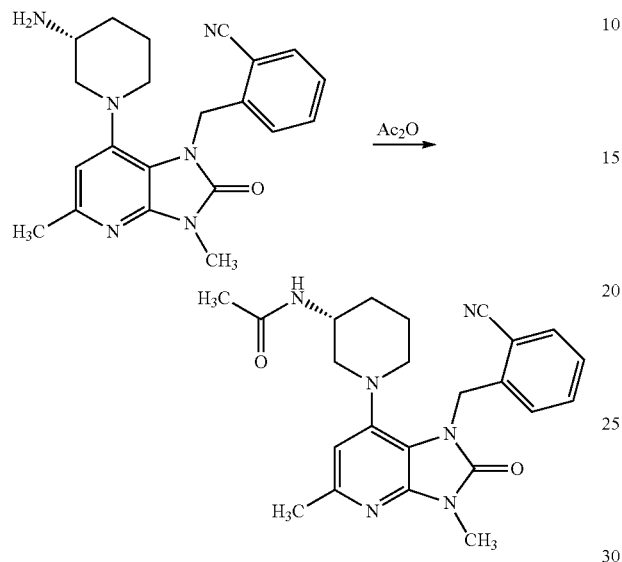

430 mg (R)-2-[[7-(3-aminopiperidin-1-yl)-3,5-dimethyl-2-oxo-2,3-dihydro-1H-imidazo[4,5-b]pyridin-1-yl]methyl]benzonitrile (1.14 mmol) was dissolved in 5 mL dichloromethane at 0° C. 0.35 mL (2.5 mmol) triethylamine and 123 mg (1.2 mmol) acetic anhydride were added dropwise. After the reaction was continued for 1 h at 0° C., ethyl acetate was added until turbidity appeared. It was cooled at −5° C., and a lot of solid was precipitated. 270 mg white powder was obtained after filtration, with a yield of 56.6%.

Molecular formula: $C_{23}H_{26}N_6O_2$ Molecular weight: 418.49 Mass spectrum (M+H): m/z: 419.2

$^1$H-NMR (DMSO, 400 MHz): δ 7.84 (d, 1H), 7.73 (d, 1H), 7.58 (t, 1H), 7.43 (t, 1H), 7.00 (d, 1H), 6.74 (s, 1H), 5.46 (d, 1H), 5.34 (d, 1H), 3.65-3.52 (m, 1H), 3.32 (s, 3H), 3.08 (m, 1H), 2.87 (m, 1H), 2.58-2.42 (m, 2H), 2.50 (s, 3H), 1.76 (m, 1H), 1.72 (s, 3H), 1.59 (m, 1H), 1.40-1.17 (m, 2H).

Example 28

The preparation of (R)-2-[[7-(3-aminopiperidin-1-yl)-5-methyl-2-oxo-2,3-dihydro-1H-imidazo[4,5-b]pyridin-1-yl]methyl]benzonitrile (Compound 28) dihydrochlorate

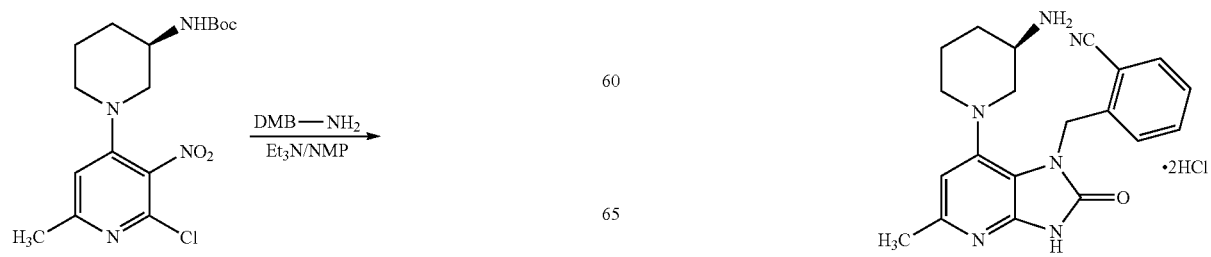

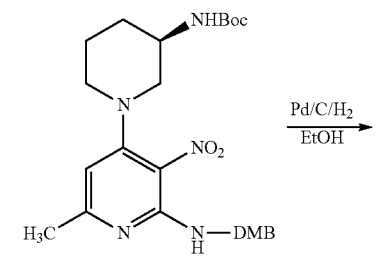

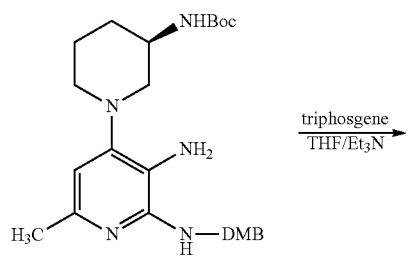

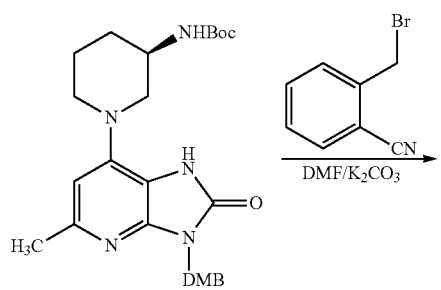

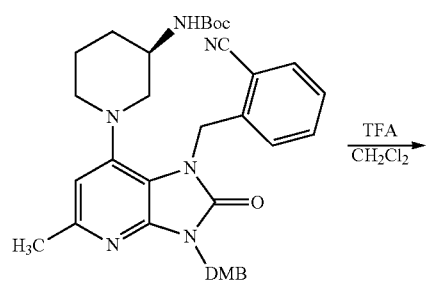

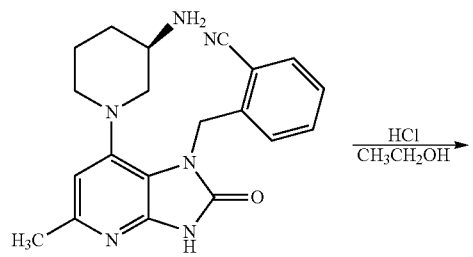

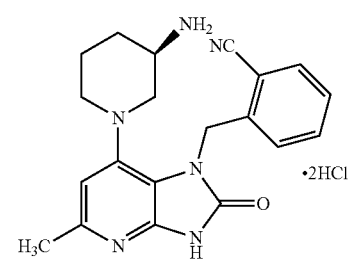 [SMILES: Cc1cc(N2CCC[C@@H](N)C2)c2c(n1)[nH]c(=O)n2Cc1ccccc1C#N]

(1) (R)-1-[2-(2,4-dimethoxybenzyl)amino-6-methyl-3-nitropyridin-4-yl]piperidine-3-carbamic acid tert-butyl ester

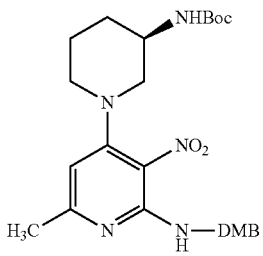

1.85 g (R)-1-(2-chloro-6-methyl-3-nitropyridin-4-yl)piperidine-3-carbamic acid tert-butyl ester (5 mmol) was dissolved in 10 mL N-methylpyrrolidone, to which 1.4 mL triethylamine (10 mmol) was added, and 1.25 g 2,4-dimethoxybenzylamine (7.5 mmoL) was added. The reaction was continued for 24 h at 80° C. The reaction solution was exacted three times with ethyl acetate. The ethyl acetate phase was combined, washed three times with water, dried, and evaporated to dryness. The resultant crude product was purified through a column chromatography (ethyl acetate:petroleum ether=1:8) to afford 1.83 g titled product with a yield of 73.1%.

(2) (R)-1-[2-(2,4-dimethoxybenzyl)amino-6-methyl-3-aminopyridin-4-yl]piperidine-3-carbamic acid tert-butyl ester

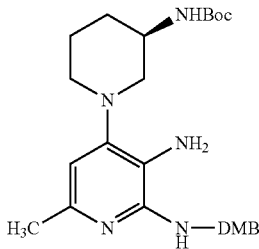

1.83 g (R)-1-[[2-(2,4-dimethoxybenzyl)amino]-6-methyl-3-nitropyridin-4-yl]piperidine-3-carbamic acid tert-butyl ester (3.65 mmol) was dissolved in 10 mL ethanol. 0.14 g (8%) Pd/C was added. The reaction was continued for 16 h at room temperature under an atmosphere of H₂. The reaction solution was subjected to suction filtration to recover palladium carbon. The filtrate was spinned to dryness to afford 1.5 g crude product with a yield of 87.3%.

(3) (R)-1-[3-(2,4-dimethoxybenzyl)-5-methyl-2-oxo-2,3-dihydro-1H-imidazo[4,5-b]pyridin-7-yl]piperidine-3-carbamic acid tert-butyl ester

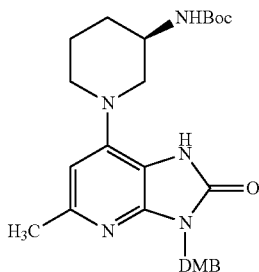

1.42 g triphosgene (4.78 mmol) was dissolved in 10 mL dichloromethane, and cooled to −10° C. 1.77 mL triethylamine (12.72 mmol) was added. A solution of 1.5 g (R)-1-[2-(2,4-dimethoxybenzyl)amino-6-methyl-3-aminopyridin-4-yl]piperidine-3-carbamic acid tert-butyl ester (3.18 mmol) in dichloromethane (20 mL) was slowly added dropwise at −10° C. After they were completely reacted, the reaction solution was adjusted to be basic by adding saturated sodium carbonate solution, and extracted twice with dichloromethane. The combined organic phase was washed with brine, dried with anhydrous sodium sulfate, and evaporated to dryness. The resultant crude product was recrystallized with dichloromethane and ethyl acetate to afford 1.03 g titled product with a yield of 65.2%.

(4) (R)-1-[1-(2 cyanobenzyl)-3-(2,4-dimethoxybenzyl)-5-methyl-2-oxo-2,3-dihydro-1H-imidazo[4,5-b]pyridin-7-yl]piperidine-3-carbamic acid tert-butyl ester

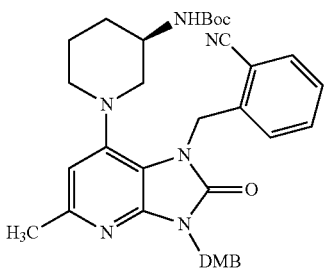

1.03 g (R)-1-[3-(2,4-dimethoxybenzyl)-5-methyl-2-oxo-2,3-dihydro-1H-imidazo[4,5-b]pyridin-7-yl]piperidine-3-carbamic acid tert-butyl ester (2.07 mmol) was dissolved in 5 mL DMF. 0.57 g potassium carbonate (4.14 mmol) was added, and then 0.45 g 2-cyano-benzyl bromide (2.28 mmol) was added. The reaction solution was stirred for 5 h at room temperature, and slowly poured into 100 mL water to precipitate a solid, filtrated, and dried to afford 1.24 g crude product with a yield of 97.9%.

(5) (R)-2-[[7-(3-aminopiperidin-1-yl)-5-methyl-2-oxo-2,3-dihydro-1H-imidazo[4,5-b]pyridin-1-yl]methyl]benzonitrile

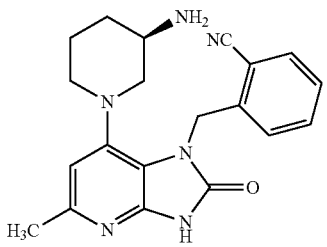 [SMILES: Cc1cc(N2CCC[C@@H](N)C2)c2c(n1)[nH]c(=O)n2Cc1ccccc1C#N]

1.24 g (R)-1-[1-(2-cyanobenzyl)-3-(2,4-dimethoxybenzyl)-5-methyl-2-oxo-2,3-dihydro-1H-imidazo[4,5-b]pyridin-7-yl]piperidine-3-carbamic acid tert-butyl ester (2.02 mmol) was dissolved in 8 mL anisole, to which 1.5 mL trifluoroacetic acid was added, and reacted for 24 h at 90° C. The reaction solution was evaporated to dryness. The residue was dissolved in a small amount of water, and washed with ethyl acetate. The aqueous phase was adjusted to basic with saturated sodium carbonate solution, and extracted with dichloromethane for five times. The dichloromethane phase was combined, dried and evaporated to dryness to afford 0.4 g titled product with a yield of 54.5%.

(6) (R)-2-[[7-(3-aminopiperidin-1-yl)-5-methyl-2-oxo-2,3-dihydro-1H-imidazo[4,5-b]pyridin-1-yl]methyl]benzonitrile dihydrochlorate

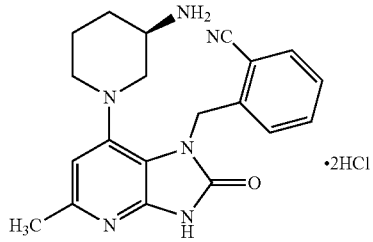 [SMILES: Cc1cc(N2CCC[C@@H](N)C2)c2c(n1)[nH]c(=O)n2Cc1ccccc1C#N ; "·2HCl"]

In a reaction bottle, 0.4 g (R)-2-[[7-(3-aminopiperidin-1-yl)-5-methyl-2-oxo-2,3-dihydro-3H-imidazo[4,5-b]pyridin-1-yl]methyl]benzonitrile (1.1 mmol) was added, and 2 mL ethanol was added. The temperature was increased to 60° C. After dissolved completely, 0.18 mL concentrated hydrochloric acid was slowly added dropwise. After addition, the reaction solution was stirred for 1 h at room temperature, and filtrated to afford 0.18 g final product with a yield of 41.0%.

Molecular formula: $C_{20}H_{22}N_6O$ Molecular weight: 362.43
Mass spectrum (M+H): m/z: 363.2

$^1$H-NMR (D$_2$O, 400 MHz): δ 7.76 (d, 1H), 7.56 (t, 1H), 7.41 (t, 1H), 7.36 (t, 1H), 7.15 (d, 1H), 6.91 (s, 1H), 5.39 (q, 2H), 3.37 (d, 1H), 3.15 (s, 1H), 3.07 (m, 1H), 2.91 (t, 1H), 2.73 (m, 1H), 2.47 (s, 3H), 2.02 (s, 1H), 1.70 (m, 1H), 1.46 (m, 2H).

Example 29

The preparation of (R)-2-[[7-(3-aminopiperidin-1-yl)-3-methyl-5-hydroxymethyl-2-oxo-2,3-dihydro-1H-imidazo[4,5-b]pyridin-1-yl]methyl]benzonitrile (Compound 29) dihydrochlorate

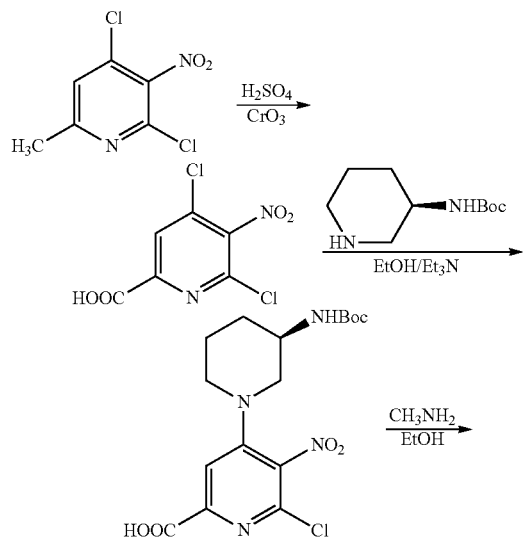

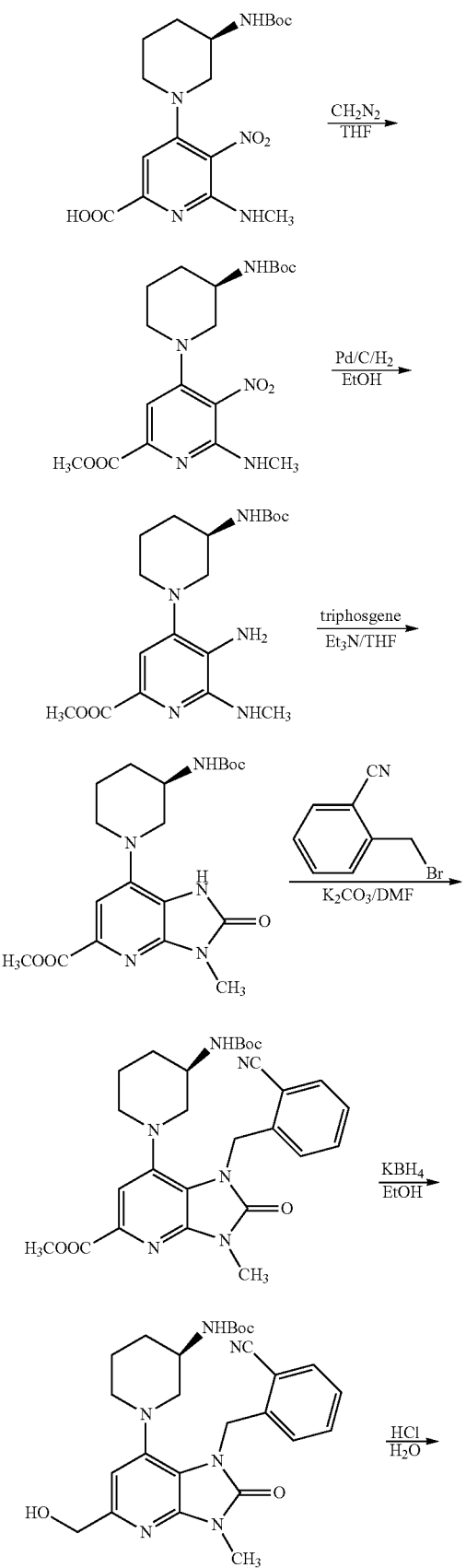

-continued

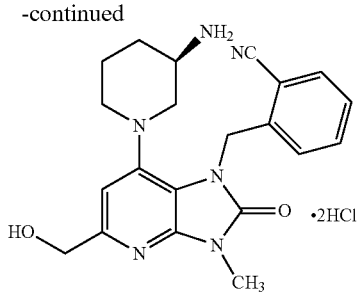
·2HCl (1) 2-formyloxy-4,6-dichloro-5-nitropyridine

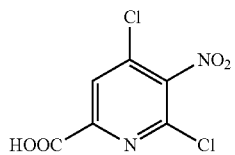 [SMILES: O=C(O)c1cc(Cl)c([N+](=O)[O-])c(Cl)n1]

In a dry reaction bottle, 10.3 g 2,4-dichloro-3-nitro-6-methylpyridine (49.8 mmol) and 50 mL concentrated sulfuric acid were added. 15 g chromium trioxide (150 mmol) was added to the reaction solution in batches. The reaction solution was heated and stirred for 2.5 h in an oil bath of 60° C. The reaction solution was added to ice water to precipitate a white solid, filtrated, and dried under vacuum to afford 10.94 g titled product with a yield of 92.7%.

(2) (R)-1-[2-formyloxy-5-nitro-6 chloropyridin-4-yl]piperidine-3-carbamic acid tert-butyl ester

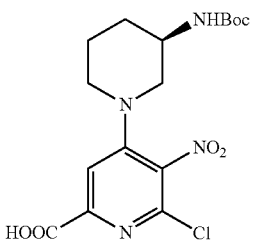 [SMILES: CC(C)(C)OC(=O)N[C@@H]1CCCN(c2cc(C(=O)O)nc(Cl)c2[N+](=O)[O-])C1]

In a dry reaction bottle, 8.4 g (R)-3-Boc-aminopiperidine (42.2 mmol) was dissolved in 30 mL ethanol, added dropwise to a mixture of 50 mL ethanol and 10 g 2-formyloxy-4,6-dichloro-5-nitropyridine (42.2 mmol) at room temperature, and stirred for 2 days at room temperature. The reaction solution was dried under a reduced pressure to afford 16 g crude product as yellow solid, which was directly used in the subsequent reaction.

(3) (R)-1-[2-formyloxy-5-nitro-6-methylaminopyridin-4-yl]piperidine-3-carbamic acid tert-butyl ester

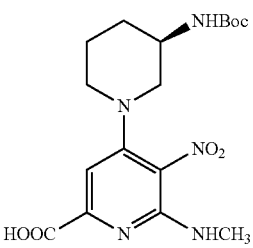 [SMILES: CNc1nc(C(=O)O)cc(N2CCC[C@@H](NC(=O)OC(C)(C)C)C2)c1[N+](=O)[O-]]

In a dry reaction bottle, 16 g (R)-1-[2-formyloxy-5-nitro-6-chloropyridin-4-yl]piperidine-3-carbamic acid tert-butyl ester (40 mmol) was added and dissolved in 50 mL ethanol. 31 g 40% methylamine aqueous solution (400 mmol) was added. The stirring was continued for 2 days at 60° C. The reaction solution was extracted with dichloromethane, dried, and evaporated to dryness to afford a crude product as yellow solid, which was purified through a column chromatography (ethyl acetate:petroleum ether=1:1) to afford 12 g titled product with a yield of 75.9%.

(4) (R)-1-[2-methoxycarbonyl-5-nitro-6-methylaminopyridin-4-yl]piperidine-3-carbamic acid tert-butyl ester

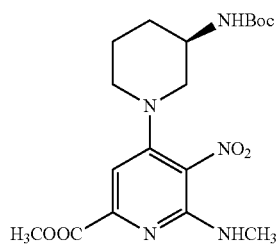

In a dry reaction bottle, 128 mL 50% potassium hydroxide solution was added dropwise to a mixture of 15.93 g nitrosomethylurea and 300 mL ethyl ether at −20° C. The resultant solution was added dropwise to a mixture of 11.85 g (R)-1-[2-formyloxy-5-nitro-6-methylaminopyridin-4-yl]piperidine-3-carbamic acid tert-butyl ester (30 mmol) and 240 mL tetrahydrofuran at the same temperature. After addition, the reaction was stopped. Glacial acetic acid was added, and then water and ethyl acetate were added. The reaction solution was extracted with ethyl acetate. The organic phase was combined and washed with saturated brine. The organic layer was dried with anhydrous sodium sulfate, and purified through a column chromatography (Ethyl acetate:Petroleum Ether=1:8). After column chromatography, the solid was recrystallized with ethyl acetate and n-hexane. After the mother liquor was concentrated, 6.6 g yellow solid was obtained, with a yield of 53.8%.

(5) (R)-1-[2-methoxycarbonyl-5-amino-6-methylaminopyridin-4-yl]piperidine-3-carbamic acid tert-butyl ester

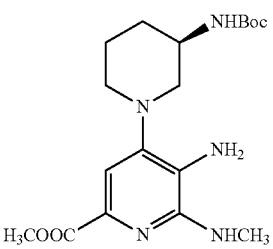

In a dry reaction bottle, 6.54 g (R)-1-[2-methoxycarbonyl-5-nitro-6-methylaminopyridin-4-yl]piperidine-3-carbamic acid tert-butyl ester (16 mmol) was added and dissolved in 200 mL ethanol. 0.65 g 10% Pd—C was added at room temperature. The stirring was continued for 4 h by introducing hydrogen gas. The reaction solution was filtrated, and evaporated to dryness to afford 5.6 g light yellow solid with a yield of 92.3%.

(6) (R)-7-(3-tert-butoxycarbonylaminopiperidin-1-yl)-3-methyl-5-methoxycarbonyl-2-oxo-2,3-dihydro-1H-imidazo[4,5-b]pyridine

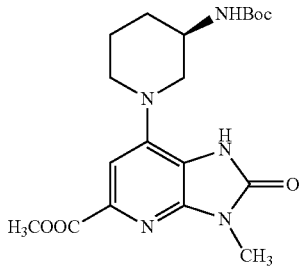

In a dry reaction bottle, 8.32 g triphosgene (28 mmol) and 7.8 mL triethylamine (56 mmol) were added and dissolved in 240 mL tetrahydrofuran. A solution of 5.31 g (R)-1-[2-methoxycarbonyl-5-amino-6-methylaminopyridin-4-yl]piperidine-3-carbamic acid tert-butyl ester (14 mmol) in tetrahydrofuran (80 mL) was added dropwise at −10° C. After addition, the reaction solution was adjusted to be neutral with saturated sodium carbonate solution. Water and dichloromethane were added to the reaction solution. The reaction solution was extracted with dichloromethane. The organic phase was combined, washed with saturated brine, dried with anhydrous sodium sulfate, evaporated to remove dichloromethane, washed with ethyl acetate, filtrated, and dried to afford 4.1 g titled product as white solid, with a yield of 72.3%.

(7) (R)-7-(3-tert-butoxycarbonylaminopiperidin-1-yl)-1-(2-cyanobenzyl)-3-methyl-5-methoxycarbonyl-2-oxo-2,3-dihydro-1H-imidazo[4,5-b]pyridine

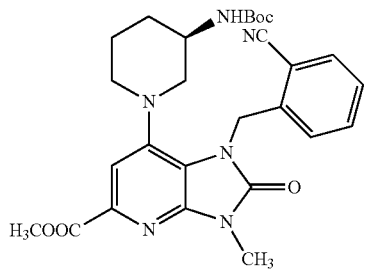

The specific operation referred to the step (5) described in Example 1 for details. 4.1 g (R)-7-(3-tert-butoxycarbonylaminopiperidin-1-yl)-3-methyl-5-methoxycarbonyl-2-oxo-2,3-dihydro-1H-imidazo[4,5-b]pyridine (10.1 mmol) was charged to afford 5.16 g light yellow solid with a yield of 98.1%.

(8) (R)-1-[1-(2-cyanobenzyl)-3-methyl-5-hydroxymethyl-2-oxo-2,3-dihydro-1H-imidazo[4,5-b]pyridin-7-yl]piperidine-3-carbamic acid tert-butyl ester

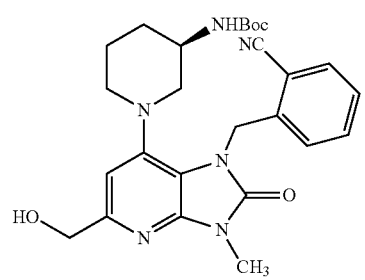 [SMILES: Cn1c(=O)n(Cc2ccccc2C#N)c2c(N3CCC[C@@H](NC(=O)OC(C)(C)C)C3)cc(CO)nc21]

1.04 g (R)-7-(3-tert-butoxycarbonylaminopiperidin-1-yl)-1-(2-cyanobenzyl)-3-methyl-5-methoxycarbonyl-2-oxo-2,3-dihydro-1H-imidazo[4,5-b]pyridine (2 mmol) was dissolved in 20 mL ethanol, to which 0.42 g potassium borohydride (8 mmol) was added in an ice bath. The stirring was continued at room temperature overnight. The reaction was monitored by TLC. After the reaction was finished, it was quenched by adding water. The reaction solution was extracted with dichloromethane for three times. The organic phase was combined, washed with saturated brine, dried with anhydrous sodium sulfate, and evaporated to dryness to afford 0.84 g crude product with a yield of 85.4%.

(9) (R)-2-[[7-(3-aminopiperidin-1-yl)-3-methyl-5-hydroxymethyl-2-oxo-2,3-dihydro-1H-imidazo[4,5-b]pyridin-1-yl]methyl]benzonitrile dihydrochlorate

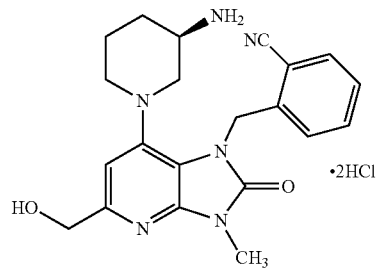 [SMILES: Cn1c(=O)n(Cc2ccccc2C#N)c2c(N3CCC[C@@H](N)C3)cc(CO)nc21 ; "·2HCl"]

0.84 g (R)-1-[1-(2-cyanobenzyl)-3-methyl-5-hydroxymethyl-2-oxo-2,3-dihydro-1H-imidazo[4,5-b]pyridin-7-yl]piperidine-3-carbamic acid tert-butyl ester (1.7 mmol) was added in a reaction bottle, to which 1 mL concentrated hydrochloric acid was added. The reaction was continued for 3 h at room temperature. The reaction solution was evaporated to dryness. A liquid phase was prepared and purified to afford 0.42 g (R)-2-[[7-(3-aminopiperidin-1-yl)-3-methyl-5-hydroxymethyl-2-oxo-2,3-dihydro-1H-imidazo[4,5-b]pyridin-1-yl]methyl]benzonitrile dihydrochlorate as white solid, with a yield of 53.1%.

Molecular formula: $C_{21}H_{24}N_6O_2$ Molecular weight: 392.45 Mass spectrum (M+H): m/z: 393.2

$^1$H-NMR (D$_2$O, 400 MHz): δ 7.73 (d, 1H), 7.50 (t, 1H), 7.37 (t, 1H), 7.02 (s, 2H), 5.50 (d, 1H), 5.39 (d, 1H), 4.60 (s, 2H), 3.38 (s, 3H), 3.13 (d, 1H), 2.97 (s, 1H), 2.85 (d, 1H), 2.77 (m, 1H), 2.60 (s, 1H), 1.97 (s, 1H), 1.61 (s, 1H), 1.38 (s, 2H).

Example 30

The preparation of (R)-7-(3-aminopiperidin-1-yl)-1-(2-cyanobenzyl)-3-methyl-2-oxo-2,3-dihydro-1H-imidazo[4,5-b]pyridine-5-formylic acid (Compound 30) dihydrochlorate

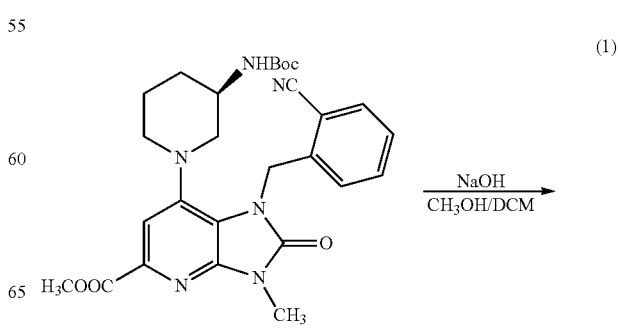

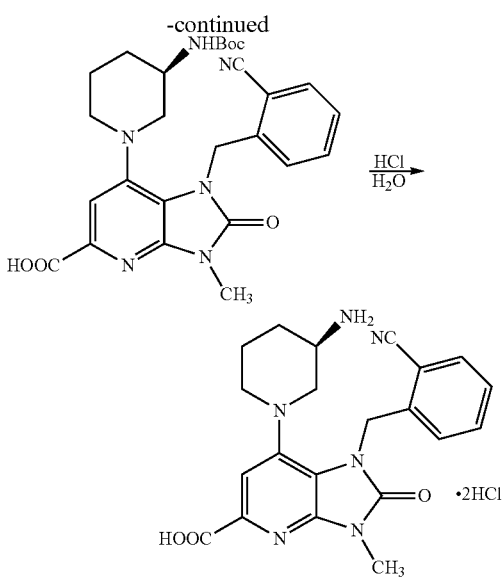

(R)-7-(3-tert-butoxycarbonylaminopiperidin-1-yl)-1-(2-cyanobenzyl)-3-methyl-2-oxo-2,3-dihydro-1H-imidazo[4,5-b]pyridine-5-formylic acid

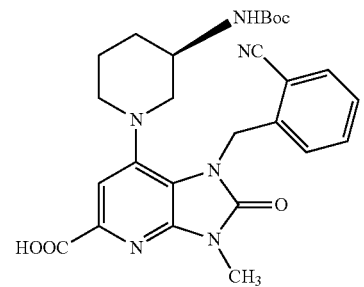 [SMILES: Cn1c(=O)n(Cc2ccccc2C#N)c2c(N3CCC[C@@H](NC(=O)OC(C)(C)C)C3)cc(C(=O)O)nc21]

1.04 g (R)-7-(3-tert-butoxycarbonylaminopiperidin-1-yl)-1-(2-cyanobenzyl)-3-methyl-2-oxo-2,3-dihydro-1H-imidazo[4,5-b]pyridine-5-formylic acid methyl ester (2.0 mmol) was added in a reaction bottle, to which 5 mL dichloromethane and 5 mL methanol were added. After dissolved completely, 0.32 g sodium hydroxide and 1 mL water were added. The reaction was monitored by TLC. After the reaction was finished, water was added. The reaction solution was adjusted to a pH of about 5 with hydrochloric acid, and extracted with dichloromethane for five times. The organic phase was combined, washed with saturated brine, dried with anhydrous sodium sulfate, and evaporated to dryness to afford 0.78 g titled product with a yield of 77.1%.

(2) (R)-7-(3-aminopiperidin-1-yl)-1-(2-cyanobenzyl)-3-methyl-2-oxo-2,3-dihydro-1H-imidazo[4,5-b]pyridine-5-formylic acid dihydrochlorate

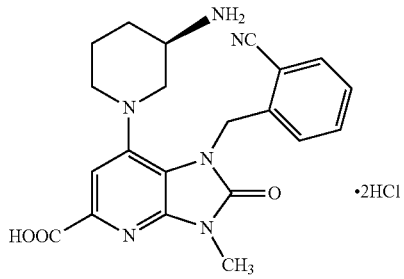 [SMILES: Cn1c(=O)n(Cc2ccccc2C#N)c2c(N3CCC[C@@H](N)C3)cc(C(=O)O)nc21]

0.78 g (R)-7-(3-tert-butoxycarbonylaminopiperidin-1-yl)-1-(2-cyanobenzyl)-3-methyl-5-formyloxy-2-oxo-2,3-dihydro-1H-imidazo[4,5-b]pyridine (1.54 mmol) was added in a reaction bottle, to which 1 mL concentrated hydrochloric acid was added. The stirring was continued for 4 h at room temperature. The reaction solution was evaporated to dryness. A liquid phase was prepared and purified to afford 0.23 g (R)-7-(3-aminopiperidin-1-yl)-1-(2-cyanobenzyl)-3-methyl-5-formyloxy-2-oxo-2,3-dihydro-1H-imidazo[4,5-b]pyridine dihydrochlorate as white solid with a yield of 31.2%.

Molecular formula: $C_{21}H_{22}N_6O_3$ Molecular weight: 406.44 Mass spectrum (M+H): m/z: 407.2

$^1$H-NMR (D$_2$O, 400 MHz): δ 7.81 (q, 1H), 7.72 (s, 1H), 7.58 (m, 1H), 7.46 (t, 1H), 6.99 (d, 1H), 5.62 (d, 1H, d), 5.49 (d, 1H), 3.58 (s, 3H), 3.20 (d, 1H), 3.14 (m, 1H), 2.90 (d, 1H), 2.78 (t, 1H), 2.65 (t, 1H), 2.08 (d, 1H), 1.72 (m, 1H), 1.49 (m, 2H).

Example 31

The preparation of (R)-7-[3-(2-cyanobenzyl)aminopiperidin-1-yl]-1-(2-cyanobenzyl)-3,5-dimethyl-2-oxo-2,3-dihydro-1H-imidazo[4,5-b]pyridine (Compound 31) hydrochlorate

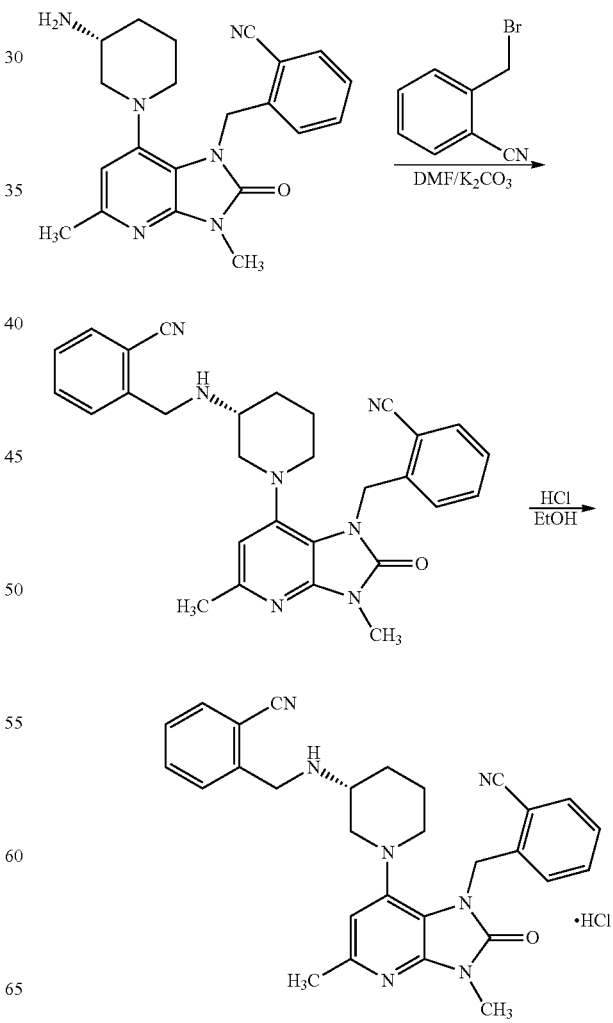

(1) (R)-7-[3-(2-cyanobenzyl)aminopiperidin-1-yl]-1-(2-cyanobenzyl)-3,5-dimethyl-2-oxo-2,3-dihydro-1H-imidazo[4,5-b]pyridine

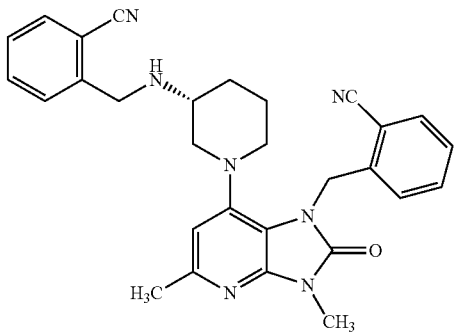 [SMILES: Cc1cc(N2CCC[C@@H](NCc3ccccc3C#N)C2)c2c(n1)n(C)c(=O)n2Cc1ccccc1C#N]

15.1 g (R)-2-[[7-(3-aminopiperidin-1-yl)-3,5-dimethyl-2-oxo-2,3-dihydro-1H-imidazo[4,5-b]pyridin-1-yl]methyl] benzonitrile (40.1 mmol) was added in a reaction bottle, to which 30 mL DMF was added. 8.6 g 2-cyano-benzyl bromide (44 mmol) and 11 g potassium carbonate (80 mmol) were added at 0° C. The reaction was continued for 3 h by stirring at room temperature. The reaction solution was extracted with dichloromethane, and washed with saturated sodium chloride solution. The organic layer was dried with anhydrous sodium sulfate, and evaporated to dryness to afford 19.68 g crude product with a yield of 99.8%.

(2) (R)-7-[3-(2-cyanobenzyl)aminopiperidin-1-yl]-1-(2-cyanobenzyl)-3,5-dimethyl-2-oxo-2,3-dihydro-1H-imidazo[4,5-b]pyridine hydrochlorate

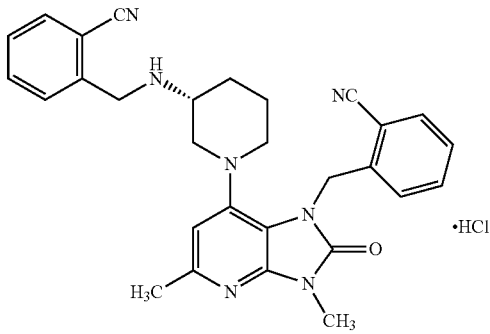 [SMILES: Cc1cc(N2CCC[C@@H](NCc3ccccc3C#N)C2)c2c(n1)n(C)c(=O)n2Cc1ccccc1C#N ; Cl]

14.7 g (R)-7-[3-(2-cyanobenzyl)aminopiperidin-1-yl]-1-(2-cyanobenzyl)-3,5-dimethyl-2-oxo-2,3-dihydroimidazo[4,5-b]pyridine (30 mmol) was added in a reaction bottle, to which 44 mL ethanol was added. The temperature was increased to 60° C. After dissolved completely, 3 mL concentrated hydrochloric acid was slowly added dropwise. After addition, the reaction solution was stirred for 1 h at room temperature, transferred to a refrigerator to precipitate a white solid, and filtrated to afford 11.51 g (R)-7-[3-(2-cyanobenzyl) aminopiperidin-1-yl]-1-(2-cyanobenzyl)-3,5-dimethyl-2-oxo-2,3-dihydroimidazo[4,5-b]pyridine hydrochlorate with a yield of 72.6%.

Molecular formula: $C_{29}H_{29}N_7O$ Molecular weight: 491.59
Mass spectrum (M+H): m/z: 492.2
$^1$H-NMR (D$_2$O, 400 MHz): δ 7.80 (d, 1H), 7.66 (t, 1H), 7.55 (d, 1H), 7.48 (m, 2H), 7.26 (d, 1H), 7.20 (t, 1H), 6.90 (s, 1H), 6.71 (t, 1H), 5.45 (d, 1H), 5.24 (d, 1H), 4.59 (d, 1H), 4.17 (d, 1H), 3.79 (m, 1H), 3.41 (s, 1H), 3.40 (s, 3H), 3.02 (t, 1H), 2.92 (t, 1H), 2.60 (s, 3H), 2.04 (d, 1H), 2.01 (s, 1H), 1.90 (d, 1H), 1.74 (m, 1H), 1.64 (m, 2H).

In accordance with the above preparation processes, the following compounds also can be prepared:

| Compound | Structural formula | Mass spectrum (M + H) |
| --- | --- | --- |
| 32 | | 263 |
| 33 | | 362 |
| 34 | | 364 |
| 35 | | 350 |
| 36 | | 369 |

-continued
| Compound | Structural formula | Mass spectrum (M + H) |
|---|---|---|
| 37 | 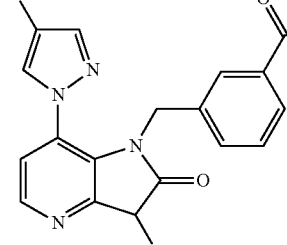 | 378 |
| 38 | | 348 |
| 39 | | 367 |
| 40 | | 361 |
| 41 | | 452 |
-continued
| Compound | Structural formula | Mass spectrum (M + H) |
|---|---|---|
| 42 | 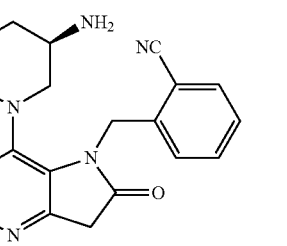 | 366 |
| 43 | | 339 |
| 44 | | 338 |
| 45 | | 372 |
| 46 | | 300 |

The invention claimed is:
1. Compounds represented by general formula (I)
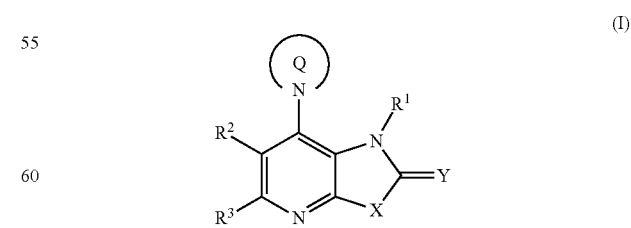
wherein:
R[1] is aryl $C_{1-6}$ alkyl, unsubstituted or substituted by 1 to 5 substituents V, wherein the substituent V is independently cyano, $C_{2-6}$ alkynyl, halogen atom, hydroxy, amino, carboxyl, C$_{1-6}$ alkyl, C$_{1-6}$ alkoxy, carbamoyl, cyano C$_{1-6}$ alkyl, halogen C$_{1-6}$ alkyl, hydroxy C$_{1-6}$ alkyl, amino C$_{1-6}$ alkyl, carboxyl C$_{1-6}$ alkyl, halogen C$_{1-6}$ alkoxy, hydroxy C$_{1-6}$ alkoxy, amino C$_{1-6}$ alkoxy, carboxyl C$_{1-6}$ alkoxy, C$_{1-6}$ alkylamino, C$_{1-6}$ alkoxyamino or di-(C$_{1-6}$ alkyl)amino;

R$^2$ and R$^3$ are independently from each other hydrogen atom, halogen atom, cyano, amino, hydroxy, carboxyl, C$_{1-6}$ alkylamino, di-(C$_{1-6}$ alkyl)amino, C$_{3-6}$ cycloalkyl, C$_{1-6}$ alkyl or C$_{1-6}$ alkoxy unsubstituted or substituted by halogen atom, hydroxy, amino, carboxyl, cyano, carbamoyl, aminosulfonyl, or R$^2$ and R$^3$ together with the C atoms they are attached to form a phenyl, 5- to 6-membered saturated or unsaturated heterocyclyl group containing at least one nitrogen atom or C$_{3-6}$ cycloalkyl;

X is O, S, NR$^4$ or CR$^5$R$^6$,

R$^4$ is hydrogen atom, C$_{1-6}$ alkyl, halogen C$_{1-6}$ alkyl, C$_{2-6}$ alkenyl or C$_{3-6}$ cycloalkyl, R$^5$ and R$^6$ are independently hydrogen atom, halogen atom, C$_{1-6}$ alkyl, halogen C$_{1-6}$ alkyl, C$_{1-6}$ alkoxy, halogen C$_{1-6}$ alkoxy, hydroxy C$_{1-6}$ alkyl, amino C$_{1-6}$ alkyl or C$_{3-6}$ cycloalkyl, or R$^5$ and R$^6$ together with the C atoms they are attached to form C$_{3-6}$ cycloalkyl;

Y is O, S or NR$^7$, R$^7$ is hydrogen atom, carbamoyl, C$_{1-6}$ alkylcarbonyl, C$_{3-6}$ cycloalkyl, or C$_{1-6}$ alkyl, C$_{1-6}$ alkoxy, aryl C$_{0-6}$ alkyl or aryl C$_{0-6}$ alkoxy, which are unsubstituted or substituted by halogen atom, hydroxy, amino, carboxyl or carbamoyl;

Q is 3- to 8-membered saturated or unsaturated heterocyclic group containing at least one nitrogen atom, which is unsubstituted or substituted by 1 to 5 substituents W, the said substituent W is independently amino, C$_{1-6}$ alkylamino, di-(C$_{1-6}$ alkyl)amino, amino C$_{1-6}$ alkyl, hydroxy C$_{1-6}$ alkyl, carboxyl C$_{1-6}$ alkyl, carbamoyl, C$_{1-6}$ alkyl, halogen C$_{1-6}$ alkyl, C$_{1-6}$ alkoxy, halogen C$_{1-6}$ alkoxy, halogen atom, formimino, C$_{1-6}$ alkylcarbonylaminomethyl, C$_{1-6}$ alkylcarbonyloxyl, C$_{1-6}$ alkylcarbamoyl or C$_{1-6}$ alkoxyformyl, pharmaceutically acceptable salts, stereoisomers or solvates thereof.

2. The compounds, their pharmaceutically acceptable salts, stereoisomers or solvates thereof according to claim 1: wherein:

R$^1$ is C$_{1-6}$ alkyl unsubstituted or substituted by 1 to 3 substituents V, wherein the substituent V is independently cyano, C$_{2-6}$ alkynyl, halogen atom, hydroxy, amino, carboxyl, C$_{1-6}$ alkyl, C$_{1-6}$ alkoxy, carbamoyl, cyano C$_{1-6}$ alkyl, halogen C$_{1-6}$ alkyl, hydroxy C$_{1-6}$ alkyl, amino C$_{1-6}$ alkyl, carboxyl C$_{1-6}$ alkyl, halogen C$_{1-6}$ alkoxy, C$_{1-6}$ alkylamino, C$_{1-6}$ alkoxyamino or di-(C$_{1-6}$ alkyl)amino;

R$^2$ and R$^3$ are independently from each other hydrogen atom, halogen atom, cyano, amino, hydroxy, carboxyl, C$_{1-6}$ alkylamino, di-(C$_{1-6}$ alkyl)amino, C$_{1-6}$ alkyl or C$_{1-6}$ alkoxy unsubstituted or substituted by halogen atom, hydroxy, amino, or R$^2$ and R$^3$ together with the C atoms they are attached to form a phenyl, 5- to 6-membered saturated or unsaturated heterocyclyl group containing at least one nitrogen atom or C$_{3-6}$ cycloalkyl;

X is O, S, NR$^4$ or CR$^5$R$^6$,

R$^4$ is hydrogen atom, C$_{1-6}$ alkyl, halogen C$_{1-6}$ alkyl, C$_{2-6}$ alkenyl or C$_{3-6}$ cycloalkyl, R$^5$ and R$^6$ are independently hydrogen atom, halogen atom, C$_{1-6}$ alkyl, halogen C$_{1-6}$ alkyl, C$_{1-6}$ alkoxy, halogen C$_{1-6}$ alkoxy or C$_{3-6}$ cycloalkyl, or R$^5$ and R$^6$ together with the C atoms they are attached to form C$_{3-6}$ cycloalkyl;

Y is O, S or NR$^7$, R$^7$ is hydrogen atom, C$_{3-6}$ cycloalkyl, or C$_{1-6}$ alkyl, C$_{1-6}$ alkoxy, phenyl C$_{0-6}$ alkyl or phenyl C$_{0-6}$ alkoxy, which are unsubstituted or substituted by halogen atom, hydroxy, amino, carboxyl or carbamoyl;

Q is 4- to 7-membered saturated or unsaturated heterocyclyl group containing at least one nitrogen atom, unsubstituted or substituted by 1 to 3 substituents W, the said substituent W is independently halogen atom, amino, C$_{1-6}$ alkylamino, di-(C$_{1-6}$ alkyl)amino, amino C$_{1-6}$ alkyl, hydroxy C$_{1-6}$ alkyl, carboxyl C$_{1-6}$ alkyl, carbamoyl, C$_{1-6}$ alkyl, halogen C$_{1-6}$ alkyl, C$_{1-6}$ alkoxy, halogen C$_{1-6}$ alkoxy, formimino, C$_{1-6}$ alkylcarbonylaminomethyl, C$_{1-6}$ alkylcarbonyloxyl, C$_{1-6}$ alkylcarbamoyl or C$_{1-6}$ alkoxyformyl.

3. Compounds of Formula (I), their pharmaceutically acceptable salts, stereoisomers or solvates:

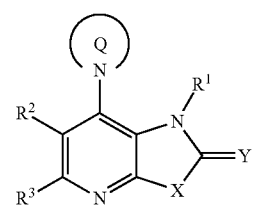

(I)

wherein:

R$^1$ is aryl C$_{1-4}$ alkyl unsubstituted or substituted by 1 to 3 substituents V, wherein the substituent V is independently cyano, cyano C$_{1-4}$ alkyl, C$_{2-4}$ alkynyl, halogen atom, C$_{1-4}$ alkyl, halogen C$_{1-4}$ alkyl, C$_{1-4}$ alkoxy, halogen C$_{1-4}$ alkoxy, amino, C$_{1-4}$ alkylamino, hydroxy, hydroxy C$_{1-4}$ alkyl or carbamoyl;

R$^2$ and R$^3$ are independently from each other hydrogen atom, halogen atom, cyano, carboxyl, C$_{1-4}$ alkylamino, di-(C$_{1-4}$ alkyl)amino, C$_{1-4}$ alkyl or C$_{1-4}$ alkoxy unsubstituted or substituted by halogen atom, hydroxy, amino, or R$^2$ and R$^3$ together with the C atoms they are attached to form a phenyl, pyridyl, pyrrolidinyl, imidazolidinyl, oxazolidinyl, thiazolidinyl, cyclopentyl or cyclohexyl;

X is O, S, NR$^4$ or CR$^5$R$^6$,

R$^4$ is hydrogen atom, C$_{1-4}$ alkyl, halogen C$_{1-4}$ alkyl, C$_{2-4}$ alkenyl or C$_{3-6}$ cycloalkyl, R$^5$ and R$^6$ are independently hydrogen atom, halogen atom, C$_{1-4}$ alkyl, halogen C$_{1-4}$ alkyl, C$_{1-4}$ alkoxy, halogen C$_{1-4}$ alkoxy or C$_{3-5}$ cycloalkyl, or R$^5$ and R$^6$ together with the C atoms they are attached to form C$_{3-6}$ cycloalkyl;

Y is O, S or NR$^7$, R$^7$ is hydrogen atom or C$_{1-4}$ alkyl;

Q is azetidinyl, pyrrolidinyl, pyrrolyl, 4,5-dihydro imidazolyl, imidazolyl, pyrazolidinyl, pyrazolyl, 4,5-dihydro pyrazolyl, pyrazolidinyl, piperidyl, homopiperazinyl, homopiperidyl, piperazinyl or morpholinyl, which are unsubstituted or substituted by 1 to 3 substituents W, the said substituent W is independently halogen atom, amino, C$_{1-4}$ alkylamino, di-(C$_{1-4}$ alkyl)amino, amino C$_{1-4}$ alkyl, hydroxy C$_{1-4}$ alkyl, carboxyl C$_{1-4}$ alkyl, carbamoyl, C$_{1-4}$ alkyl, halogen C$_{1-4}$ alkyl, C$_{1-4}$ alkoxy, formimino, C$_{1-4}$ alkylcarbonylaminomethyl, C$_{1-4}$ alkylcarbonyloxyl, C$_{1-4}$ alkylcarbamoyl, C$_{1-4}$ alkoxyformyl, acetamido or 2-cyano-phenylmethylamino.

4. The compounds, their pharmaceutically acceptable salts, stereoisomers or solvates thereof according to claim 3: wherein:
- $R^1$ is aryl $C_{1-4}$ alkyl unsubstituted or substituted by 1 to 3 substituents V, wherein the substituent V is independently cyano, cyanomethyl, acetenyl, fluorine atom, chlorine atom, methyl, trifluoromethyl, methoxy, trifluoromethoxy, amino, methylamino, hydroxymethyl or carbamoyl;
- $R^2$ and $R^3$ are independently from each other hydrogen atom, fluorine atom, chlorine atom, cyano, methyl, ethyl, fluoromethyl, difluoromethyl, trifluoromethyl, hydroxymethyl, carboxyl, aminomethyl, methylamino, di-(methyl)amino, methoxy, trifluoromethoxy, or $R^2$ and $R^3$ together with the C atoms they are attached to form a phenyl for pyridyl;
- X is O, S, $NR^4$ or $CR^5R^6$,
- $R^4$ is hydrogen atom, methyl, ethyl, isopropyl, trifluoromethyl, ethenyl or cyclopropyl,
- $R^5$ and $R^6$ are independently hydrogen atom, fluorine atom, methyl, ethyl, trifluoromethyl or methoxy, or
- $R^5$ and $R^6$ together with the C atoms they are attached to form cyclopropyl, cyclobutyl, cyclopentyl or cyclohexyl;
- Y is O, S OR $NR^7$, $R^7$ is hydrogen atom or methyl;
- Q is pyrrolidinyl, piperazinyl, piperidyl, homopiperazinyl, homopiperidyl or azetidinyl, which are unsubstituted or substituted by 1 to 2 substituents W, the said substituent W is independently fluorine atom, chlorine atom, amino, methylamino, di-(methyl)amino, aminomethyl, methyl, ethyl, methoxy, methoxy formyl, hydroxymethyl, acetamido or 2-cyano-phenylmethylamino.

5. The compounds, their pharmaceutically acceptable salts, stereoisomers or solvates thereof according to claim 4: wherein:
- $R^1$ is arylmethyl unsubstituted or substituted by 1 to 3 substituents V, wherein the substituent V is independently cyano, acetenyl, fluorine atom, chlorine atom, methyl, trifluoromethyl, methoxy or trifluoromethoxy;
- $R^2$ and $R^3$ are independently from each other hydrogen atom, fluorine atom, chlorine atom, methyl, ethyl, fluoromethyl, difluoromethyl, trifluoromethyl, hydroxy methyl, carboxyl, amino methyl, methylamino, di-(methyl)amino, methoxy, or $R^2$ and $R^3$ together with the C atoms they are attached to form a phenyl or pyridyl;
- X is O, $NR^4$ or $CR^5R^6$,
- $R^4$ is hydrogen atom, methyl, ethyl, isopropyl or trifluoromethyl,
- $R^5$ and $R^6$ are independently hydrogen atom, fluorine atom, methyl, ethyl or trifluoromethyl;
- Y is O or S;
- Q is pyrrolidinyl, piperazinyl, piperidyl, homopiperazinyl, homopiperidyl or azetidinyl, which are unsubstituted or substituted by 1 to 2 substituents W, the said substituent W is independently fluorine atom, chlorine atom, amino, methylamino, aminomethyl, methyl, di-(methyl)amino, acetamido or 2-cyano-phenylmethylamino.

6. The compounds, their pharmaceutically acceptable salts, stereoisomers or solvates thereof according to claim 5: wherein:
- $R^1$ is phenylmethyl or naphthylmethyl, which are unsubstituted or substituted by 1 to 3 substituents V, wherein the substituent V is independently cyano, acetenyl, fluorine atom, chlorine atom or methyl;
- $R^2$ and $R^3$ are independently from each other hydrogen atom, fluorine atom, chlorine atom, methyl, ethyl, fluoromethyl, difluoromethyl, trifluoromethyl, hydroxymethyl, carboxyl, aminomethyl, methylamino, di-(methyl)amino, or $R^2$ and $R^3$ together with the C atoms they are attached to form a phenyl;
- X is O, $NR^4$ or $CR^5R^6$,
- $R^4$ is hydrogen atom, methyl, ethyl or isopropyl,
- $R^5$ and $R^6$ are independently hydrogen atom, methyl or ethyl;
- Y is O or S;
- Q is pyrrolidinyl, piperazinyl, piperidyl, homopiperazinyl, homopiperidyl or azetidinyl, which are unsubstituted or substituted by 1 to 2 substituents W, the said substituent W is independently fluorine atom, amino, methylamino, methyl, di-(methyl)amino, acetamido or 2-cyano-phenylmethylamino.

7. The compounds, their pharmaceutically acceptable salts, stereoisomers or solvates thereof according to claim 6: wherein:
- $R^1$ is phenylmethyl or naphthylmethyl, which are unsubstituted or substituted by 1 to 2 substituents V, wherein the substituent V is independently cyano, acetenyl, fluorine atom or chlorine atom;
- $R^2$ and $R^3$ are independently from each other hydrogen atom, chlorine atom, methyl, ethyl, hydroxymethyl, carboxyl, aminomethyl, methylamino, di-(methyl)amino, or $R^2$ and $R^3$ together with the C atoms they are attached to form a phenyl;
- X is O, $NR^4$ or $CR^5R^6$,
- $R^4$ is hydrogen atom, methyl, ethyl or isopropyl,
- $R^5$ and $R^6$ are independently hydrogen atom or methyl;
- Y is O or S;
- Q is pyrrolidinyl, piperazinyl, piperidyl, homopiperazinyl, homopiperidyl or azetidinyl, which are unsubstituted or substituted by one substituent W, the said substituent W is amino, methylamino, di-(methyl)amino, acetamido or 2-cyano-phenylmethylamino.

8. The compounds, their pharmaceutically acceptable salts, stereoisomers or solvates thereof according to claim 7:

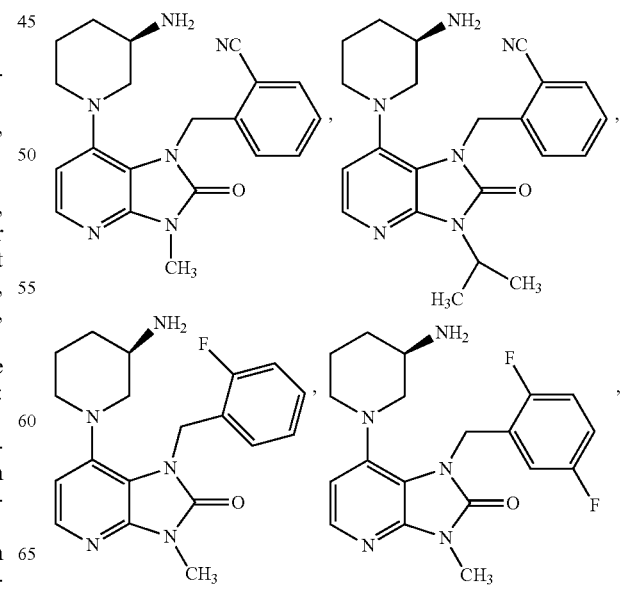

137
-continued
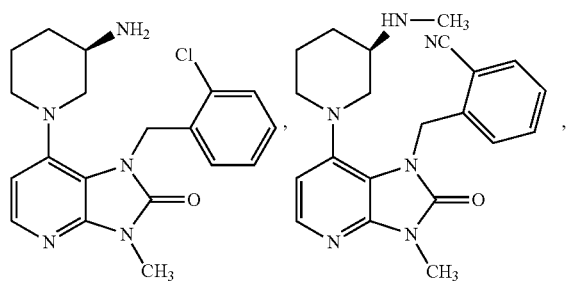
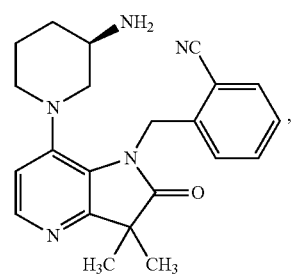
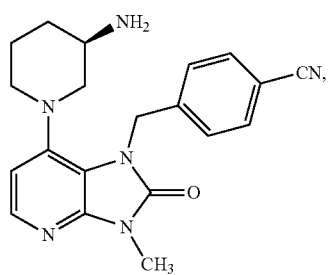
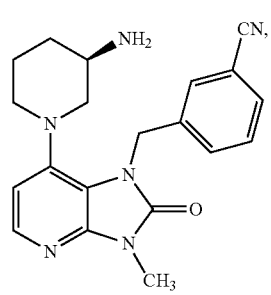
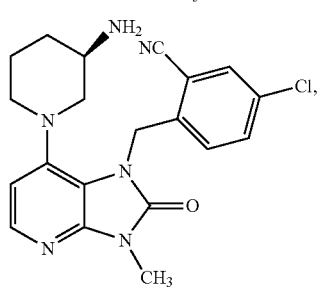
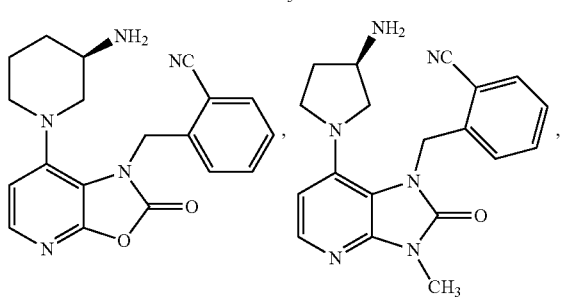
138
-continued
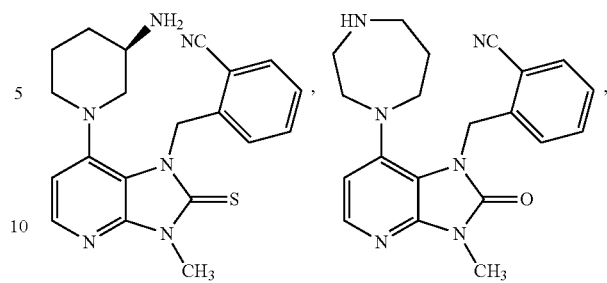
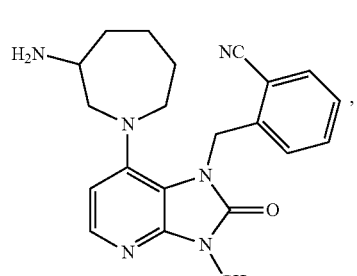
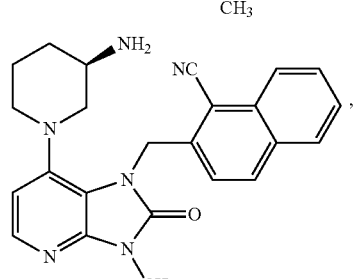
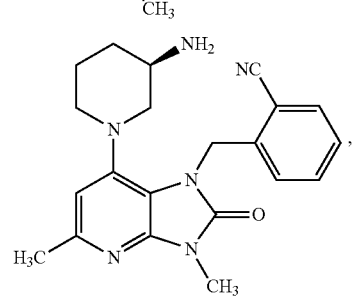
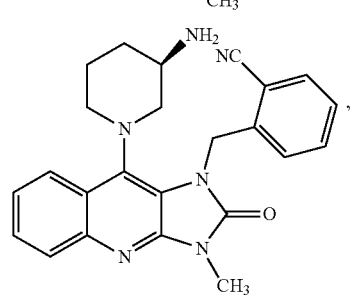
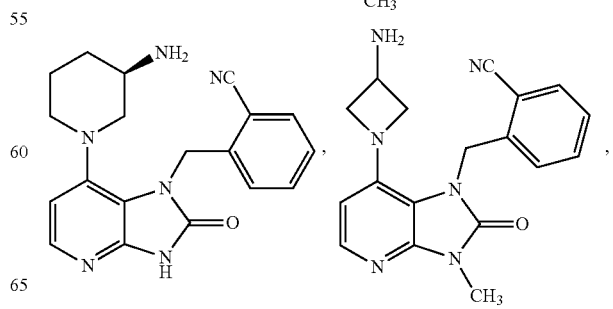

-continued

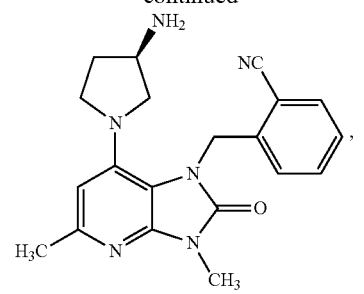

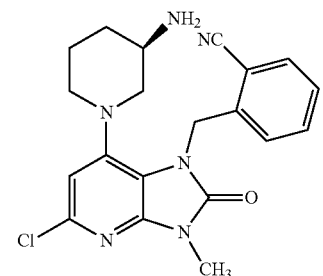

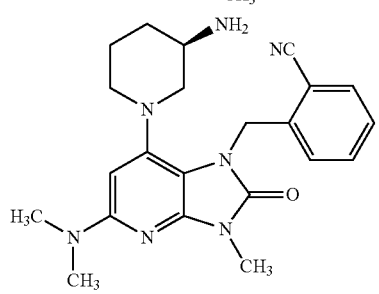

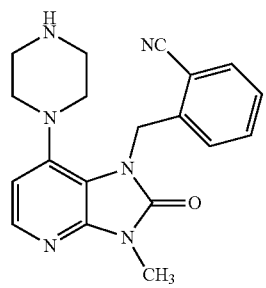 [SMILES: Cn1c(=O)n(Cc2ccccc2C#N)c2c(N3CCNCC3)ccnc21]

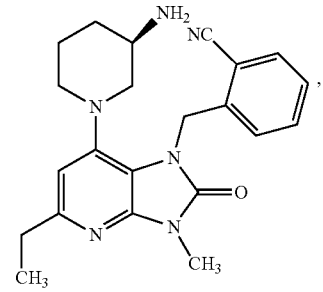

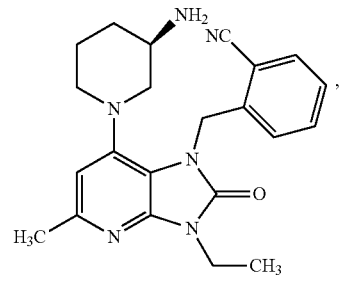

-continued

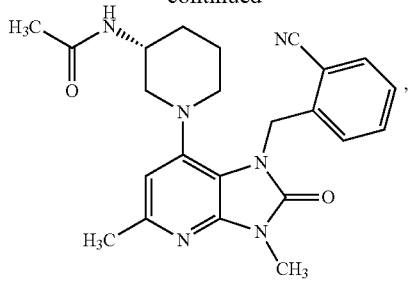

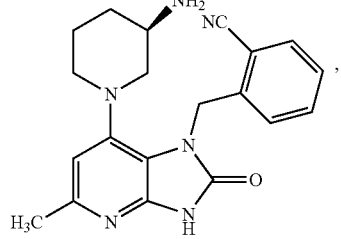

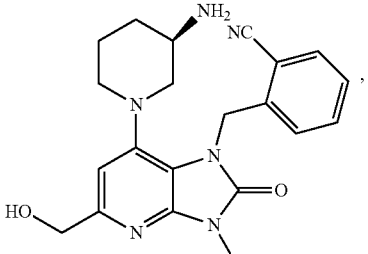

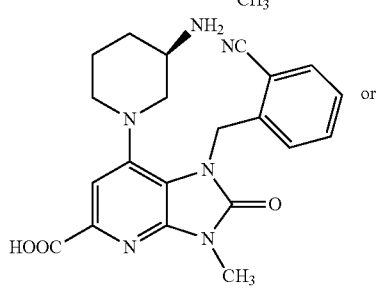

, or

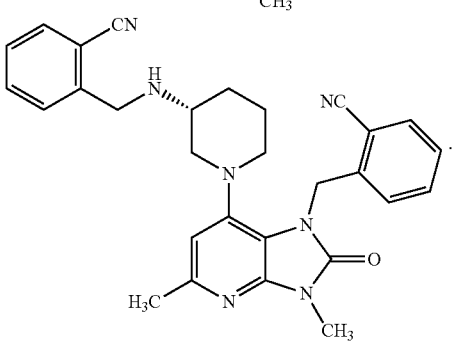

.

9. The compounds, their pharmaceutically acceptable salts, stereoisomers or solvates thereof according to claim 1, wherein their pharmaceutically acceptable salts are the salts of benzoic acid, benzenesulfonic acid, p-toluene sulfonic acid, citric acid, maleic acid, fumaric acid, tartaric acid, hydrobromic acid, hydrochloric acid, sulphuric acid, nitric acid, or phosphoric acid, arginine, meglumine, glucosamine or ammonium, lithium, sodium, potassium, calcium, magnesium, zinc, barium salts.

10. A pharmaceutical composition, comprising the compounds, their pharmaceutically acceptable salts, stereoisomers or solvates thereof according to claim 1 and one or more pharmaceutically acceptable carriers.

11. A method for treating noninsulin-dependent diabetes, hyperglycemia hyperlipidemia or insulin resistance comprising administering to a subject in need thereof an effective amount of a compound of claim 1, or pharmaceutically acceptable salts, stereoisomers or solvates thereof.

12. Compounds of general formula (I)

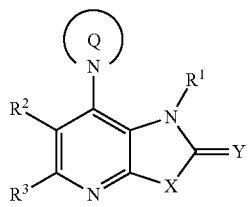

(I)

wherein:
$R^1$ is $C_{1-6}$ alkyl, $C_{3-6}$ alkenyl or $C_{2-6}$ alkynyl, which are unsubstituted or substituted by halogen atom, hydroxy, amino, carboxyl, carbamoyl or aminosulfonyl, or aryl $C_{1-6}$ alkyl, unsubstituted or substituted by 1 to 5 substituents V, wherein the substituent V is independently cyano, $C_{2-6}$ alkynyl, halogen atom, hydroxy, amino, carboxyl, $C_{1-6}$ alkyl, $C_{1-6}$ alkoxy, carbamoyl, cyano $C_{1-6}$ alkyl, halogen $C_{1-6}$ alkyl, hydroxy $C_{1-6}$ alkyl, amino $C_{1-6}$ alkyl, carboxyl $C_{1-6}$ alkyl, halogen $C_{1-6}$ alkoxy, hydroxy $C_{1-6}$ alkoxy, amino $C_{1-6}$ alkoxy, carboxyl $C_{1-6}$ alkoxy, $C_{1-6}$ alkylamino, $C_{1-6}$ alkoxyamino or di-($C_{1-6}$ alkyl)amino;

$R^2$ and $R^3$ are independently from each other hydrogen atom, halogen atom, cyano, amino, hydroxy, carboxyl, $C_{1-6}$ alkylamino, di-($C_{1-6}$ alkyl)amino, $C_{3-6}$ cycloalkyl, $C_{1-6}$ alkyl or $C_{1-6}$ alkoxy unsubstituted or substituted by halogen atom, hydroxy, amino, carboxyl, cyano, carbamoyl, aminosulfonyl, or $R^2$ and $R^3$ together with the C atoms they are attached to form a phenyl, 5- to 6-membered saturated or unsaturated heterocyclyl group containing at least one nitrogen atom or $C_{3-6}$ cycloalkyl;

X is O, S, $NR^4$ or $CR^5R^6$,
$R^4$ is $C_{1-6}$ alkyl, halogen $C_{1-6}$ alkyl, $C_{2-6}$ alkenyl or $C_{3-6}$ cycloalkyl,
$R^5$ and $R^6$ are independently hydrogen atom, halogen atom, $C_{1-6}$ alkyl, halogen $C_{1-6}$ alkyl, $C_{1-6}$ alkoxy, halogen $C_{1-6}$ alkoxy, hydroxy $C_{1-6}$ alkyl, amino $C_{1-6}$ alkyl or $C_{3-6}$ cycloalkyl, or
$R^5$ and $R^6$ together with the C atoms they are attached to form $C_{3-6}$ cycloalkyl;

Y is O, S or $NR^7$, $R^7$ is hydrogen atom, carbamoyl, $C_{1-6}$ alkylcarbonyl, $C_{3-6}$ cycloalkyl, or
$C_{1-6}$ alkyl, $C_{1-6}$ alkoxy, aryl $C_{0-6}$ alkyl or aryl $C_{0-6}$ alkoxy, which are unsubstituted or substituted by halogen atom, hydroxy, amino, carboxyl or carbamoyl;

Q is 3- to 8-membered saturated or unsaturated heterocyclic group containing at least one nitrogen atom, which is unsubstituted or substituted by 1 to 5 substituents w, the said substituent W is independently amino, $C_{1-6}$ alkylamino, di-($C_{1-6}$ alkyl)amino, amino $C_{1-6}$ alkyl, hydroxy $C_{1-6}$ alkyl, carboxyl $C_{1-6}$ alkyl, carbamoyl, $C_{1-6}$ alkyl, halogen $C_{1-6}$ alkyl, $C_{1-6}$ alkoxy, halogen $C_{1-6}$ alkoxy, halogen atom, formimino, $C_{1-6}$ alkylcarbonylaminomethyl, $C_{1-6}$ alkylcarbonyloxyl, $C_{1-6}$ alkylcarbamoyl or $C_{1-6}$ alkoxyformyl, or pharmaceutically acceptable salts, stereoisomers or solvates thereof.

13. The compounds according to claim 12:
wherein:
$R^1$ is $C_{3-6}$ alkenyl, $C_{3-6}$ alkynyl, or aryl $C_{1-6}$ alkyl unsubstituted or substituted by 1 to 3 substituents V, wherein the substituent V is independently cyano, $C_{2-6}$ alkynyl, halogen atom, hydroxy, amino, carboxyl, $C_{1-6}$ alkyl, $C_{1-6}$ alkoxy, carbamoyl, cyano $C_{1-6}$ alkyl, halogen $C_{1-6}$ alkyl, hydroxy $C_{1-6}$ alkyl, amino $C_{1-6}$ alkyl, carboxyl $C_{1-6}$ alkyl, halogen $C_{1-6}$ alkoxy, $C_{1-6}$ alkylamino, $C_{1-6}$ alkoxyamino or di-($C_{1-6}$ alkyl)amino;

$R^2$ and $R^3$ are independently from each other hydrogen atom, halogen atom, cyano, amino, hydroxy, carboxyl, $C_{1-6}$ alkylamino, di-($C_{1-6}$ alkyl)amino,
$C_{1-6}$ alkyl or $C_{1-6}$ alkoxy unsubstituted or substituted by halogen atom, hydroxy, amino, or
$R^2$ and $R^3$ together with the C atoms they are attached to form a phenyl, 5- to 6-membered saturated or unsaturated heterocyclyl group containing at least one nitrogen atom or $C_{3-6}$ cycloalkyl;

X is O, S, $NR^4$ or $CR^5R^6$,
$R^4$ is $C_{1-6}$ alkyl, halogen $C_{1-6}$ alkyl, $C_{2-6}$ alkenyl or $C_{3-6}$ cycloalkyl,
$R^5$ and $R^6$ are independently hydrogen atom, halogen atom, $C_{1-6}$ alkyl, halogen $C_{1-6}$ alkyl, $C_{1-6}$ alkoxy, halogen $C_{1-6}$ alkoxy or $C_{3-6}$ cycloalkyl, or
$R^5$ and $R^6$ together with the C atoms they are attached to form $C_{3-6}$ cycloalkyl;

Y is O, S or $NR^7$, $R^7$ is hydrogen atom, $C_{3-6}$ cycloalkyl, or
$C_{1-6}$ alkyl, $C_{1-6}$ alkoxy, phenyl $C_{0-6}$ alkyl or phenyl $C_{0-6}$ alkoxy, which are unsubstituted or substituted by halogen atom, hydroxy, amino, carboxyl or carbamoyl;

Q is 4- to 7-membered saturated or unsaturated heterocyclyl group containing at least one nitrogen atom, unsubstituted or substituted by 1 to 3 substituents W, the said substituent W is independently halogen atom, amino, $C_{1-6}$ alkylamino, di-($C_{1-6}$ alkyl)amino, amino $C_{1-6}$ alkyl, hydroxy $C_{1-6}$ alkyl, carboxyl $C_{1-6}$ alkyl, carbamoyl, $C_{1-6}$ alkyl, halogen $C_{1-6}$ alkyl, $C_{1-6}$ alkoxy, halogen $C_{1-6}$ alkoxy, formimino, $C_{1-6}$ alkylcarbonylaminomethyl, $C_{1-6}$ alkylcarbonyloxyl, $C_{1-6}$ alkylcarbamoyl or $C_{1-6}$ alkoxyformyl.

14. The compounds according to claim 13, wherein:
$R^1$ is aryl $C_{1-4}$ alkyl unsubstituted or substituted by 1 to 3 substituents V, wherein the substituent V is independently cyano, cyano $C_{1-4}$ alkyl, $C_{2-4}$ alkynyl, halogen atom, $C_{1-4}$ alkyl, halogen $C_{1-4}$ alkyl, $C_{1-4}$ alkoxy, halogen $C_{1-4}$ alkoxy, amino, $C_{1-4}$ alkylamino, hydroxy, hydroxy $C_{1-4}$ alkyl or carbamoyl;

$R^2$ and $R^3$ are independently from each other hydrogen atom, halogen atom, cyano, carboxyl, $C_{1-4}$ alkylamino, di-($C_{1-4}$ alkyl)amino,
$C_{1-4}$ alkyl or $C_{1-4}$ alkoxy unsubstituted or substituted by halogen atom, hydroxy, amino, or
$R^2$ and $R^3$ together with the C atoms they are attached to form a phenyl, pyridyl, pyrrolidinyl, imidazolidinyl, oxazolidinyl, thiazolidinyl, cyclopentyl or cyclohexyl;

X is O, S, $NR^4$ or $CR^5R^6$,
$R^4$ is $C_{1-4}$ alkyl, halogen $C_{1-4}$ alkyl, $C_{2-4}$ alkenyl or $C_{3-6}$ cycloalkyl,
$R^5$ and $R^6$ are independently hydrogen atom, halogen atom, $C_{1-4}$ alkyl, halogen $C_{1-4}$ alkyl, $C_{1-4}$ alkoxy, halogen $C_{1-4}$ alkoxy or $C_{3-5}$ cycloalkyl, or
$R^5$ and $R^6$ together with the C atoms they are attached to form $C_{3-6}$ cycloalkyl;

Y is O, S or $NR^7$, $R^7$ is hydrogen atom or $C_{1-4}$ alkyl;

Q is azetidinyl, pyrrolidinyl, pyrrolyl, 4,5-dihydro imidazolyl, imidazolyl, pyrazolidinyl, pyrazolyl, 4,5-dihydro pyrazolyl, pyrazolidinyl, piperidyl, homopiperazinyl, homopiperidyl, piperazinyl or morpholinyl, which are unsubstituted or substituted by 1 to 3 substituents W, the said substituent W is independently halogen atom, amino, $C_{1-4}$ alkylamino, di-($C_{1-4}$ alkyl)amino, amino $C_{1-4}$ alkyl, hydroxy $C_{1-4}$ alkyl, carboxyl $C_{1-4}$ alkyl, carbamoyl, $C_{1-4}$ alkyl, halogen $C_{1-4}$ alkyl, $C_{1-4}$ alkoxy, formimino, $C_{1-4}$ alkylcarbonylaminomethyl, $C_{1-4}$ alkylcarbonyloxyl, $C_{1-4}$ alkylcarbamoyl, $C_{1-4}$ alkoxyformyl, acetamido or 2-cyano-phenylmethylamino.

15. The compounds according to claim 14:
wherein:
$R^1$ is aryl $C_{1-4}$ alkyl unsubstituted or substituted by 1 to 3 substituents V, wherein the substituent V is independently cyano, cyanomethyl, acetenyl, fluorine atom, chlorine atom, methyl, trifluoromethyl, methoxy, trifluoromethoxy, amino, methylamino, hydroxymethyl or carbamoyl;
$R^2$ and $R^3$ are independently from each other hydrogen atom, fluorine atom, chlorine atom, cyano, methyl, ethyl, fluoromethyl, difluoromethyl, trifluoromethyl, hydroxymethyl, carboxyl, aminomethyl, methylamino, di-(methyl)amino, methoxy, trifluoromethoxy, or $R^2$ and $R^3$ together with the C atoms they are attached to form a phenyl for pyridyl;
X is O, S, $NR^4$ or $CR^5R^6$,
$R^4$ is methyl, ethyl, isopropyl, trifluoromethyl, ethenyl or cyclopropyl,
$R^5$ and $R^6$ are independently hydrogen atom, fluorine atom, methyl, ethyl, trifluoromethyl or methoxy, or
$R^5$ and $R^6$ together with the C atoms they are attached to form cyclopropyl, cyclobutyl, cyclopentyl or cyclohexyl;
Y is O, S OR $NR^7$, $R^7$ is hydrogen atom or methyl;
Q is pyrrolidinyl, piperazinyl, piperidyl, homopiperazinyl, homopiperidyl or azetidinyl, which are unsubstituted or substituted by 1 to 2 substituents W, the said substituent W is independently fluorine atom, chlorine atom, amino, methylamino, di-(methyl)amino, aminomethyl, methyl, ethyl, methoxy, methoxy formyl, hydroxymethyl, acetamido or 2-cyano-phenylmethylamino.

16. The compounds according to claim 15:
wherein:
$R^1$ is arylmethyl unsubstituted or substituted by 1 to 3 substituents V, wherein the substituent V is independently cyano, acetenyl, fluorine atom, chlorine atom, methyl, trifluoromethyl, methoxy or trifluoromethoxy;
$R^2$ and $R^3$ are independently from each other hydrogen atom, fluorine atom, chlorine atom, methyl, ethyl, fluoromethyl, difluoromethyl, trifluoromethyl, hydroxy methyl, carboxyl, amino methyl, methylamino, di-(methyl)amino, methoxy, or $R^2$ and $R^3$ together with the C atoms they are attached to form a phenyl or pyridyl;
X is O, $NR^4$ or $CR^5R^6$,
$R^4$ is methyl, ethyl, isopropyl or trifluoromethyl,
$R^5$ and $R^6$ are independently hydrogen atom, fluorine atom, methyl, ethyl or trifluoromethyl;
Y is O or S;
Q is pyrrolidinyl, piperazinyl, piperidyl, homopiperazinyl, homopiperidyl or azetidinyl, which are unsubstituted or substituted by 1 to 2 substituents W, the said substituent W is independently fluorine atom, chlorine atom, amino, methylamino, aminomethyl, methyl, di-(methyl)amino, acetamido or 2-cyano-phenylmethylamino.

17. The compounds according to claim 16:
wherein:
$R^1$ is phenylmethyl or naphthylmethyl, which are unsubstituted or substituted by 1 to 3 substituents V, wherein the substituent V is independently cyano, acetenyl, fluorine atom, chlorine atom or methyl;
$R^2$ and $R^3$ are independently from each other hydrogen atom, fluorine atom, chlorine atom, methyl, ethyl, fluoromethyl, difluoromethyl, trifluoromethyl, hydroxymethyl, carboxyl, aminomethyl, methylamino, di-(methyl)amino, or $R^2$ and $R^3$ together with the C atoms they are attached to form a phenyl;
X is O, $NR^4$ or $CR^5R^6$,
$R^4$ is methyl, ethyl or isopropyl,
$R^5$ and $R^6$ are independently hydrogen atom, methyl or ethyl;
Y is O or S;
Q is pyrrolidinyl, piperazinyl, piperidyl, homopiperazinyl, homopiperidyl or azetidinyl, which are unsubstituted or substituted by 1 to 2 substituents W, the said substituent W is independently fluorine atom, amino, methylamino, methyl, di-(methyl)amino, acetamido or 2-cyano-phenylmethylamino.

18. The compounds according to claim 17:
wherein:
$R^1$ is phenylmethyl or naphthylmethyl, which are unsubstituted or substituted by 1 to 2 substituents V, wherein the substituent V is independently cyano, acetenyl, fluorine atom or chlorine atom;
$R^2$ and $R^3$ are independently from each other hydrogen atom, chlorine atom, methyl, ethyl, hydroxymethyl, carboxyl, aminomethyl, methylamino, di-(methyl)amino, or $R^2$ and $R^3$ together with the C atoms they are attached to form a phenyl;
X is O, $NR^4$ or $CR^5R^6$,
$R^4$ is methyl, ethyl or isopropyl,
$R^5$ and $R^6$ are independently hydrogen atom or methyl;
Y is O or S;
Q is pyrrolidinyl, piperazinyl, piperidyl, homopiperazinyl, homopiperidyl or azetidinyl, which are unsubstituted or substituted by one substituent W, the said substituent W is amino, methylamino, di-(methyl)amino, acetamido or 2-cyano-phenylmethylamino.

* * * * *

UNITED STATES PATENT AND TRADEMARK OFFICE
CERTIFICATE OF CORRECTION

PATENT NO. : 8,680,089 B2
APPLICATION NO. : 13/522304
DATED : March 25, 2014
INVENTOR(S) : Zhenhua Huang et al.

Page 1 of 1

It is certified that error appears in the above-identified patent and that said Letters Patent is hereby corrected as shown below:

In the claims

Column 135, Line 16, Claim 4:
"phenyl for pyridyl;" should read, --phenyl or pyridyl--.

Column 141, Line 61, Claim 12:
"is unsubstituted or substituted by 1 to 5 substituents w," should read, --is unsubstituted or substituted by 1 to 5 substituents W,--.

Signed and Sealed this
Eighth Day of December, 2015

Michelle K. Lee
*Director of the United States Patent and Trademark Office*